US012089870B2

(12) United States Patent
Dharan et al.

(10) Patent No.: US 12,089,870 B2
(45) Date of Patent: Sep. 17, 2024

(54) DEVICES AND METHODS FOR ACCESSING THE LEFT ATRIUM FOR CARDIAC PROCEDURES

(71) Applicant: MITRx, Inc., San Jose, CA (US)

(72) Inventors: Murali Dharan, Danville, CA (US); Albert K. Chin, Palo Alto, CA (US); Jeffry J. Grainger, Portola Valley, CA (US)

(73) Assignee: MITRx, Inc., San Jose, CA (US)

(*) Notice: Subject to any disclaimer, the term of this patent is extended or adjusted under 35 U.S.C. 154(b) by 0 days.

(21) Appl. No.: 18/189,811

(22) Filed: Mar. 24, 2023

(65) Prior Publication Data
US 2023/0233228 A1 Jul. 27, 2023

Related U.S. Application Data

(63) Continuation of application No. 16/740,896, filed on Jan. 13, 2020, which is a continuation of application No. PCT/US2018/042171, filed on Jul. 13, 2018.

(60) Provisional application No. 62/532,082, filed on Jul. 13, 2017.

(51) Int. Cl.
*A61B 17/34* (2006.01)
*A61B 1/31* (2006.01)
*A61B 1/313* (2006.01)

(52) U.S. Cl.
CPC ........ *A61B 17/3415* (2013.01); *A61B 1/3137* (2013.01); *A61B 17/3431* (2013.01); *A61B 2017/3425* (2013.01); *A61B 2017/3445* (2013.01)

(58) Field of Classification Search
CPC ......... A61B 17/3415; A61B 2017/3425; A61F 2/24; A61F 2/2427
See application file for complete search history.

(56) References Cited

U.S. PATENT DOCUMENTS

| 5,797,960 | A | * | 8/1998 | Stevens | .......... A61B 17/320016 |
| | | | | | 606/213 |
| 10,433,960 | B1 | * | 10/2019 | Sutherland | .......... A61B 17/3478 |
| 2004/0015193 | A1 | * | 1/2004 | Lamson | ............... A61N 1/0573 |
| | | | | | 607/9 |
| 2014/0222031 | A1 | * | 8/2014 | Stack | .................... A61F 2/2427 |
| | | | | | 606/144 |

* cited by examiner

*Primary Examiner* — Nicholas W Woodall
(74) *Attorney, Agent, or Firm* — HelixIP LLP

(57) ABSTRACT

Systems, devices, and methods for providing access to the heart. The system includes an intracardiac access device comprising an elongate member having a channel extending between a distal end and a proximal end thereof. The intracardiac access device is configured to be advanced through an extrapericardial penetration in the left atrial wall without penetrating the pericardium of the heart. An optional procedural device is configured to be advanced through the channel of the intracardiac access device into an internal chamber of the heart and configured to perform a surgical procedure in the internal chamber of the heart. A working channel of an optional suprasternal access device is configured to facilitate access of the intracardiac access device into the body of the patient by providing a path from a suprasternal opening to a position adjacent the roof of the left atrium.

20 Claims, 35 Drawing Sheets

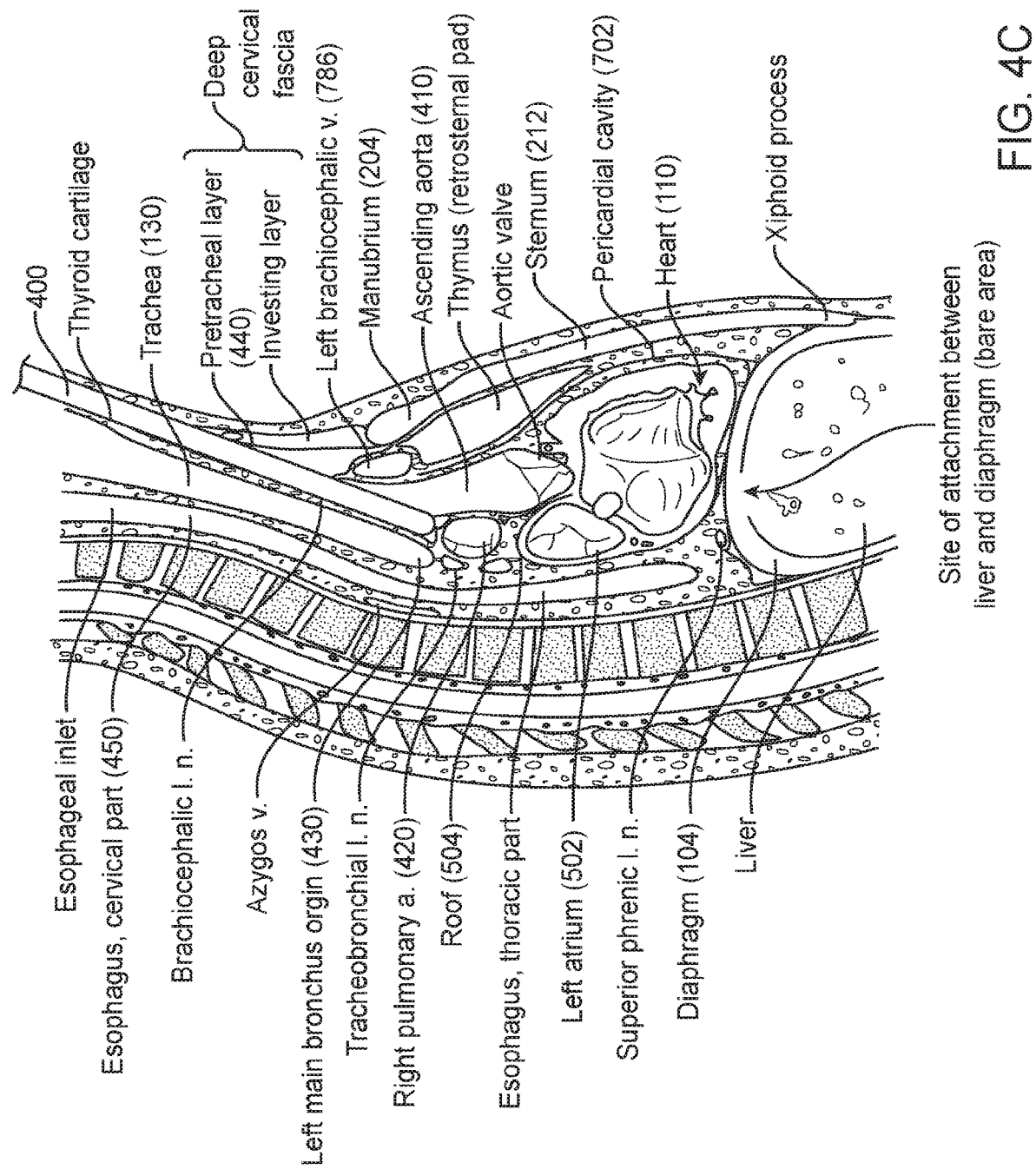

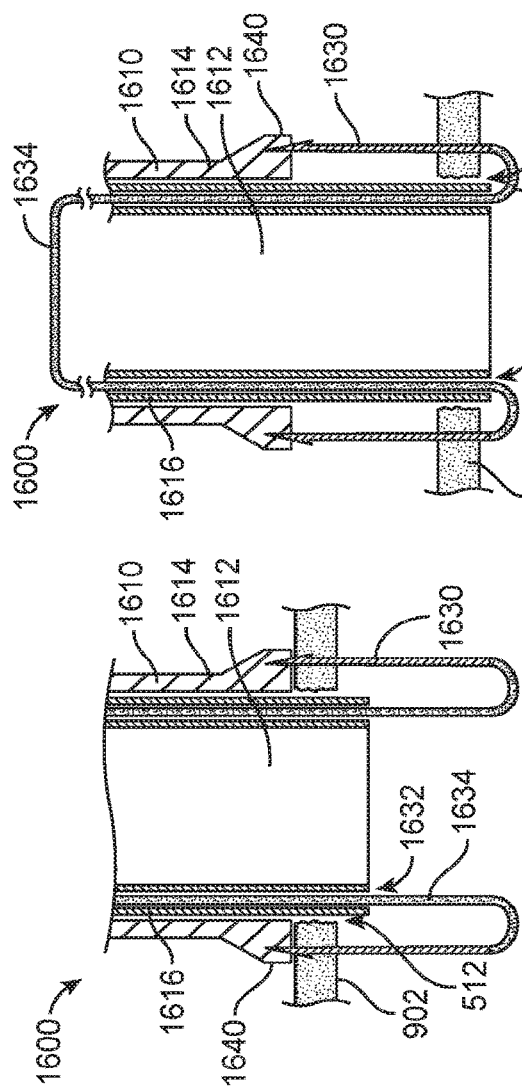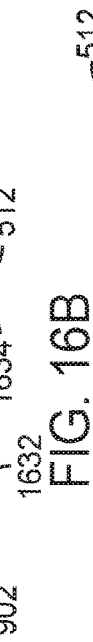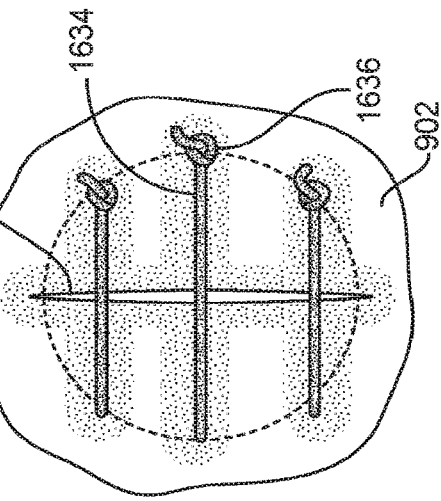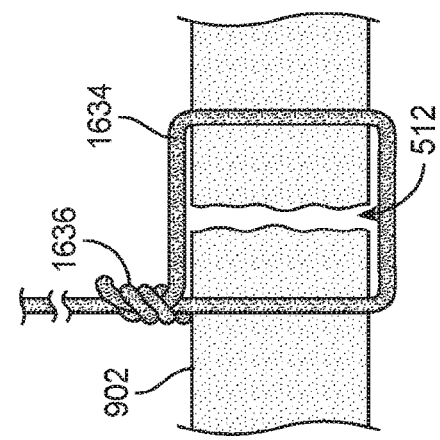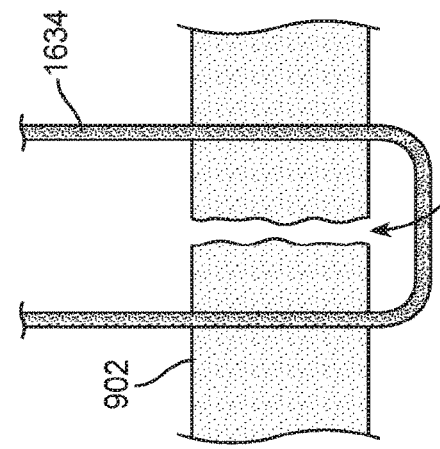

DEVICES AND METHODS FOR ACCESSING THE LEFT ATRIUM FOR CARDIAC PROCEDURES

CROSS-REFERENCE

This application is a continuation of U.S. patent application Ser. No. 16/740,896, filed Jan. 13, 2020, which is a continuation of International Patent Application No. PCT/US2018/042171, filed Jul. 13, 2018, which claims the benefit of U.S. Provisional Application No. 62/532,082, filed Jul. 13, 2017, the entire contents of each of which are incorporated herein by reference.

TECHNICAL FIELD

This relates generally to devices, systems, and methods for performing minimally-invasive operations on a heart, including but not limited to, surgical devices, systems, and methods for performing minimally-invasive operations on the left atrium and internal structures of the heart.

BACKGROUND

Heart disease has been the leading cause of death worldwide. Cardiac operations, such as cardiac surgery, cardiovascular surgery, and cardiothoracic surgery, are important (and sometimes the only available) treatment options for many heart diseases.

Traditionally, for cardiac operations, open heart surgeries were performed. Such operations typically involve cutting and opening the chest of a patient (e.g., via a median sternotomy or a thoracotomy approach). Open heart surgery typically includes making a 5-inch to 10-inch incision in the chest, surgical division of the patient's sternum (also called the breastbone), and also sometimes requires prying the rib cage apart. These procedures can be painful and very invasive, and often lead to medical complications which can slow down the recovery of the patient. In addition, patients who are in poor medical condition may not be eligible to receive open heart surgery due to the risks associated with such operations, thereby preventing the much-needed surgical treatment of heart disease.

SUMMARY

Minimally-invasive heart surgeries have been developed to reduce the above-discussed issues associated with open heart surgery. In minimally-invasive heart surgeries, smaller incisions (e.g., 1-inch to 4-inch incisions) are made on the chest (e.g., a hemisternotomy incision or a mini-thoracotomy incision made at a location that corresponds to spacing between ribs of a patient, such as an intercostal space).

However, current minimally-invasive techniques often require sawing the sternum (e.g., hemisternotomy) or separating the ribs (e.g., right anterior thoracotomy), which often leads to costochondral disarticulation and rib fractures. Minithoracotomy (e.g., right minithoracotomy), which is performed for mitral valve surgeries, involves making an incision on the chest and opening the pericardium. Video-assisted thoracoscopic (VATS) procedures may also involve placing instruments in the chest cavity between the ribs which can be painful. While less invasive than open heart surgery, even these procedures can be associated with significant complications that are undesirable and may not be tolerated by high risk patients. Further, most such approaches require the use of cardiopulmonary bypass to arrest the heart during the procedure, which has risks and complications of its own.

In the past two decades, catheter-based approaches for performing valve repair and replacement and other intracardiac procedures have been developed. These involve the introduction of a catheter into a peripheral artery or vein, and advancement of the catheter into the heart, where a prosthesis may be deployed or a repair procedure performed with the heart beating, avoiding the use of cardiopulmonary bypass. Such approaches have achieved widespread success in aortic valve replacement, where a catheter is introduced from a femoral artery into the aorta and a stented valve prosthesis is deployed at the native aortic valve position. In contrast, however, transcatheter approaches to mitral valve replacement or repair have proven far more difficult. Not only is the anatomy of the mitral valve much more complex than the aortic valve, but the endovascular routes to the mitral valve are circuitous and require navigation through tight turns and across the septum of the heart. Achieving the desired repair or replacement using a long, flexible, tightly-curved catheter has proven extremely challenging. Thus, while some simple transcatheter mitral procedures have gained adoption, more complex transcatheter procedures such as mitral replacement, annuloplasty, and chordal replacement are still far away from clinical viability.

In recent years, some surgeons have employed a transapical approach to perform mitral valve surgery on the beating heart, which, like transcatheter approaches, can eliminate the need for cardiopulmonary bypass. In this approach, a left mini-thoracotomy is created and an opening is made in the pericardium. An incision is made in the left ventricle of the heart near the apex to create a sealed access port through which instruments and/or prostheses can be introduced to perform mitral valve repair or replacement. While the trans-apical approach has the advantage of avoiding cardiopulmonary bypass and further allows the mitral valve to be reached through a much shorter, straighter path than endovascular approaches, it has been found that access through the left ventricle creates significant trauma to this critical muscular chamber of the heart and can result in long-term impairment of ejection fraction and/or can cause scar tissue formation in the heart muscle. Further, controlling bleeding from the trans-apical incision is challenging both during and after the procedure and the occurrence of bleeding-related complications has been undesirably high. Moreover, this approach requires pericardial access which adds risk and complexity. Therefore many surgeons believe that the trans-apical approach is not a long-term solution for less-invasive mitral surgery.

Thus, there is a need for systems, methods, and devices that further reduce or eliminate complications associated with cutting, separating, and/or breaking the bones, incising the diaphragm, and/or incising the pericardium, which avoid incisions in the left ventricle, and which allow intra-cardiac surgery to be performed on the beating heart without the need for cardiopulmonary bypass.

Some or all of the above deficiencies and other problems associated with conventional surgical devices and methods may be reduced or eliminated by the disclosed devices and methods.

In accordance with some embodiments, a method includes inserting at least a portion of a first instrument through a first opening in a neck superior to a sternum of the patient; advancing the first instrument toward a heart of the patient; and making a second opening through a left atrial wall of the heart without penetrating a pericardium. The second opening is configured to receive at least a second instrument to perform one or more cardiac procedures within the heart.

In accordance with some embodiments, the first opening may be in or adjacent to the suprasternal notch of the patient.

In accordance with some embodiments, the first and second instruments may be inserted through the first opening without cutting a sternum or a rib of the patient.

In accordance with some embodiments, the heart may remain beating during the steps of inserting, advancing, and making.

In accordance with some embodiments, advancing the first instrument toward the heart of the patient may include advancing the first instrument through a mediastinal space toward the heart of the patient. Alternatively or in combination, advancing the first instrument toward the heart of the patient may include advancing the first instrument along a first path that is along an anterior portion of a trachea of the patient.

In accordance with some embodiments, at least the portion of the first instrument may be advanced along a second path toward the cardiac wall of the heart subsequent to advancing the first instrument along the first path.

In accordance with some embodiments, the second opening may be made into a left atrial chamber of the heart. The second opening may be made in a roof or dome of the left atrium of the heart. Alternatively or in combination, the second opening may be made in a space on a left atrial wall in a space between at least two pulmonary vein ostia. Alternatively or in combination, the second opening is made in the left atrial wall in a space between four pulmonary venous ostia.

In accordance with some embodiments, the second opening may be made through the cardiac wall of the heart without entering a pericardial space around the heart. In accordance with some embodiments, the second opening through the cardiac wall of the heart may be made without cutting, making an incision on, or removing any portion of a pericardium of the heart In accordance with some embodiments, the method may further comprise determining whether the first instrument has reached the cardiac wall of the heart. The method may include determining that the first instrument has reached the cardiac wall; and in response to determining that the first instrument has reached the cardiac wall of the heart, making the second opening through the cardiac wall of the heart. Determining that the first instrument has reached the cardiac wall of the heart may comprise directly viewing the wall of the heart through the first opening. Alternatively or in combination, determining that the first instrument has reached the cardiac wall of the heart may comprise directly viewing the wall of the heart through the first opening without the use of an endoscopic visualization device In accordance with some embodiments, the method may further comprise making the second opening through the cardiac wall of the heart using the first instrument; and subsequent to making the second opening, inserting the first instrument through the second opening to perform the one or more cardiac procedures.

In accordance with some embodiments, the method may further comprise making the second opening through the cardiac wall of the heart using the first instrument; and subsequent to making the second opening, inserting a second instrument that is distinct from the first instrument, through the second opening for the one or more cardiac procedures.

In accordance with some embodiments, the method may further comprise sealing or compressing tissue around a respective instrument inserted through the second opening to inhibit blood loss from the heart.

In accordance with some embodiments, the method may further comprise delivering a gas to the patient's chest cavity prior to inserting the respective instrument through the first opening. The gas may optionally comprise carbon dioxide.

In accordance with some embodiments, the method may further comprise prior to making the second opening through the cardiac wall of the heart, slowing down the patient's heart rate and/or reducing the patient's blood pressure.

In accordance with some embodiments, the method may further comprise prior to making the second opening through the cardiac wall of the heart, temporarily stopping the patient's heart.

In accordance with some embodiments, the one or more cardiac procedures may include one or more surgical procedures. The one or more cardiac procedures may include one or more minimally-invasive procedures. The one or more cardiac procedures may include mitral valve surgery. Alternatively or in combination, the one or more cardiac procedures may include mitral valve replacement. Alternatively or in combination, the one or more cardiac procedures may include mitral valve repair.

In accordance with some embodiments, the method may further comprise performing a respective cardiac procedure of the one or more cardiac procedures. Subsequent to performing the respective cardiac procedure, the second opening may be closed. Alternatively or in combination, the first instrument may be removed from the first opening.

In accordance with some embodiments, a method includes inserting a first instrument through a first opening of a patient; advancing the first instrument toward a roof or dome of the left atrium of a heart of the patient; and making a second opening through a cardiac wall in an extrapericardial location on the roof or dome of the left atrium of the heart for one or more cardiac procedures.

In accordance with some embodiments, a method comprises inserting a first instrument through a first opening of a patient; advancing the first instrument toward a heart of the patient; and performing one or more cardiac procedures. The one or more cardiac procedures may include clipping a left atrial appendage of the patient. Alternatively or in combination, the method may further comprise accessing a pericardium of the patient.

In accordance with some embodiments, a surgical instrument includes means for inserting at least a portion of a first instrument through a first opening in or adjacent to a suprasternal notch of a patient; means for advancing the first instrument toward a heart of the patient; and means for making a second opening in an extrapericardial location on a cardiac wall of the heart for one or more cardiac procedures.

In accordance with some embodiments, a surgical instrument includes means for, subsequent to inserting at least a portion of a first instrument through a first opening adjacent to a suprasternal notch of a patient and advancing the first instrument toward a heart of the patient, making a second opening through a cardiac wall of the heart for one or more cardiac procedures.

In accordance with some embodiments, a surgical instrument includes means for inserting the first instrument through a first opening of a patient; means for advancing the first instrument toward a roof or dome of a left atrium of a heart of the patient; and means for making a second opening through an extrapericardial location on a cardiac wall in or adjacent to the dome of the left atrium of the heart for one or more cardiac procedures.

In accordance with some embodiments, a surgical instrument includes means for, subsequent to inserting at least a portion of a first instrument through a first opening and advancing the first instrument toward a heart of the patient, making a second opening through a cardiac wall of the heart for one or more cardiac procedures.

In accordance with some embodiments, a surgical instrument includes an incision device configured for making an opening through a cardiac wall of a heart of a patient, wherein the incision device is configured for insertion through a first opening adjacent to a suprasternal notch of a patient and extension from the first opening to the heart of the patient. The surgical instrument may further comprise means for positioning the incision device adjacent to the roof or dome of a left atrium of the heart of the patient. Alternatively or in combination, the surgical instrument may include a hollow shell configured for advancing the incision device from the first opening adjacent to the suprasternal notice of the patient toward the heart of the patient. The hollow shell may include a tube.

In accordance with some embodiments, a surgical instrument includes means for performing any of the methods described herein.

In accordance with some embodiments, a surgical instrument includes means for inserting the first instrument through the first opening of the patient; means for advancing the first instrument toward a heart of the patient; and means for performing one or more cardiac procedures.

In accordance with some embodiments, a surgical instrument kit includes means for inserting at least a portion of a first instrument through a first opening in or adjacent to a suprasternal notch of a patient; means for advancing the first instrument toward a heart of the patient; and means for making a second opening through a cardiac wall of the heart for one or more cardiac procedures.

In accordance with some embodiments, a surgical instrument kit comprises means for inserting at least a portion of a first instrument through a first opening in or adjacent to a suprasternal notch of a patient; means for advancing the first instrument toward a heart of the patient; and means for inserting the first instrument through a second opening in an extrapericardial location on a cardiac wall of the heart for one or more cardiac procedures.

In accordance with some embodiments, a surgical instrument kit includes means for inserting a first instrument through a first opening of a patient; means for advancing the first instrument toward the roof or dome of the left atrium of a heart of the patient; and means for making a second opening in an extrapericardial location on a cardiac wall of the roof or dome of the left atrium of the heart for one or more cardiac procedures.

In accordance with some embodiments, a surgical instrument kit includes means for performing any of the methods described herein. The surgical instrument kit may optionally comprise the first instrument. Alternatively or in combination, the surgical instrument kit may include the second instrument. Alternatively or in combination, the surgical instrument kit may optionally comprise a clip configured for clipping a left atrial appendage of the patient.

In accordance with some embodiments, a surgical instrument kit includes any surgical instrument described herein.

In accordance with some embodiments, a method comprises inserting a distal portion of a surgical instrument into a body of a patient through an opening in a suprasternal notch of the patient, advancing the distal portion of the surgical instrument along a trachea of the patient toward a left atrium of a heart of the patient, making an extrapericardial penetration through a cardiac wall at a first location on a dome of the left atrium of the patient, wherein the first location is outside a pericardium of the heart, advancing the distal portion of the surgical instrument through the extrapericardial penetration in the dome of the left atrium to access an internal chamber of the heart, while a proximal portion of the surgical instrument remains outside the body of the patient, inserting a procedural instrument through a channel in the surgical instrument into the internal chamber of the heart, and performing a surgical procedure in the internal chamber of the heart with the procedural instrument.

In accordance with some embodiments, the method may further comprise making the opening in the suprasternal notch of the patient by making an incision adjacent the suprasternal notch of the patient. The incision may be made without cutting any portion of a sternum or any ribs of the patient.

In accordance with some embodiments, advancing the distal portion toward the heart may comprise advancing the distal portion of the surgical instrument through a mediastinal space of the body.

In accordance with some embodiments, advancing the distal portion toward the heart may comprise advancing the distal portion of the surgical instrument along a path anterior to the trachea. The path may extend through a space between the trachea and an ascending aorta, or a space between the trachea and an arch of the aorta. Alternatively or in combination, the path may extend through a space between the trachea and a right branch of a pulmonary artery. Alternatively or in combination, the path may extend through a space between the trachea and a left branch of a pulmonary artery. Alternatively or in combination, the path may extend through a space between the trachea and a bifurcation of a main pulmonary artery. Alternatively or in combination, the path may be substantially parallel to a plane containing a longitudinal axis of the trachea. Alternatively or in combination, the path may be substantially parallel to a plane defined by a primary bronchus.

In accordance with some embodiments, advancing the distal portion toward the heart may comprise steering the distal portion of the surgical instrument to avoid internal structures of the patient. The internal structures of the patient may comprise a pulmonary artery or a primary bronchus of the patient.

In accordance with some embodiments, inserting the distal portion of the surgical instrument through the opening may comprise inserting the distal portion of the surgical instrument into a working channel of a mediastinoscope placed in the opening. Advancing the distal portion may comprise advancing the distal portion of the surgical instrument through the working channel.

In accordance with some embodiments, the surgical instrument may comprise a cannula having a channel and a trocar disposed in the channel. Making the extrapericardial penetration may comprise making an extrapericardial penetration with the trocar. Optionally, the method may further comprise removing the trocar from the channel after advancing the distal portion of the surgical instrument through the extrapericardial penetration.

In accordance with some embodiments, making the extrapericardial penetration may comprise making an incision through the cardiac wall at the first location without penetrating the pericardium of the heart.

In accordance with some embodiments, the method may further comprise contacting the left atrium of the heart with the distal portion of the surgical instrument prior to making the extrapericardial penetration.

In accordance with some embodiments, the method may further comprise sealing the cardiac wall of the extrapericardial penetration and the distal portion of the surgical instrument. Sealing the cardiac wall of the extrapericardial penetration and the distal portion of the surgical instrument may comprise tightening a pursestring suture in the cardiac wall around the extrapericardial penetration around the distal portion of the surgical instrument. Alternatively or in combination, sealing the cardiac wall of the extrapericardial penetration and the distal portion of the surgical instrument may comprise sealing comprises expanding a sealing element coupled to a distal end of the surgical instrument. The sealing element may optionally comprise a compression flange or a balloon.

In accordance with some embodiments, the method may further comprise preventing inadvertent removal of the surgical instrument through the extrapericardial penetration. Preventing inadvertent removal may comprise positioning a retention element coupled to the distal portion of the surgical instrument in the left atrium. The retention element may optionally comprise a flange, an expandable mechanical element, or a balloon. The method may optionally further comprise deploying the retention element from an undeployed configuration to a deployed configuration. Alternatively or in combination, preventing inadvertent removal may comprise applying negative pressure to the cardiac wall via a suction port. In accordance with some embodiments, the surgical instrument may comprise an external cannula having a suction port and an internal cannula within the external cannula. Advancing the distal portion of the surgical instrument through the extrapericardial penetration may comprise advancing the internal cannula through the extrapericardial penetration while the external cannula remains in contact with the cardiac wall outside the extrapericardial penetration. Alternatively or in combination, preventing inadvertent removal may comprise anchoring the proximal portion of the surgical instrument.

In accordance with some embodiments, the method may further comprise visualizing the heart of the patient while advancing the distal portion of the surgical instrument toward the heart. Visualizing may comprise directly viewing the heart through the opening or through a scope. Visualizing may optionally comprise directly viewing the heart with the naked eye through the opening or through the scope. Alternatively or in combination, visualizing may comprise viewing the heart with a mediastinoscope, a camera coupled to the distal portion of the surgical instrument, an optical channel in the surgical instrument, or an endoscope placed through the opening.

In accordance with some embodiments, the method may further comprise visualizing the internal chamber of the heart after advancing the distal portion of the surgical instrument through the extrapericardial penetration. Visualizing may comprise imaging the internal chamber of the heart with a camera coupled to the distal portion of the surgical instrument, an optical channel in the surgical instrument, or an endoscope placed through the opening. Alternatively or in combination, visualizing may comprise advancing an endoscope through a channel of the surgical instrument into the internal chamber of the heart, and displacing blood from a distal end of the endoscope to facilitate viewing intracardiac structures.

In accordance with some embodiments, the method may further comprise removing the distal portion of the surgical instrument from the heart and closing the extrapericardial penetration after removing the distal portion of the surgical instrument from the heart. Optionally, the method may further comprise placing a pursestring suture in the cardiac wall around the extrapericardial penetration. Closing the extrapericardial penetration may comprise cinching the pursetring suture. Alternatively or in combination, the method may further comprise advancing a suturing device through a channel in the surgical instrument and placing one or more sutures in the cardiac wall around the extrapericardial penetration with the suturing device. Closing the extrapericardial penetration may comprise tightening or knotting the one or more sutures. Alternatively or in combination, the method may further comprise placing one or more sutures in the cardiac wall around the extrapericardial penetration with the surgical instrument. Closing the extrapericardial penetration may comprise tightening or knotting the one or more sutures.

In accordance with some embodiments, the method may further comprise removing the distal portion of the surgical instrument from the opening adjacent the suprasternal notch of the patient and closing the opening after removing the distal portion of the surgical instrument from the opening.

In accordance with some embodiments, the surgical procedure may be performed on a beating heart.

In accordance with some embodiments, the method may further comprise placing a temporary pacing lead in the heart to pace the heart during the surgical procedure.

In accordance with some embodiments, the surgical procedure may comprise at least one of mitral valve replacement, mitral valve repair, mitral annuloplasty, chordal repair, chordal replacement, leaflet resection, or leaflet coaptation.

In accordance with some embodiments, the surgical procedure may comprise at least one of atrial appendage closure, atrial ablation, pulmonary vein ablation, septal defect closure, aortic valve repair, aortic valve replacement, tricuspid valve repair, tricuspid valve replacement, implantable cardiac defibrillator (ICD) implantation, pacemaker implantation, or placement of leads for ICD's or pacemakers, myocardial biopsy, or septectomy.

In accordance with some embodiments, the surgical procedure may comprise mitral annuloplasty. Performing the surgical procedure may comprise (i) applying one or more sutures in a mitral annulus of the heart with the procedural instrument, the one or more sutures having distal ends extending outside the body through the channel, (ii) advancing an annuloplasty ring through the channel to the mitral valve, and (iii) securing the annuloplasty ring to the mitral annulus with the one or more sutures. The heart may be beating during the surgical procedure.

In accordance with some embodiments, the surgical procedure may comprise chordal repair or chordal replacement. Performing the surgical procedure may comprise (i) coupling one or more prosthetic chords between at least one of a mitral leaflet of the heart and a papillary muscle of the heart using the procedural instrument to form one or more artificial chordae tendineae therebetween. The heart may be beating during the surgical procedure.

In accordance with some embodiments, the surgical procedure may be performed with the procedural instrument extending through the opening and coupled to a robotic manipulator disposed outside or inside a chest of the patient.

In accordance with some embodiments, the extrapericardial penetration may be made while the heart is beating. The method may further comprise sealing the extrapericardial penetration around the surgical instrument to inhibit leakage of blood while the heart is beating.

In accordance with some embodiments, a surgical instrument comprises an elongate member having a distal portion configured to be inserted into a body of a patient and a proximal portion configured to remain outside the body of the patient when the distal portion is inserted into the body of the patient. The elongate member comprises an inner wall defining a channel therein, the channel extending between a distal end and a proximal end of the elongate member and being configured to receive a procedural instrument for performing a surgical procedure. The distal portion of the elongate member is configured to extend from a suprasternal notch of the patient and through an extrapericardial penetration through a cardiac wall at a first location on a dome of a left atrium of the patient to access an internal chamber of the heart, the first location being outside a pericardium of the heart.

In accordance with some embodiments, the distal portion of the elongate member may be configured to be advanced toward the heart thorough a mediastinal space of the body.

In accordance with some embodiments, the distal portion of the elongate member may be configured to be advanced toward the heart along a path anterior to the trachea. The path may extend from the opening adjacent the suprasternal notch, through a space between the trachea and an ascending aorta or an aortic arch, through a space between the trachea and a branch of a pulmonary artery, and to the left atrium of the heart of the patient. Alternatively or in combination, the path may be substantially parallel to a plane containing a longitudinal axis of the trachea. Alternatively or in combination, the path may be substantially parallel to a plane defined by a primary bronchus.

In accordance with some embodiments, the elongate member may comprise a cannula, a sheath, a tube, or a hollow shell.

In accordance with some embodiments, the elongate member may comprise have an outer diameter within a range of about 5 mm to about 30 mm.

In accordance with some embodiments, the elongate member may have a length within a range of about 5 cm to about 32 cm from the proximal end to the distal end.

In accordance with some embodiments, the elongate member may be rigid. Alternatively or combination, at least a portion of the elongate member may be flexible. Alternatively or in combination, at least a portion of the elongate member may be articulated.

In accordance with some embodiments, the channel may be substantially straight from the proximal portion to the distal portion.

In accordance with some embodiments, the elongate member may be configured to fit within a working channel of a mediastinoscope.

In accordance with some embodiments, the surgical instrument may further comprise a trocar removably disposed within the channel of the elongate member. The trocar may be configured to make the extrapericardial penetration. Optionally, the trocar may be configured to make the extrapericardial penetration without penetrating the pericardium of the heart.

In accordance with some embodiments, the distal portion of the elongate member may be configured to be advanced through the extrapericardial penetration without penetrating the pericardium of the heart.

In accordance with some embodiments, the distal portion of the elongate member may be configured to contact the cardiac wall on the dome of the left atrium with the proximal portion extending out of the opening.

In accordance with some embodiments, the surgical instrument may further comprise a retention element coupled to the distal portion of the elongate member. The retention element may be configured to resist inadvertent removal of the elongate member from a cardiac wall of the patient. The retention element may comprise a flange, an expandable wire structure, or a balloon. The retention element may optionally have an undeployed configuration and a deployed configuration. The retention element may be configured to form a hemostatic seal around the distal portion of the elongate member when actuated from the undeployed configuration to the deployed configuration after the elongate member is advanced through the extrapericardial penetration into the internal chamber of the heart.

In accordance with some embodiments, the elongate member may comprise an external cannula and an internal cannula disposed therein. The inner wall defining the channel may comprise an inner wall of the internal cannula. A distal portion of the internal cannula may be configured to be advanced from a distal end of the external cannula through the extrapericardial penetration. The distal end of the external cannula may be configured to remain in contact the cardiac wall outside the extrapericardial penetration.

In accordance with some embodiments, the surgical instrument may further comprise a plurality of needles coupled to the internal cannula. The plurality of needles may be movable from a delivery position to a deployed position. In the deployed position, the plurality of needles may be configured to be pushed through the cardiac wall and captured by a capture device coupled to the external cannula.

Alternatively or in combination, the surgical instrument may further comprise a retention element coupled to the distal portion of the elongate member. The retention element may have an undeployed configuration and a deployed configuration. The retention element may be configured to resist inadvertent removal of the elongate member from a cardiac wall of the patient. In accordance with some embodiments, the retention element may comprise a suction port in the external cannula configured to seal a distal end of the external cannula against the cardiac wall when negative pressure is applied to the cardiac wall via the suction port. Alternatively or in combination, the retention element may comprise a balloon on the distal portion of the internal cannula configured to engage an internal portion of the cardiac wall. The surgical instrument may optionally further comprise a conforming pad coupled to the distal end of the external cannula configured to stabilize the cardiac wall between the conforming pad and the balloon when the balloon is inflated into the deployed configuration.

Alternatively or in combination, the surgical instrument may further comprise a closure device comprising a plurality of needles having an undeployed configuration and a deployed configuration. The closure device may be configured to be inserted into the internal chamber of the heart through the lumen of the internal cannula when the plurality of needles are in the undeployed configuration. The plurality of needles may be configured to be pushed through the cardiac wall into a capture device coupled to the distal end of the external cannula when the closure device is retracted towards the internal cannula. Retraction of the closure device may be configured to pull the plurality of needles and a plurality of sutures coupled thereto through the cardiac wall.

In accordance with some embodiments, the surgical instrument may further comprise a sealing element coupled to the distal end of the elongate member, the sealing element being configured to be actuated from an undeployed configuration to a deployed configuration to form a hemostatic seal around the distal portion of the elongate member when the elongate member is advanced through the extrapericardial penetration into the internal chamber of the heart. Optionally, the sealing element may comprise a compression flange or a balloon.

In accordance with some embodiments, the surgical instrument may further comprise a hemostatic valve disposed in the channel to inhibit blood loss. The hemostatic valve may comprise a duckbill valve or a three leaflet valve.

In accordance with some embodiments, the surgical instrument may further comprise an anchoring element coupled to the proximal portion of the elongate member.

In accordance with some embodiments, the surgical instrument may further comprise a visualization element coupled to the elongate member. The visualization element may comprise a CCD or CMOS or video chip coupled to the distal portion of the elongate member. Alternatively or in combination, the visualization element may comprise an optical channel extending through the elongate member and a lens aligned with the optical channel. The surgical instrument may further comprise an eyepiece or camera coupling optically coupled to a proximal end of the optical channel and configured to allow direct visualization of internal structures of the body. Alternatively or in combination, the surgical instrument may further comprise a blood displacement element coupled to a distal end of the optical channel and configured to displace blood from the distal end of the optical channel. The blood displacement element may comprise an enlarged optically transparent cylindrical, spherical, bullet-shaped, cone-shaped, or dome-shaped member, or a balloon. Alternatively or in combination, the blood displacement element may comprise a fluid delivery channel extending through the elongate member adjacent the optical channel such that injection of a fluid displaces blood adjacent the distal end of the optical channel.

In accordance with some embodiments, a system comprises any of the surgical instruments described herein and a visualization device or procedural instrument configured for insertion into the internal chamber of the heart through the channel of the elongate member.

In accordance with some embodiments, the visualization device may comprise a mediastinoscope or an endoscope. The endoscope may be configured to be inserted into the internal chamber of the heart through the channel of the elongate member.

In accordance with some embodiments, the procedural device may be configured to perform a surgical procedure in the internal chamber of the heart. The surgical procedure may comprise at least one of mitral valve replacement, mitral valve repair, mitral annuloplasty, chordal repair, chordal replacement, leaflet resection, mitral replacement, or leaflet coaptation. Alternatively or in combination, the surgical procedure may comprise at least one of atrial appendage closure, atrial ablation, pulmonary vein ablation, septal defect closure, aortic valve repair, aortic valve replacement, tricuspid valve repair, tricuspid valve replacement, implantable cardiac defibrillator (ICD) implantation, pacemaker implantation, or placement of leads for ICD's or pacemakers, myocardial biopsy, or septectomy.

In accordance with some embodiments, the surgical procedure may comprise mitral annuloplasty and the procedural instrument may be configured to apply one or more sutures to an annulus of a mitral valve of the heart, the one or more sutures having free ends configured to extend outside the body through the channel. The system may further comprise an annuloplasty ring configured to be coupled to the one or more sutures. The annuloplasty ring may be configured to be advanced through the channel to the mitral valve and secured to the mitral valve by the one or more sutures.

In accordance with some embodiments, the surgical procedure may comprise chordal repair or chordal replacement and the procedural instrument may be configured to couple one or more prosthetic chords to at least one of a mitral leaflet of the patient and a papillary muscle of the patient to form one or more artificial chordae tendineae therebetween.

In accordance with some embodiments, the surgical procedure may comprise mitral valve replacement and the procedural instrument may be configured to deliver a prosthetic mitral valve through the channel. The system may further comprise a prosthetic mitral valve. The prosthetic mitral valve may be configured to be advanced through the channel in a collapsed configuration and deployed into an expanded configuration at the native mitral valve.

In accordance with some embodiments, a surgical system comprises an access device comprising an elongate member having a distal portion configured to be inserted into a body of a patient and a proximal portion configured to remain outside the body of the patient when the distal portion is inserted into the body of the patient, the elongate member comprising an inner wall defining a channel therein, the channel extending between a distal end and a proximal end of the elongate member, and a procedural device configured to be advanced through the channel of the elongate member into the internal chamber of the heart and configured to perform a surgical procedure in the heart. The distal portion of the elongate member is configured to extend from an opening in or adjacent a suprasternal notch of the patient and through an extrapericardial penetration through a cardiac wall at a first location on a dome of the left atrium of the patient to access an internal chamber of the heart, the first location being outside a pericardium of the heart In accordance with some embodiments, the surgical procedure may comprise at least one of mitral valve replacement, mitral valve repair, mitral annuloplasty, chordal repair, chordal replacement, leaflet resection, mitral replacement, or leaflet coaptation.

In accordance with some embodiments, the surgical procedure may comprise at least one of atrial appendage closure, atrial ablation, pulmonary vein ablation, septal defect closure, aortic valve repair, aortic valve replacement, tricuspid valve repair, tricuspid valve replacement, implantable cardiac defibrillator (ICD) implantation, pacemaker implantation, or placement of leads for ICD's or pacemakers, myocardial biopsy, or septectomy.

In accordance with some embodiments, the surgical procedure may comprise mitral annuloplasty and the procedural device may be configured to apply one or more sutures to an annulus of a mitral valve of the heart, the one or more sutures having free ends configured to extend outside the body through the channel. The surgical system may further comprise an annuloplasty ring configured to be coupled to the one or more sutures. The annuloplasty ring may be configured to be advanced through the channel to the mitral valve and secured to the mitral valve by the one or more sutures.

In accordance with some embodiments, the surgical procedure may comprise chordal repair or chordal replacement and the procedural instrument may be configured to couple one or more prosthetic chords to at least one of a mitral leaflet of the patient and a papillary muscle of the patient to form one or more artificial chordae tendineae therebetween.

In accordance with some embodiments, the surgical procedure may comprise mitral valve replacement and wherein the procedural instrument may be configured to delivery a prosthetic mitral valve through the channel. The surgical system may further comprise a prosthetic mitral valve configured to be advanced through the channel in a collapsed configuration and deployed into an expanded configuration at the native mitral valve.

In accordance with some embodiments, a system comprises a suprasternal access device having a distal portion configured to be inserted into a body of a patient, a proximal portion configured to remain outside the body of the patient when the distal portion is inserted into the body of the patient, and a working channel extending between a distal end and a proximal end of the suprasternal access device, and an intracardiac access device positionable through the working channel of the suprasternal access device. The distal portion of the suprasternal access device is configured to extend from an opening in or adjacent a suprasternal notch of the patient and into a mediastinum of the patient. A distal portion of the intracardiac access device is configured to extend from the distal portion of the suprasternal access device and through an extrapericardial penetration through a cardiac wall at a first location on a dome of the left atrium of the patient to access an internal chamber of the heart, the first location being outside a pericardium of the heart.

In accordance with some embodiments, the suprasternal access device may comprise a mediastinoscope.

In accordance with some embodiments, the suprasternal access device may be rigid.

In accordance with some embodiments, the proximal portion of the suprasternal access device may be configured to prevent insertion of the proximal portion of the suprasternal access device into the opening.

In accordance with some embodiments, the proximal portion of the suprasternal access device may comprise an anchoring element configured to prevent one or both of (i) inadvertent removal of the suprasternal access device from the opening or (ii) inadvertent advancement toward the heart beyond a desired distance.

In accordance with some embodiments, the distal portion of the suprasternal access device may be configured to be positioned within a range of about 0 cm to 2 cm above the first location.

In accordance with some embodiments, the distal portion of the suprasternal access device may have a length of about 15 cm to about 20 cm.

In accordance with some embodiments, the suprasternal access device may comprise a visualization element. The visualization element may comprise one or more of a CCD chip, a CMOS chip, a video chip, an ultrasound transducer, an optical channel, a lens, a fiber optic light cable, a light emitting diode (LED), or an illumination element.

In accordance with some embodiments, the proximal portion of the suprasternal access device may comprise a retention element configured to couple the intracardiac access device to the suprasternal access device and restrict relative movement.

In accordance with some embodiments, a distal tip of the intracardiac access device may be steerable to an oblique angle relative to a proximal portion of the intracardiac access device.

In accordance with some embodiments, the distal portion of the intracardiac access device may have a length extending from the opening in or adjacent a suprasternal notch of the patient and through the extrapericardial penetration into the internal chamber of the heart.

In accordance with some embodiments, a distal end of the intracardiac access device may comprise a retention element.

In accordance with some embodiments, the intracardiac device may comprise an elongate member having a distal portion configured to be inserted into a body of a patient through the working channel of the suprasternal access device and a proximal portion configured to remain outside the body of the patient when the distal portion is inserted into the body of the patient. The elongate member may comprise an inner wall defining a channel therein. The channel may extend between a distal end and a proximal end of the elongate member. The channel may be configured to receive a procedural instrument for performing a surgical procedure.

In accordance with some embodiments, the intracardiac device may comprise a retention element coupled to the distal portion of the intracardiac device. The retention element may have an undeployed configuration and a deployed configuration. The retention element may be configured to resist inadvertent removal of the intracardiac device from a cardiac wall of the patient.

In accordance with some embodiments, the intracardiac device may comprise a sealing element coupled to the distal end of the intracardiac device. The sealing element may be configured to be actuated from an undeployed configuration to a deployed configuration to form a hemostatic seal around the distal portion of the intracardiac device when the intracardiac device is advanced through the extrapericardial penetration into the internal chamber of the heart.

In accordance with some embodiments, the suprasternal access device may comprise an insufflation channel or insufflation port configured to insufflate a chest cavity of the patient with a gas directed therethrough.

In accordance with some embodiments, a system comprises an intracardiac access device having a distal portion configured to be inserted into a body of a patient, a proximal portion configured to remain outside the body of the patient when the distal portion is inserted into the body of the patient, and a channel extending between a distal end and a proximal end of the intracardiac access device, and a procedural device positionable through the channel of the intracardiac access device. The distal portion of the intracardiac access device is configured to extend from an opening in or adjacent a suprasternal notch of the patient and through an extrapericardial penetration through a cardiac wall at a first location on a dome of the left atrium of the patient to access an internal chamber of the heart, the first location being outside a pericardium of the heart.

In accordance with some embodiments, the intracardiac access device may be substantially rigid and straight.

In accordance with some embodiments, the intracardiac access device may comprise an internal sealing element configured to inhibit blood loss through the channel of the intracardiac access device.

In accordance with some embodiments, the intracardiac access device may be configured to extend through the extrapericardial penetration in the cardiac wall without penetrating the pericardium of the heart.

In accordance with some embodiments, the intracardiac access device may comprise a pre-formed shape or curve.

In accordance with some embodiments, the intracardiac access device may have a steerable tip.

In accordance with some embodiments, a distal tip of the intracardiac access device may be configured to be positioned generally orthogonal to a plane containing an annulus of a mitral valve of the heart.

In accordance with some embodiments, the procedural device may comprise an annuloplasty band or annuloplasty ring.

In accordance with some embodiments, the procedural device may be configured to attach an annuloplasty device to a mitral annulus of the heart.

In accordance with some embodiments, the procedural device may be configured to attach prosthetic chord to a mitral leaflet of the heart.

In accordance with some embodiments, the procedural device may be configured to apply a suture to heart tissue on or near a mitral valve of the heart.

In accordance with some embodiments, the system may further comprise a visualization element configured to permit direct visualization of the internal chamber of the heart through blood. The visualization element may comprise a blood displacement element. Alternatively or in combination, the visualization element and the procedural device may be configured to be simultaneously positioned in the channel of the intracardiac access device. Alternatively or in combination, the visualization element may be configured to be positioned within the channel of the intracardiac access device independently of the procedural device. Alternatively or in combination, the visualization element may comprise an optical channel and a lens. Alternatively or in combination, the visualization element may comprise a CCD chip.

In accordance with some embodiments, a kit comprises any of the systems described herein sealed in a sterilized package.

Thus, the disclosed devices and methods reduce or eliminate the deficiencies and other problems associated with conventional heart surgery techniques, thereby facilitating fast patient recovery, shorter hospital stay, reduced postoperative pain, reduced infection, and/or other medical complications, or any combination thereof. The disclosed devices, systems, and methods optionally complement or replace conventional devices and methods for cardiac operations.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosures are set forth with particularity in the appended claims. For a better understanding of the features and advantages of the various described implementations, in which the principles of the present disclosure are utilized, reference should be made to the Detailed Description below, in conjunction with the following drawings in which like reference numerals refer to corresponding parts throughout the figures.

FIGS. 4A-4F illustrate delivery of a surgical instrument, in accordance with some embodiments.

FIGS. 16A-16E show another exemplary closure device, in accordance with some embodiments.

Like reference numerals refer to corresponding parts throughout the several views of the drawings. Drawings are not necessarily drawn to scale unless explicitly indicated otherwise.

DETAILED DESCRIPTION

Reference will now be made in detail to implementations, examples of which are illustrated in the accompanying drawings. In the following detailed description, numerous specific details are set forth in order to provide a thorough understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Many modifications and variations of this disclosure can be made without departing from its spirit and scope, as will be apparent to those skilled in the art. The specific implementations described herein are offered by way of example only, and the disclosure is to be limited only by the terms of the appended claims, along with the full scope of equivalents to which such claims are entitled. It will be readily understood that the aspects of the present disclosure, as generally described herein, and illustrated in the figures, can be arranged, substituted, combined, separated, and designed in a wide variety of different configurations, all of which are explicitly contemplated herein.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments, however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Figure 1:
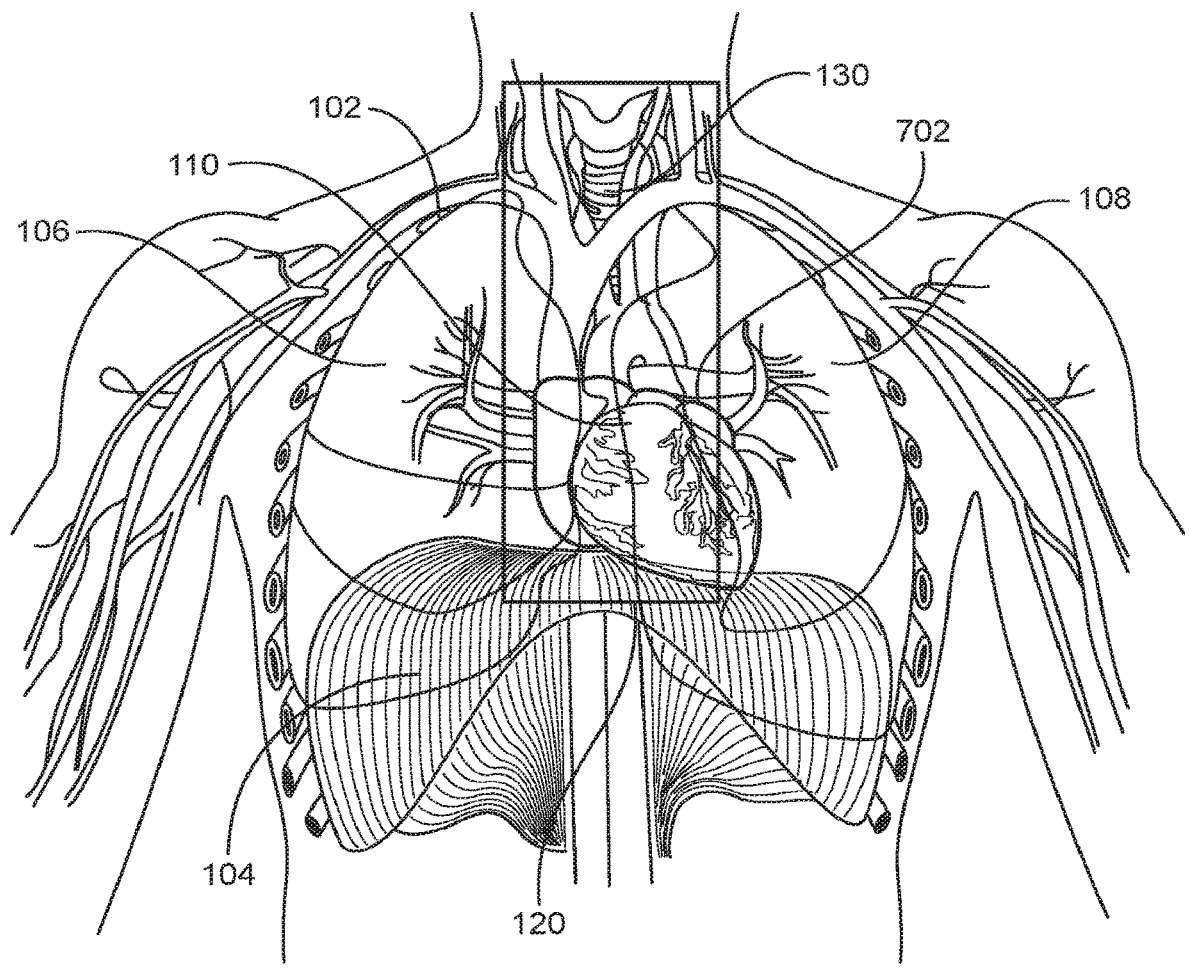
FIG. 1 is a schematic diagram illustrating a location for making an incision, in accordance with some embodiments.

FIG. 1 is a schematic diagram illustrating an example thoracic cavity. A thoracic cavity (also called a chest cavity) is a chamber of a body of a patient that is surrounded by a rib cage 102 and has a thoracic diaphragm 104 at the bottom. Multiple vital organs, such as lungs 106, 108 and the heart 110, are located within the thoracic cavity. Because the breast bone (i.e. sternum, see e.g. FIG. 6), rib cage 102, and the thoracic diaphragm 104 protect the thoracic cavity, conventional heart surgery techniques require cutting, removing, and/or separating one or more portions of the sternum, rib cage 102, and/or the thoracic diaphragm 104 to gain access to the heart 110 (e.g., for delivery of surgical instruments to the heart).

The mediastinum 120 is a central compartment of the thoracic cavity. As shown in FIG. 1, the mediastinum 120 is located between the lungs 106, 108, and a heart 110 and trachea 130 are located within the mediastinum 120 (e.g., in the middle mediastinum). In some embodiments, the middle mediastinum 120 is accessed through the superior mediastinum (e.g., a portion of the mediastinum from the thoracic inlet to the area above the line from the sterno-manubrial junction to the $4^{th}$ thoracic vertebra). The mediastinum 120 may be located between the left and right pleural cavities surround the right and left lungs 106, 108, respectively.

In some embodiments, the mediastinum 120 (e.g., the middle mediastinum) is accessed through the superior thoracic aperture (see e.g. FIG. 2), thereby eliminating the need for cutting, removing, or separating one or more portions of the sternum (see e.g. FIG. 6), the rib cage 102 and/or the thoracic diaphragm 104. This, in turn, reduces or eliminates the problems associated with such procedures.

Figure 2:
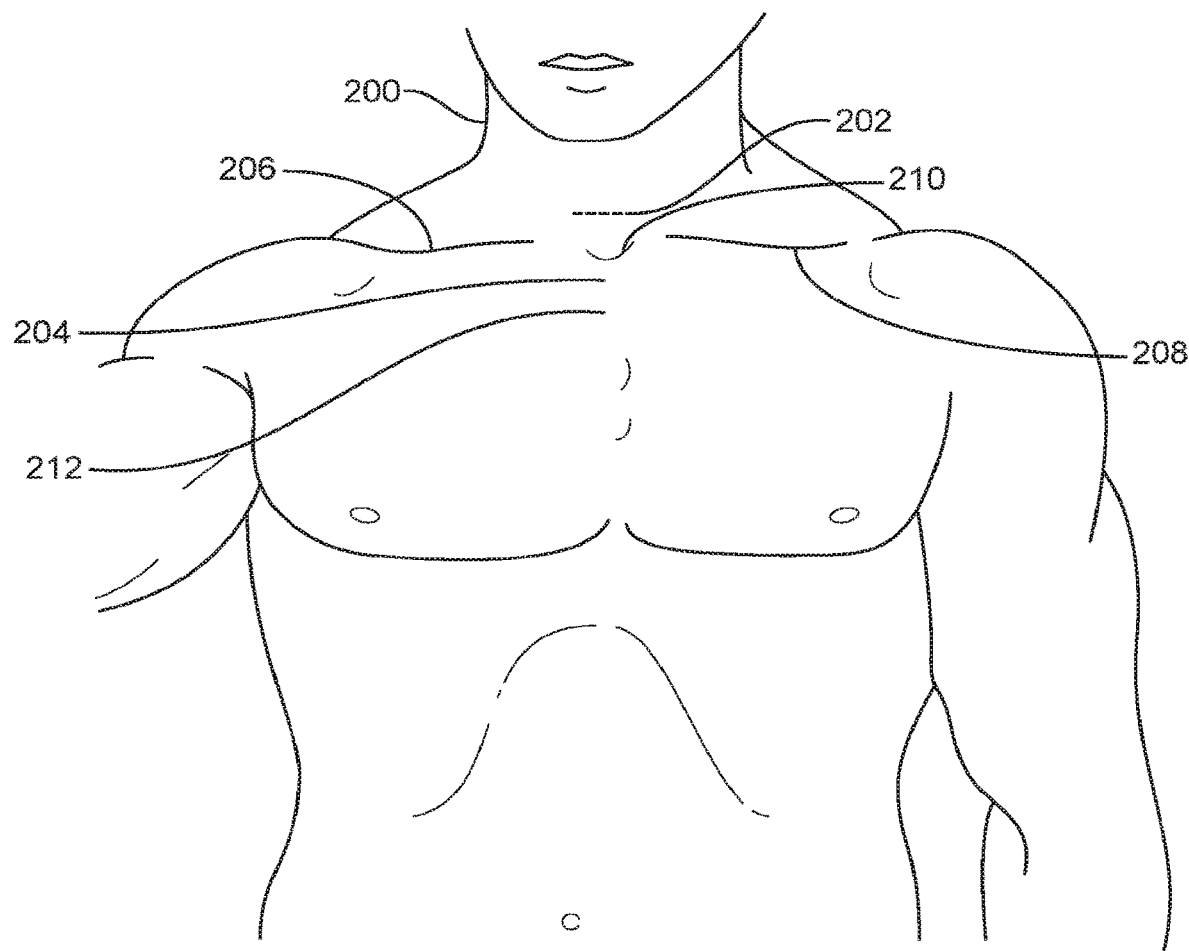
FIG. 2 is a schematic diagram illustrating an example thoracic cavity.

FIG. 2 is a schematic diagram illustrating a location for making an incision in accordance with some embodiments. In some embodiments, an opening is made in a neck region 200 of a patient (e.g., at incision site 202). Incision 202 may be located, for example, in the suprasternal notch 210 which is the triangular space at the superior border of the manubrium of the sternum between the clavicular notches 204, 206. Through the opening, surgical instruments are delivered through the mediastinum toward the heart of the patient. This method of delivering surgical instruments through the mediastinum (e.g., the superior mediastinum) is called herein a mediastinal approach.

Figure 3:
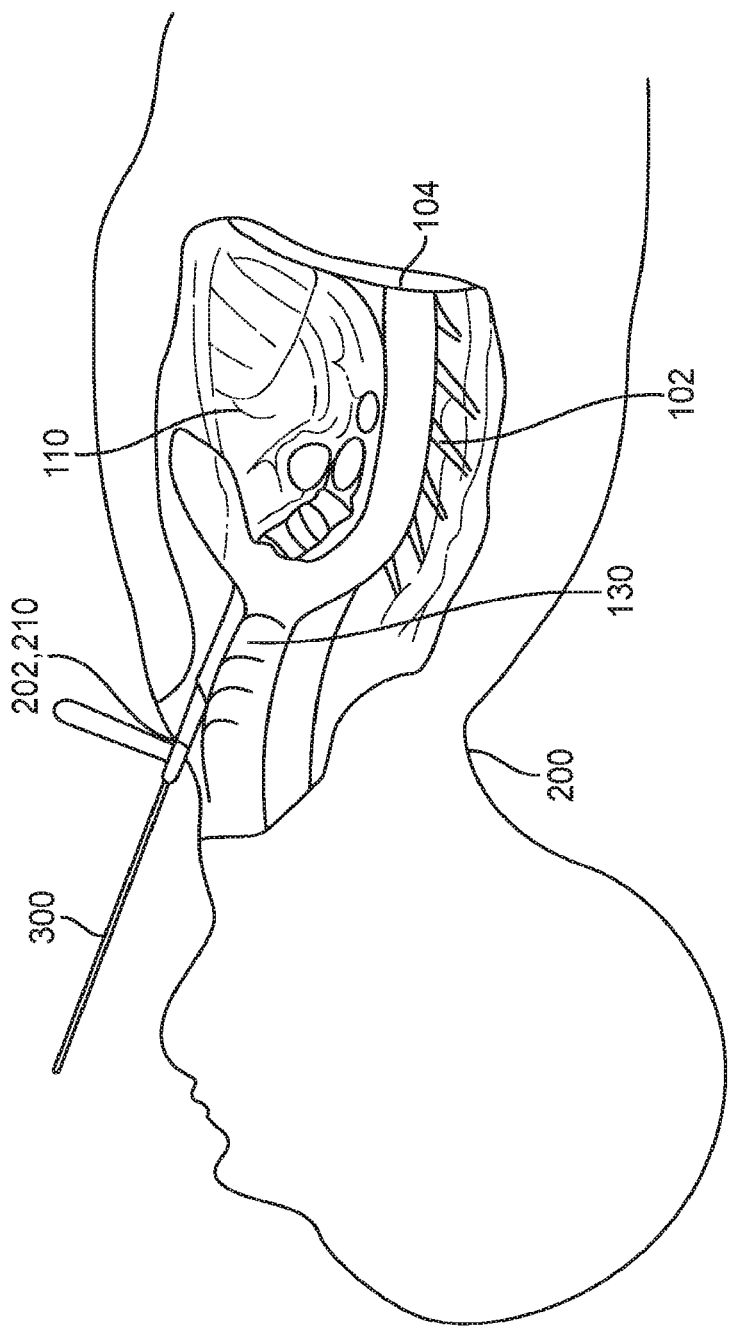
FIG. 3 is a schematic diagram illustrating insertion of an instrument through an opening adjacent to a neck, in accordance with some embodiments.

FIG. 3 is a schematic diagram illustrating insertion of an instrument 300 through an opening adjacent to a neck 200 in accordance with some embodiments. The instrument 300 is inserted through the opening 202, which allows direct access to the heart 110 without having to cut, open, remove, and/or separate one or more portions of the rib cage 102 and/or the thoracic diaphragm 104.

FIGS. 4A-4F illustrate delivery of a surgical instrument 400 in accordance with some embodiments.

Figure 4A:
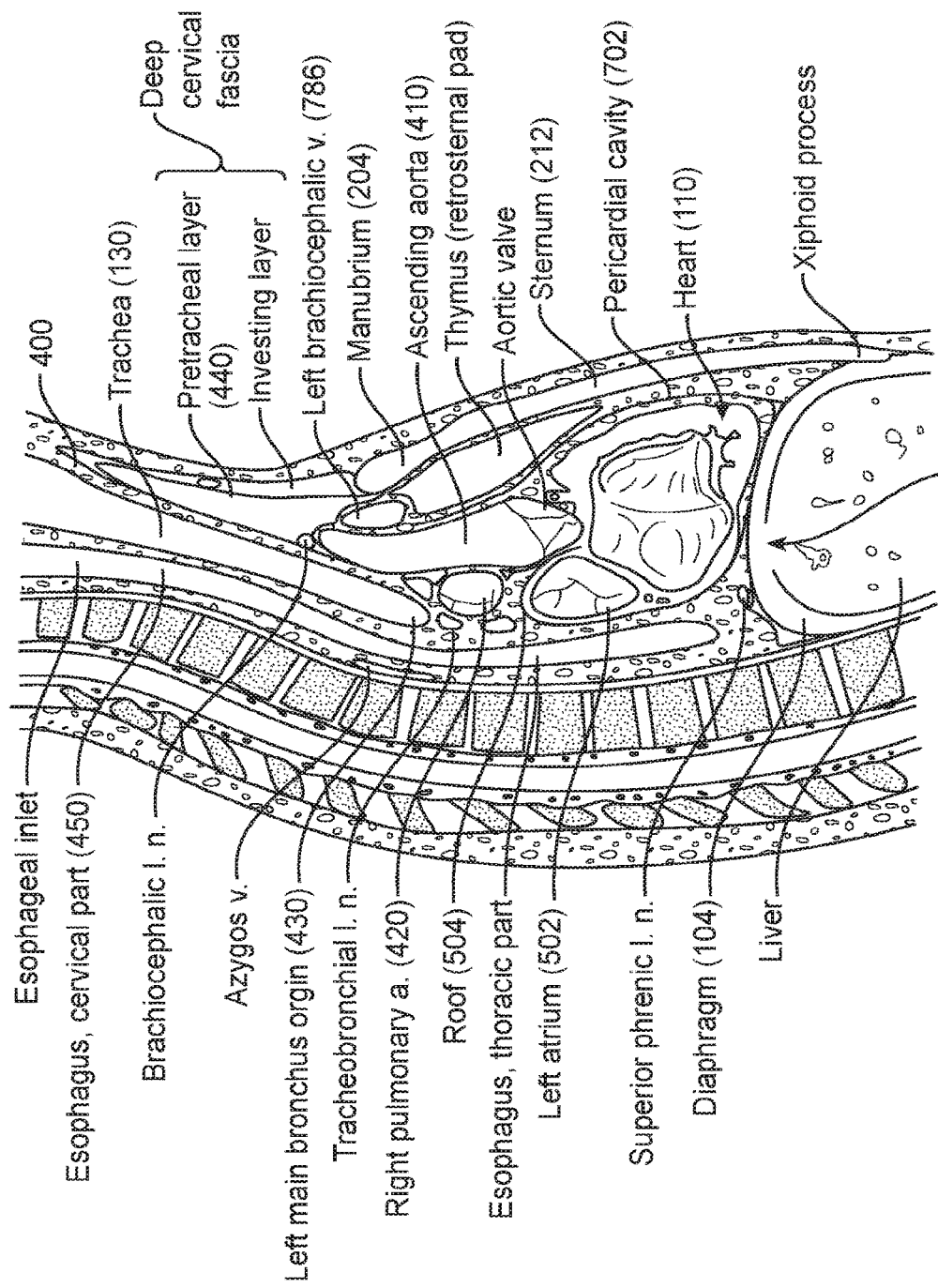

FIG. 4A shows an example sagittal cross-section of a chest region of a patient. Shown on the right hand side of FIG. 4A is the anterior portion of the patient and shown on the left hand side of FIG. 4A is the posterior portion of the patient, including the spine.

Figure 4B:
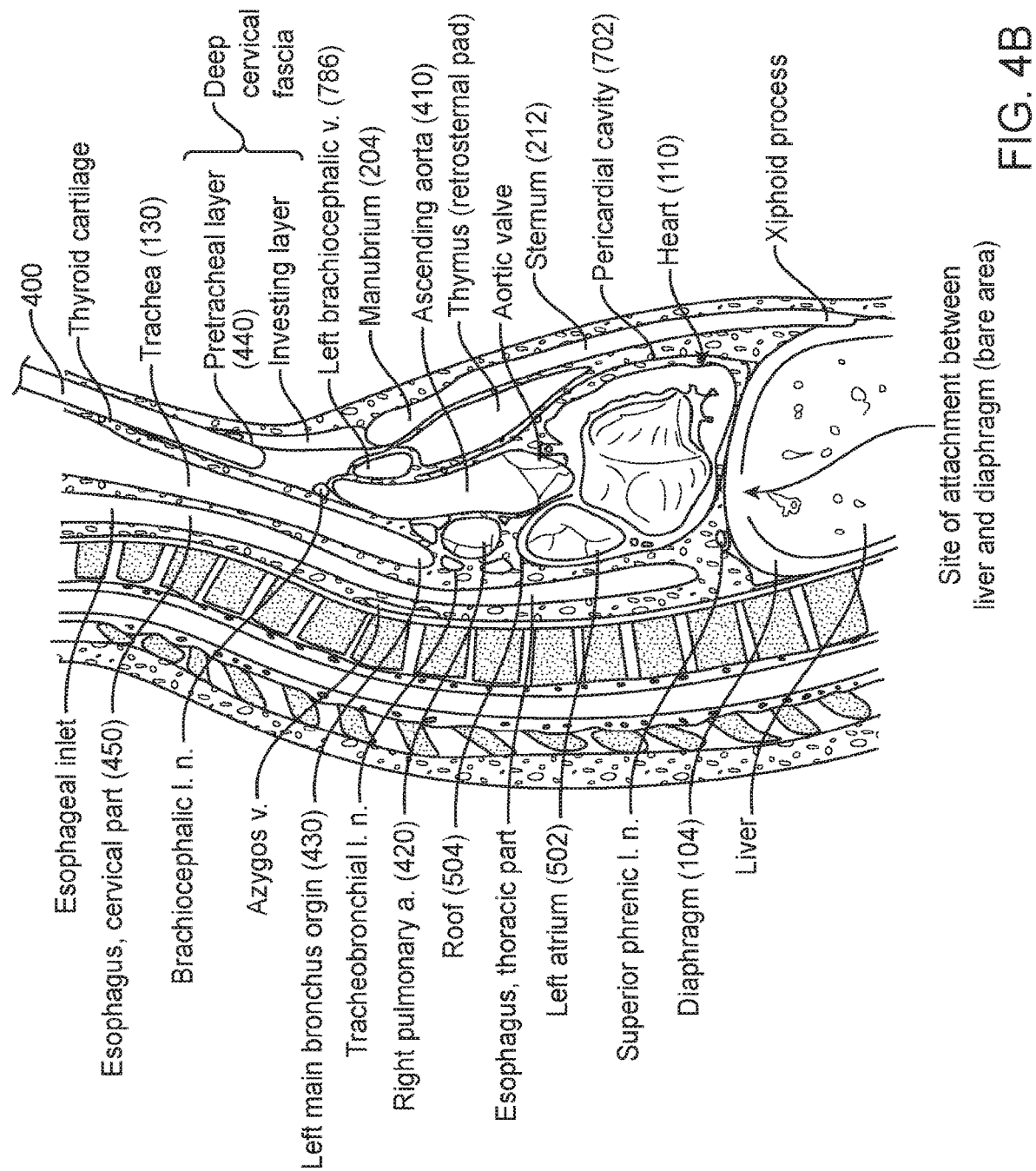

FIG. 4B illustrates insertion of an instrument 400 through the mediastinum. In FIG. 4B, the instrument 400 is inserted and advanced along the trachea 130 (e.g., along a path anterior to the trachea).

FIG. 4C shows that the instrument 400 is advanced further into a space between the trachea 130 and the ascending aorta 410.

Figure 4D:
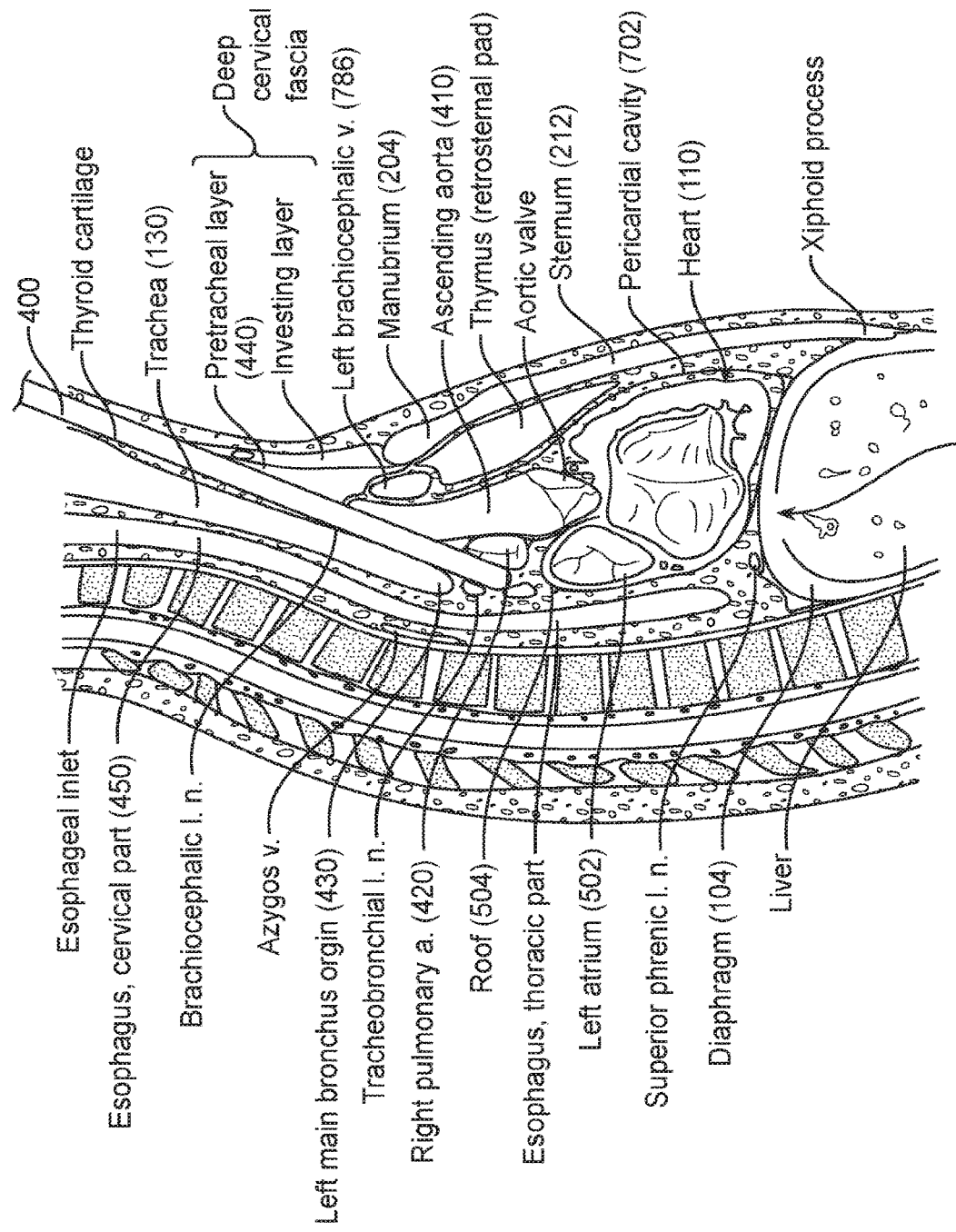

FIG. 4D illustrates that the instrument 400 is advanced even further into a space between the trachea 130 and a branch of the pulmonary artery 420 (e.g., a right pulmonary artery).

Figure 4E:
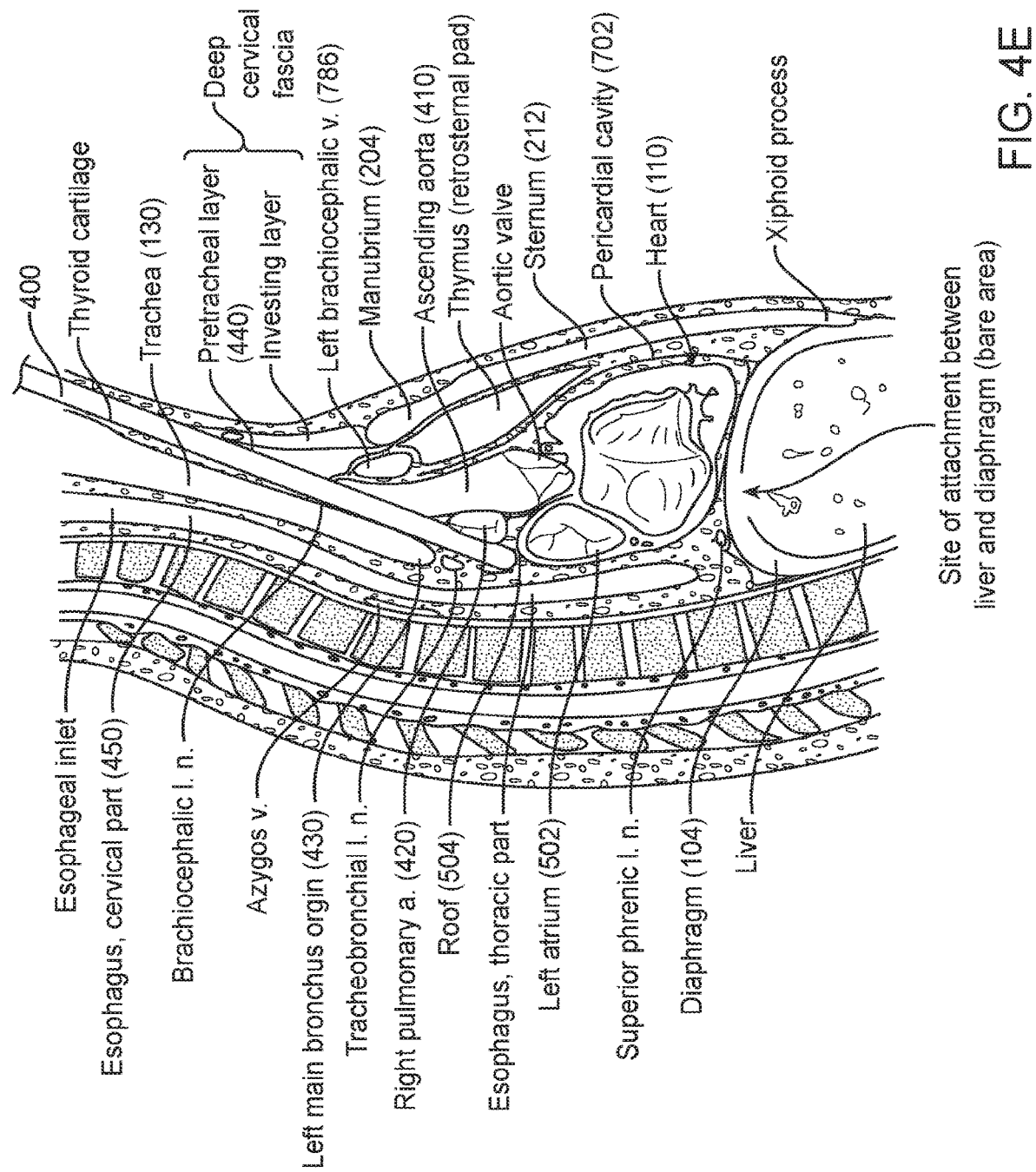

FIG. 4E illustrates that the instrument 400 is advanced toward the heart 110 (e.g., the cardiac wall, such as the wall of the left atrium). In some embodiments, the instrument 400 comes in contact with the heart 110 (e.g., the wall of the left atrium).

Although FIGS. 4C-4E show the instrument 400 located behind the ascending aorta 410 (e.g., behind the innomate artery and the aortic arch) and/or the pulmonary artery 420, a person skilled in the art would understand that the instrument 400 can be passed through the space between the trachea 130 and the ascending aorta 410 and the space between the trachea 130 and the pulmonary artery 420.

Figure 4F:
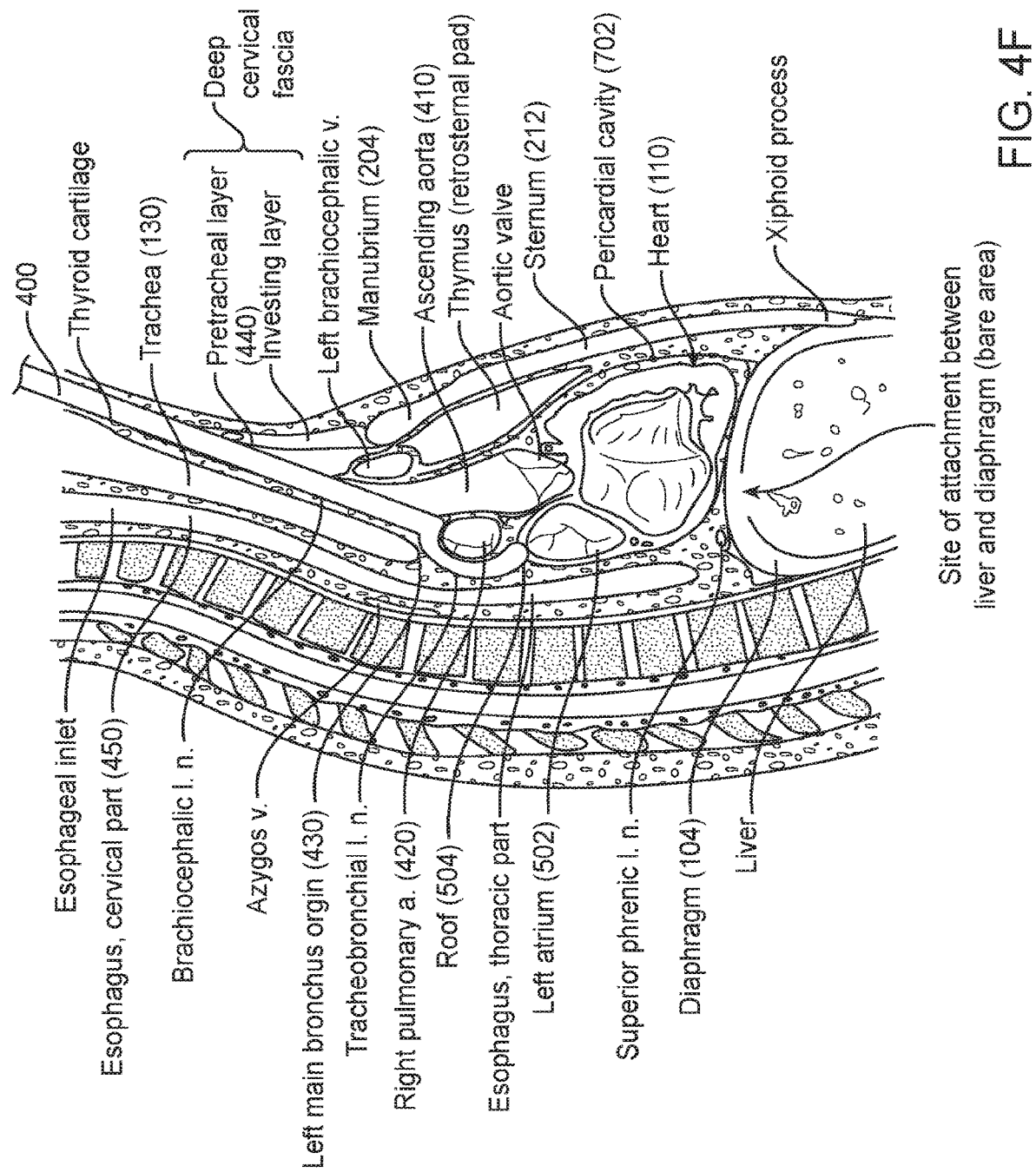

FIG. 4F illustrates a steerable instrument 400 (e.g., an instrument including a catheter). As shown in FIG. 4F, in some embodiments, the instrument 400 is steered around the pulmonary artery 420 to reach the left atrium 502. This reduces the extent of squeezing and/or bending of the right pulmonary artery 420 in accessing the left atrium 502.

In some embodiments, the instrument 400 is steered along the coronal plane, in addition to, or instead of, steering along the sagittal plane. For example, as shown in FIG. 1, the heart 110 is located slightly off from the sagittal plane. In some embodiments, the instrument 400 is steered between the left main bronchus 430 and the pulmonary artery 420 to access the left atrium 502. Thus, in some cases, the instrument 400 is also steered toward the left side of the patient to access the left atrium 502. In some embodiments, the instrument 400 is advanced at a diagonal angle from the opening 202 to the left atrium 502.

As shown above in FIGS. 4A-4F, the instrument 400 is delivered through the mediastinum, thereby eliminating the need for cutting, removing, or separating one or more portions of the rib cage 102 and/or the thoracic diaphragm 104. This, in turn, reduces or eliminates the problems associated with such procedures.

FIGS. 5A-5G are schematic diagrams illustrating making an opening on a cardiac wall in accordance with some embodiments.

Figure 5A:
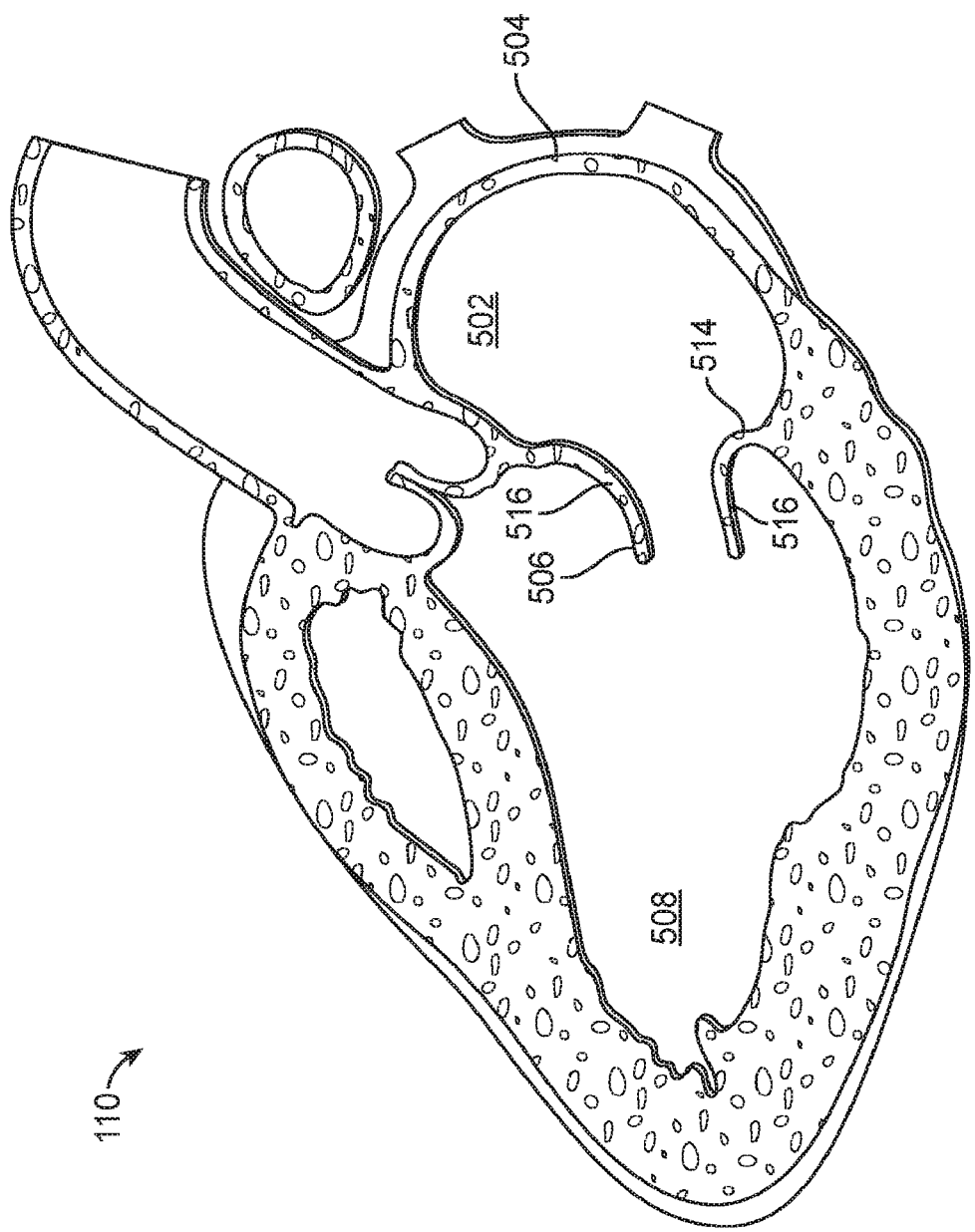
FIGS. 5A-5G are schematic diagrams illustrating making an opening on a cardiac wall, in accordance with some embodiments.

FIG. 5A shows an example parasagittal cross-section of a heart 110. Also shown in FIG. 5A are left atrium 502 and mitral valve 506. A wall of left atrium 502 includes a portion called the roof or the dome 504.

Figure 5B:
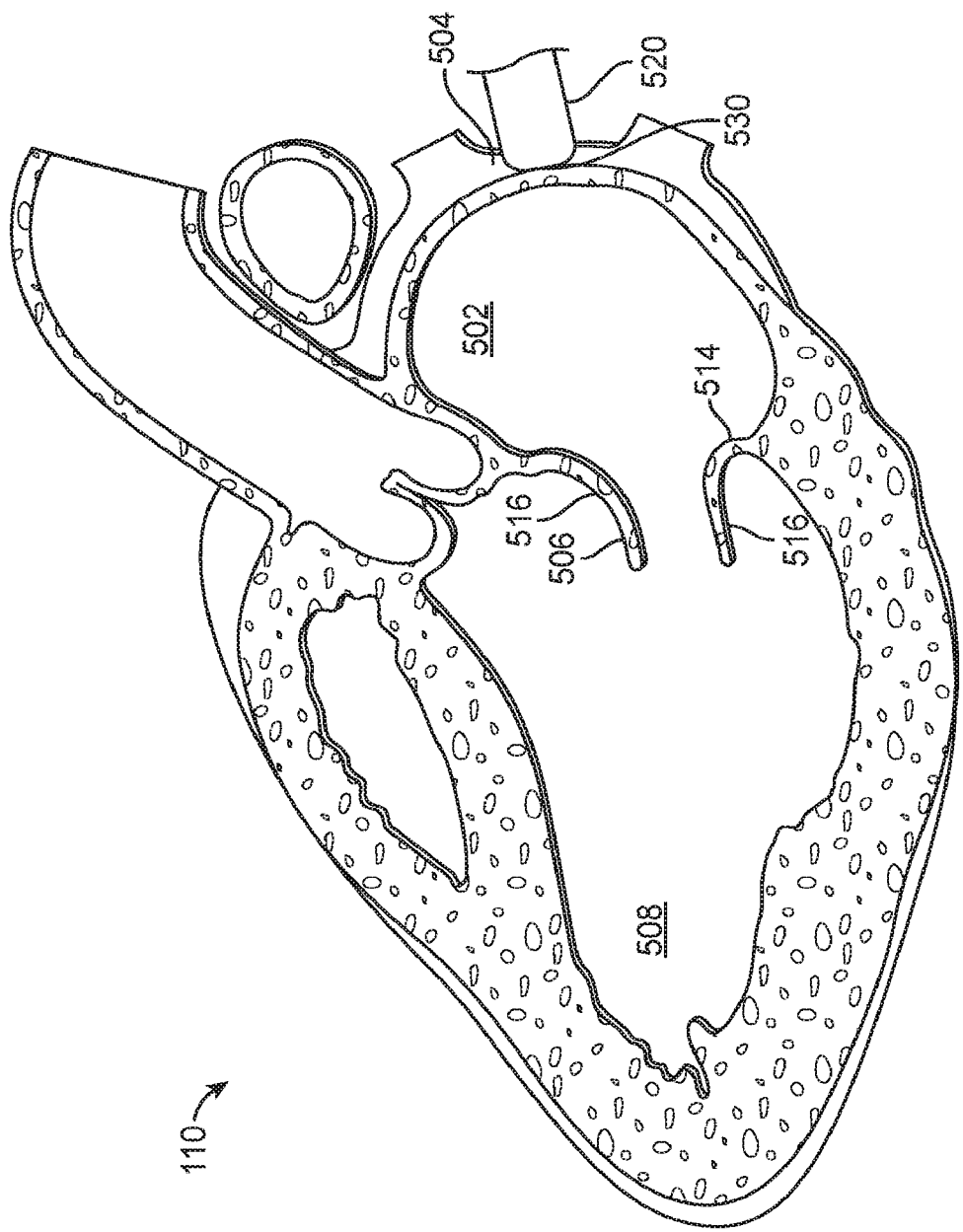
Figure 7A:
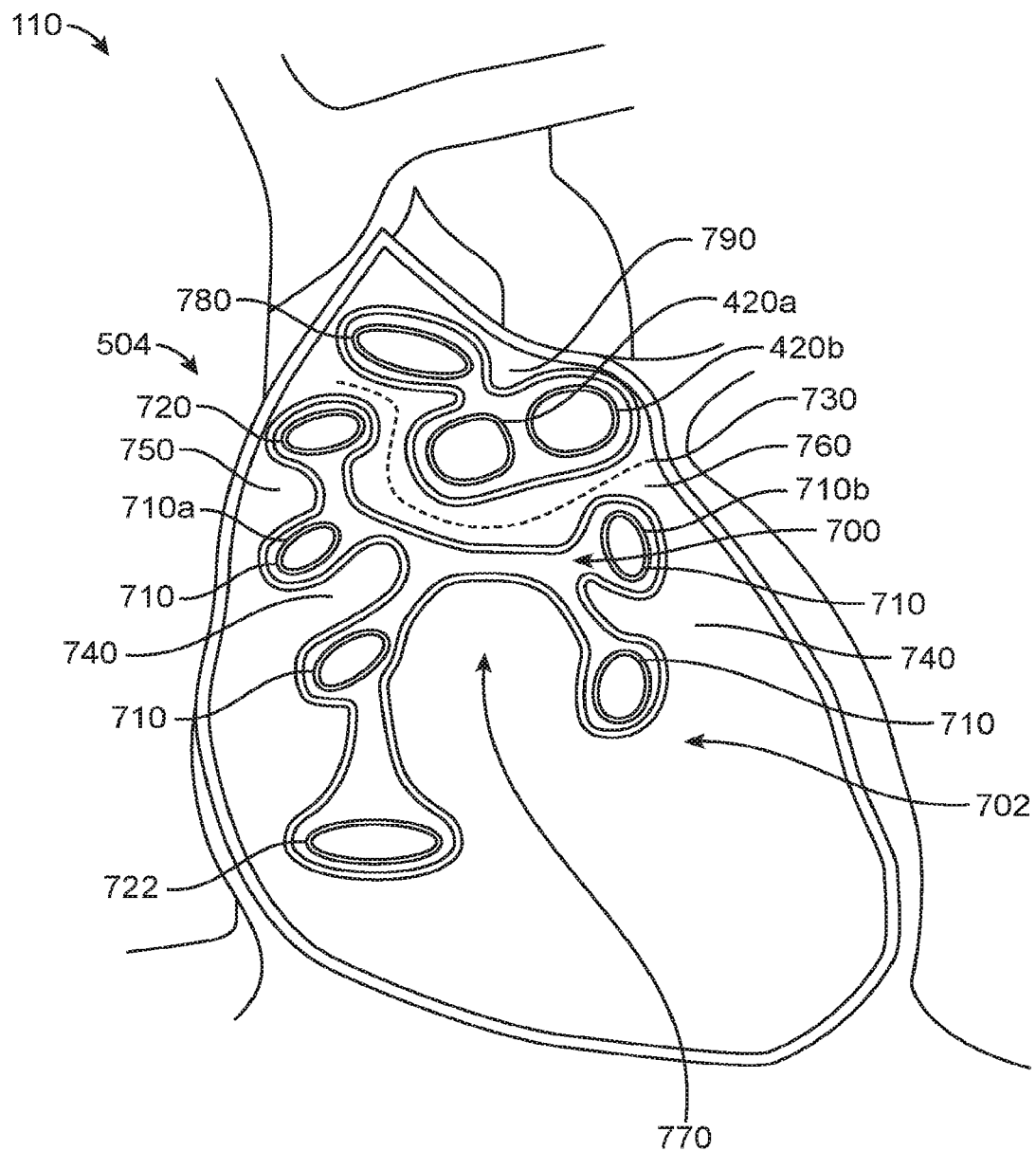
FIGS. 7A-7C show the extrapericardial location of the roof of the left atrium of the heart, in accordance with some embodiments.
Figure 7B:
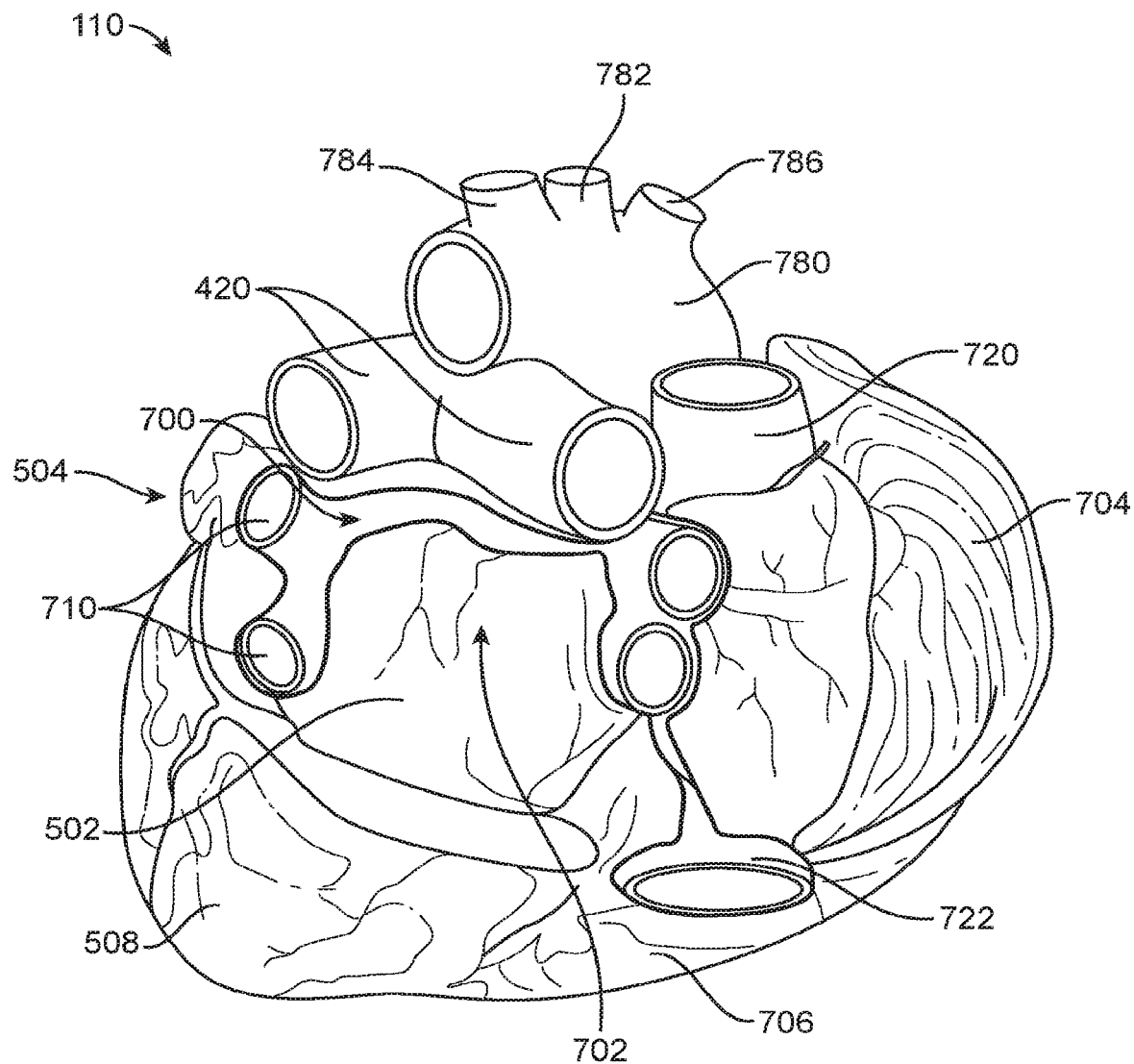
Figure 7C:
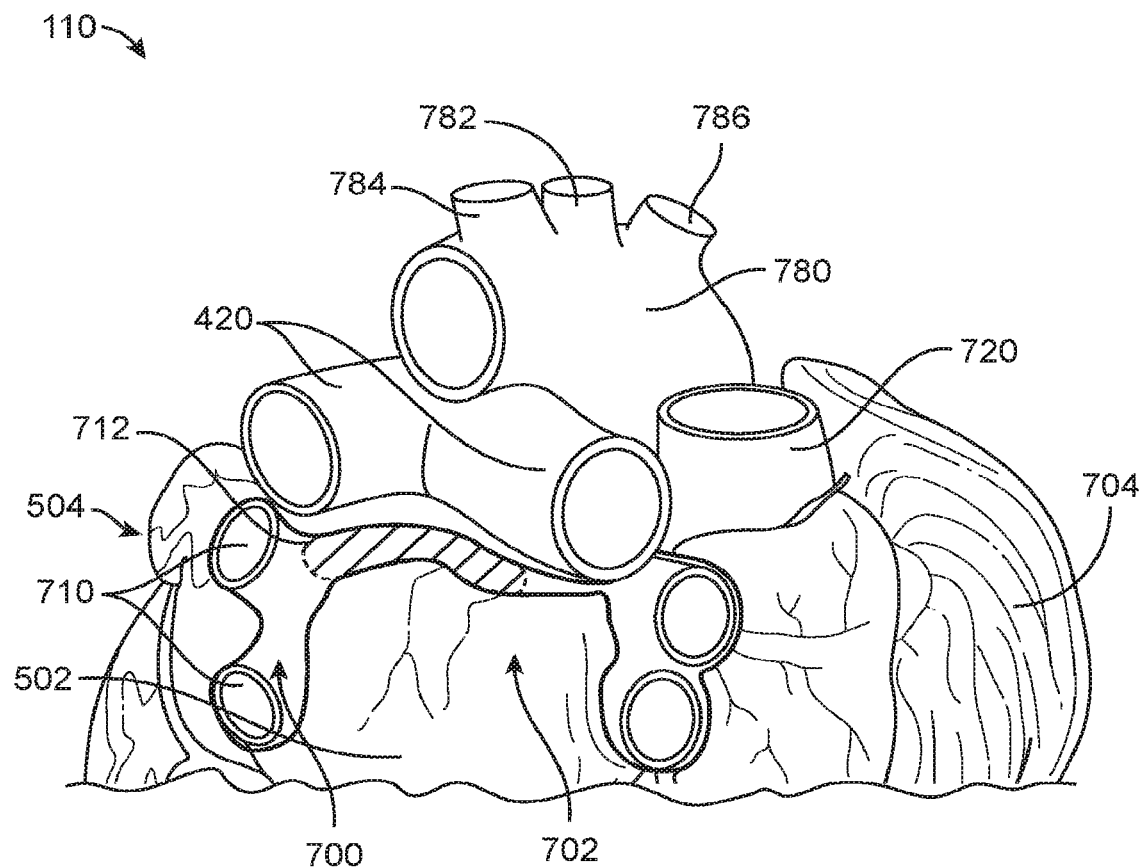

FIG. 5B shows that instrument 520 comes in contact with the wall of left atrium 502 (e.g., instrument 520 is delivered through the mediastinum as shown in FIGS. 4A-4F). In FIG. 5B, instrument 520 is in contact with the roof or dome 504 of left atrium 502. Preferably, instrument 520 contacts the roof or dome 504 in a location which lies outside the pericardium of the heart, for example as shown in FIGS. 7A-7C.

Although instrument 520 is illustrated schematically in FIG. 5B, in some embodiments, instrument 520 includes one or more components (e.g., one or more needles or blades) for making an opening on the wall of left atrium 502.

In some embodiments, instrument 520 includes sensor 530. Sensor 530 is configured to determine whether the first instrument is in contact with the cardiac wall.

Figure 5C:
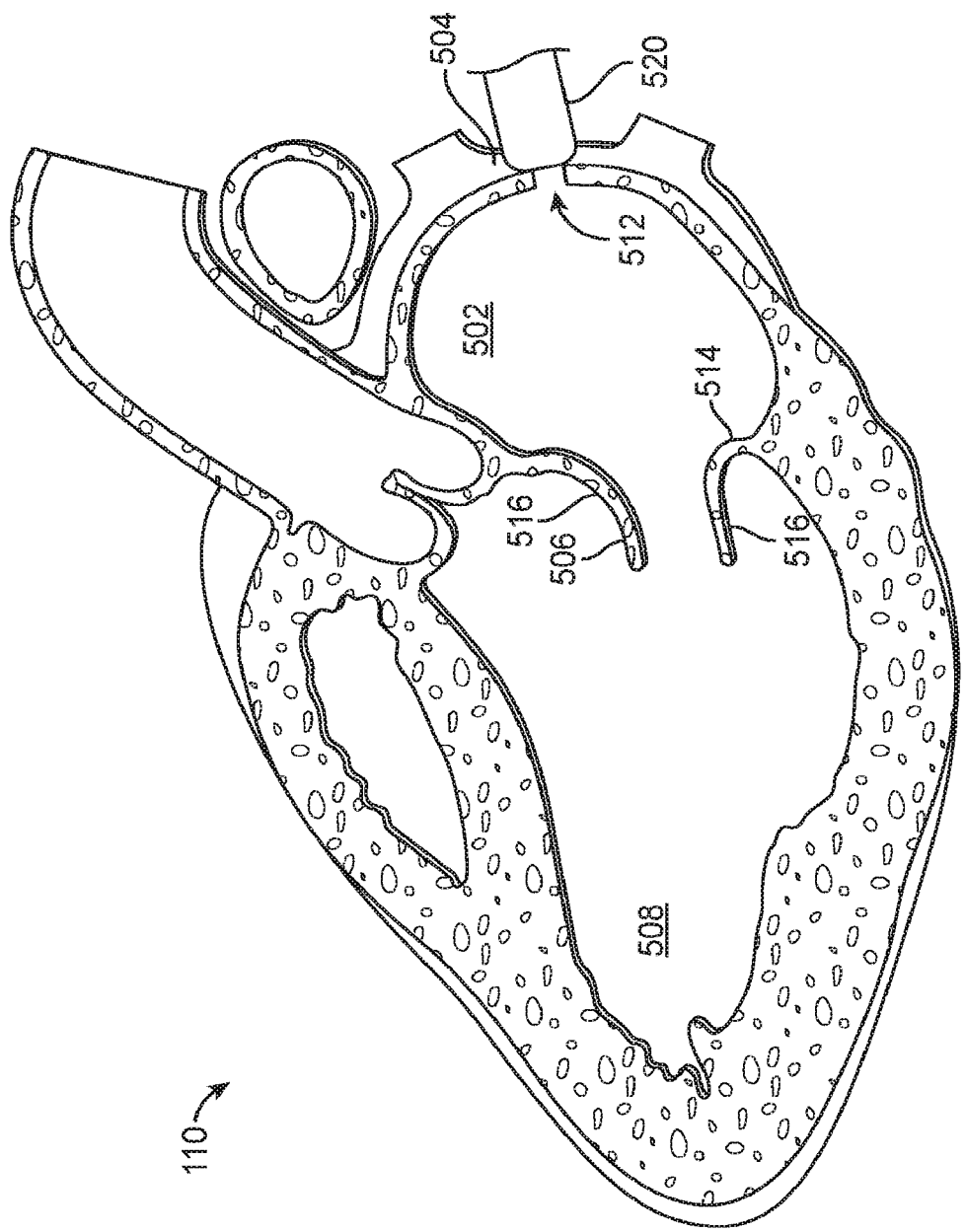

FIG. 5C illustrates that opening 512 is formed. In some embodiments, opening 512 is formed by using instrument 520 (e.g., instrument 520 includes a needle or blade and the blade of instrument 520 is used to make an incision on the wall of left atrium 502). This allows access to left atrium 502 and also mitral valve 506. Accessing mitral valve 506 through left atrium 502 has several advantages. For example, the systolic blood pressure in the left atrium 502 is typically less than 15 mmHg, whereas the systolic blood pressure in the left ventricle 508 is typically between 100 and 140 mmHg. Because the blood pressure in the left atrium 502 is lower than the blood pressure in the left ventricle 508, creating an opening 512 on the wall of the left atrium 502 has fewer complications than creating an opening on the wall of the left ventricle 508. For example, creating an opening 512 on the wall of the left atrium 502 causes less blood loss and facilitates closure of the opening and faster recovery than creating an opening on the wall of the left ventricle 508.

Figure 5D:
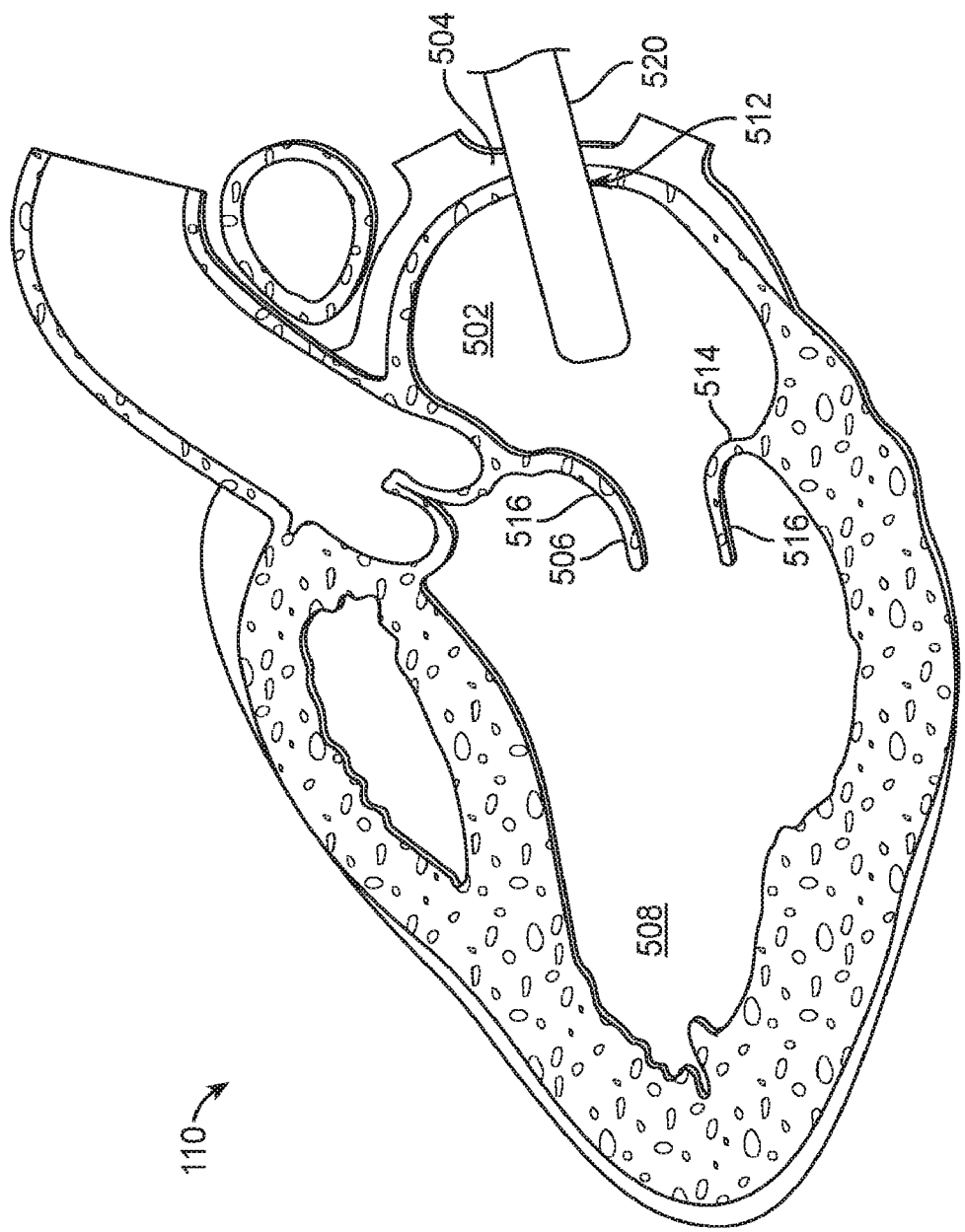

FIG. 5D illustrates that instrument 520 is further advanced (e.g., pushed) into left atrium 502. In some embodiments, while instrument 520 is partly located in left atrium 502, one or more cardiac procedures are performed (e.g., mitral valve surgery).

Figure 5E:
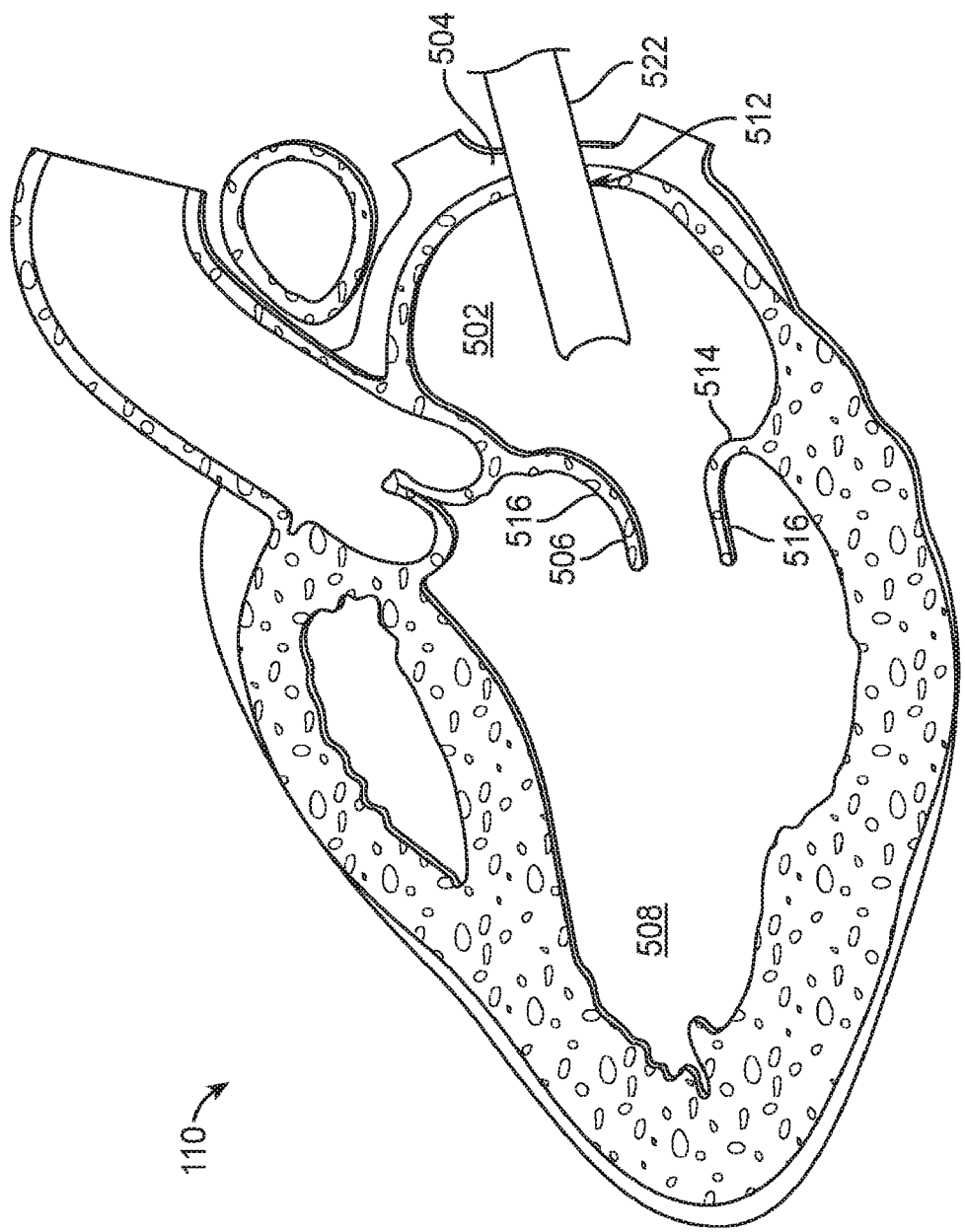

FIG. 5E illustrates that instrument 520 is removed (e.g., subsequent to making opening 512 on the wall of left atrium 502 or after inserting a portion of instrument 520 into left atrium 502). Subsequently, instrument 522 is inserted for performing one or more cardiac procedures. In some embodiments, instrument 520 is configured for making opening 512 on the wall of left atrium 502, and instrument 522 is configured for replacing mitral valve 506 (e.g., instrument 522 is a catheter, such as a catheter for transcatheter mitral valve replacement).

Figure 5F:
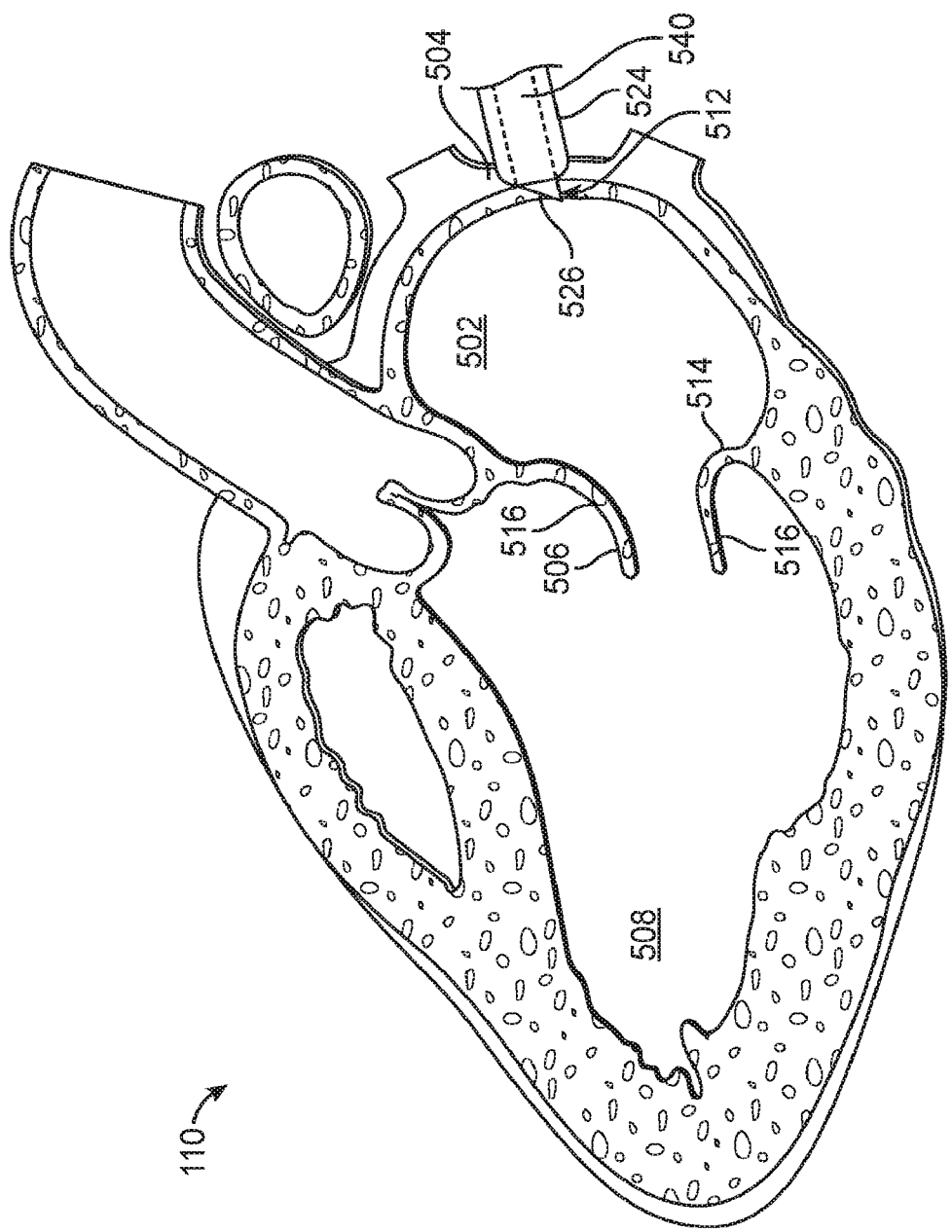

FIG. 5F illustrates that instrument 524 (instead of instrument 520 shown in FIG. 5B) comes in contact with the wall of left atrium 502. Instrument 524 includes hollow shell 524 (e.g., a tube). Hollow shell 524 is configured to allow one or more instruments to be transported through the inside of hollow shell 524. In FIG. 5F, incision device 526 (e.g., a device with a blade) is advanced through the inside of hollow shell 524. In some embodiments, incision device 526 is used to make an opening 512 on the wall of left atrium 502. In some embodiments, dilator sheaths are used to enlarge the opening 512 onto the left atrium 502.

Figure 5G:
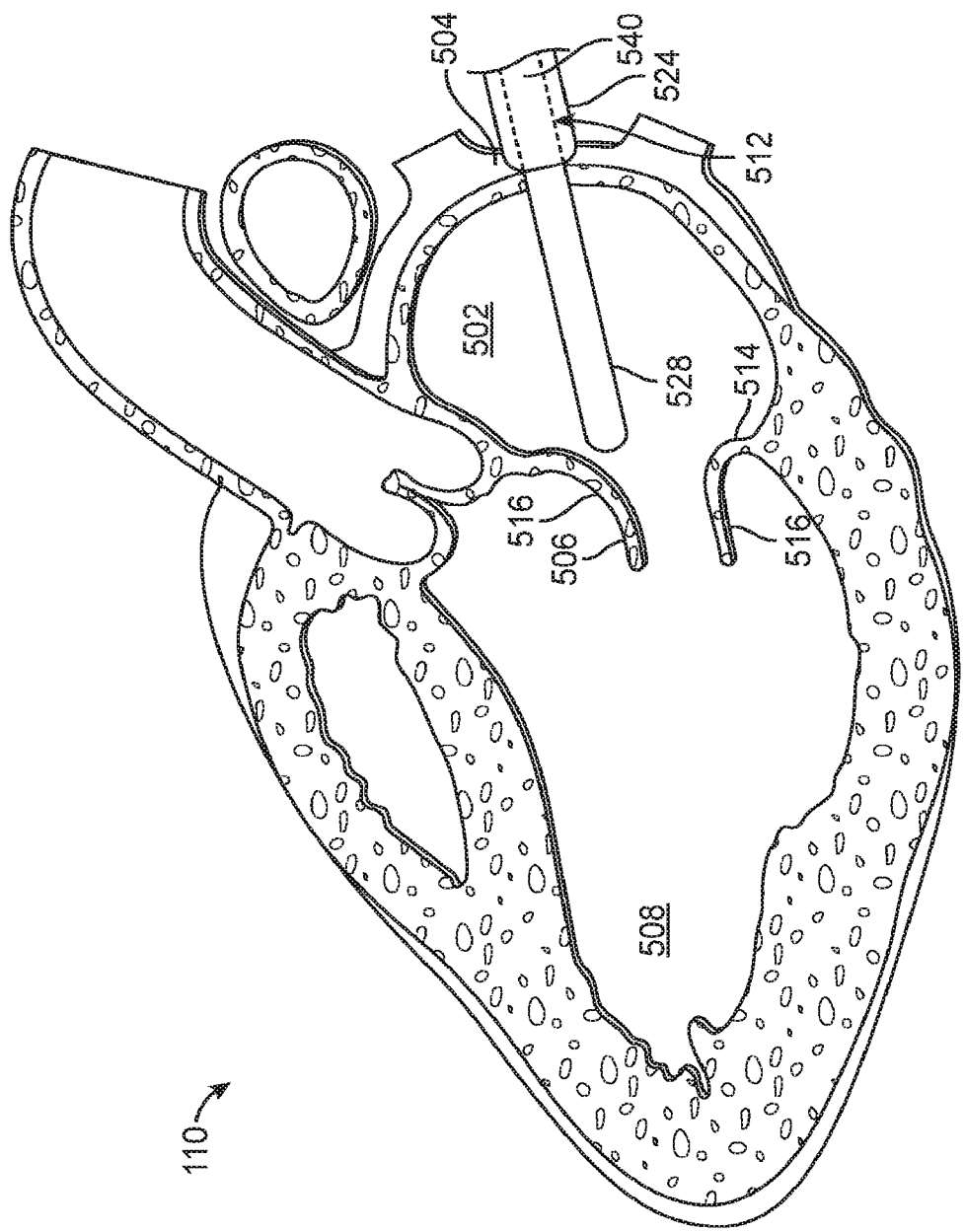

FIG. 5G illustrates that, after the opening 512 is made on the wall of left atrium 502, instrument 528 (e.g., an instrument that is different from device 526) is delivered through the inside of hollow shell 524.

In light of these principles, we turn to certain embodiments.

In accordance with some embodiments, a method includes inserting at least a portion of a first instrument through a first opening in a neck (e.g., adjacent to a suprasternal notch of a patient, as shown in FIG. 2). In some embodiments, the first opening has a diameter of 1-4 cm (e.g., 2-3 cm).

The method also includes advancing the first instrument (e.g., the inserted portion of the first instrument) toward a heart of the patient (e.g., FIGS. 4B-4E).

The method further includes making a second opening through an atrial wall of the heart for one or more cardiac procedures (e.g., FIG. 5C).

In some embodiments, advancing the first instrument toward the heart of the patient includes advancing the first instrument to the heart of the patient (e.g., the first instrument comes in contact with the heart of the patient, such as the wall of the left atrium). In some embodiments, advancing the first instrument toward the heart of the patient includes bringing the first instrument in contact with the heart of the patient.

In some embodiments, the method includes making a first incision adjacent to the suprasternal notch of the patient, thereby providing the first opening (e.g., FIG. 2). In some embodiments, the first incision is made without perforating an anterior wall of the patient's trachea.

In some embodiments, advancing the first instrument toward the heart of the patient includes advancing the first instrument through mediastinal space toward the heart of the patient (e.g., FIGS. 4B-4E).

In some embodiments, the method includes advancing the first instrument toward the heart of the patient includes advancing the first instrument along a first path that is along an anterior portion of a trachea of the patient (e.g., FIGS. 4B and 4C). In some embodiments, the path is substantially parallel to a plane defined by the trachea of the patient. In some embodiments, the path is anterior to the left or right main stem bronchus (e.g., primary bronchus). In some embodiments, the first path terminates proximate to the patient's fourth thoracic vertebra.

In some embodiments, the method includes, subsequent to advancing the first instrument along the first path, advancing at least the portion of the first instrument along a second path toward the cardiac wall of the heart (e.g., FIG. 4F).

In some embodiments, advancing the first instrument along the first path includes advancing the first instrument from a location adjacent to a first portion of the trachea (e.g., an upper portion of the trachea) to a location adjacent to a second portion of the trachea (e.g., a lower portion of the trachea) (e.g., FIGS. 4B-4C). Advancing the first instrument along the second path includes advancing the first instrument from the location adjacent to the second portion of the trachea toward the cardiac wall of the heart (e.g., FIG. 4F). In some embodiments, the second path corresponds to a distance of 0.1 to 4 cm. In some embodiments, the second path is substantially parallel to a plane defined by the patient's primary bronchus (e.g., the primary bronchus that is proximate to the patient's heart).

In some embodiments, the method includes tilting a head of the patient backward and optionally rotating the head to one side for advancing the first instrument toward the heart of the patient (e.g., FIG. 3). Tilting the head of the patient backward facilitates access to the first opening. In addition, tilting the heat aligns the thorax for advancing the first instrument toward the heart of the patient. In some embodiments, the method includes placing a shoulder roll under the shoulders (e.g., between scapulae). This facilitates elevating the shoulder and extending the neck. The shoulder roll also facilitates extension of the cervical area.

In some embodiments, the method includes making the second opening through an atrial chamber of the heart that corresponds to a left side of the heart (e.g., as shown in FIG. 5C, an opening is made on the wall of left atrium 502).

In some embodiments, the second opening is made adjacent to the roof or dome (e.g., a top) of the left atrium of the heart. In some embodiments, the dome of the left atrium corresponds to a portion of the left atrium that is not covered by pericardium (e.g., serous pericardium). In some embodiments, the second opening is made at a location that corresponds to the roof or dome (e.g., the top) of the left atrium of the heart.

Because the dome of the left atrium is not covered by pericardium, making the second opening adjacent to (or at) the dome of the left atrium does not require cutting, making an incision on, and/or removing, at least a portion of the pericardium of the heart. Cutting, making an incision on, and/or removing a portion of the pericardium of the heart delays the recovery of the patient, and can increase the length of the patient's hospital stay. In addition, cutting, making an incision on, and/or removing a portion of the pericardium of the heart causes loss of pericardial fluid from the pericardial cavity, which reduces the function of the pericardium. In some cases, cutting, making an incision on, and/or removing a portion of the pericardium of the heart causes pericarditis, which often involves chest pain, pericardial friction rub, and/or a pericardial effusion, which in turn can cause pericardial pre-tamponade and/or tamponade and/or infections of the pericardial space. By eliminating cutting, making an incision on, and/or removing a portion of the pericardium of the heart, these and other problems associated with the pericardium can be avoided.

In some embodiments, the method includes making the second opening through the cardiac wall of the heart without accessing a pericardial cavity of the heart. In some embodiments, the method includes making the second opening through the cardiac wall of the heart without causing release of pericardial fluid from the pericardial cavity.

In some embodiments, the method includes making the second opening through the cardiac wall of the heart without cutting, making an incision on, and/or removing, at least a portion of a pericardium of the heart.

In some embodiments, the method includes making the second opening through the cardiac wall of the heart without accessing a pericardium of the heart.

In some embodiments, the method includes determining whether the first instrument has reached the cardiac wall of the heart. For example, the method includes visually determining whether the first instrument has reached the cardiac wall of the heart (e.g., the wall of the left atrium). In some embodiments, the visual determination is made by using an endoscope, ultrasound imaging (e.g., by delivering an ultrasound probe adjacent to the heart), and/or radiological imaging (e.g., fluoroscopy). In some embodiments, the first instrument includes a sensor (e.g., mechanical and/or electrical sensor 530 in FIG. 5B). For example, the first instrument includes an electrical sensor (e.g., an electrode) configured to receive an electrical signal from the cardiac wall while the first instrument (e.g., the electrical sensor of the first instrument) is in contact with the cardiac wall. A determination whether the first instrument has reached the cardiac wall of the heart is made based on a determination whether the electrical sensor is receiving or has received the electrical signal from the heart (e.g., the first instrument is deemed to have reached the cardiac wall of the heart based on a determination that the electrical sensor is receiving or has received the electrical signal from the heart and the first instrument is deemed to have not reached the cardiac wall of the heart based on a determination that the electrical sensor is not receiving or has not received the electrical signal from the heart).

In some embodiments, the method includes determining that the first instrument has reached the cardiac wall of the heart; and, in response to determining that the first instrument has reached the cardiac wall of the heart, making the second opening through the cardiac wall of the heart for one or more cardiac procedures. For example, in some embodiments, the second opening is made only after determining that the first instrument has reached the cardiac wall of the heart.

In some embodiments, the method includes determining that the first instrument has not reached the cardiac wall of the heart, and in response to determining that the first instrument has not reached the cardiac wall of the heart, further advancing the first instrument toward the heart. In some embodiments, the method includes determining that the first instrument has not reached the cardiac wall of the heart, and in response to determining that the first instrument has not reached the cardiac wall of the heart, forgoing making the second opening through the cardiac wall of the heart.

In some embodiments, the method includes making the second opening through the cardiac wall of the heart using the first instrument (e.g., instrument 520 in FIG. 5C); and subsequent to making the second opening, inserting the first instrument through the second opening for the one or more cardiac procedures (e.g., FIG. 5D). For example, the first instrument is configured for making the second opening through the cardiac wall of the heart, and the first instrument is also configured for removing, repairing, inserting, or replacing the mitral valve.

In some embodiments, the method includes making the second opening through the cardiac wall of the heart using the first instrument (e.g., instrument 520 in FIG. 5C); and, subsequent to making the second opening, inserting a second instrument that is distinct from the first instrument, through the second opening for the one or more cardiac procedures (e.g., instrument 522 in FIG. 5E). For example, the first instrument is configured for making the second opening through the cardiac wall of the heart, and the first instrument is also configured for removing, repairing, inserting, or replacing the mitral valve.

In some embodiments, the method includes reducing a gap around a respective instrument (e.g., the first instrument or the second instrument) inserted through the second opening. In some embodiments, reducing the gap includes increasing a diameter of the respective instrument (e.g., the instrument is configured to change its outer diameter). In some embodiments, reducing the gap includes reducing a diameter of the second opening (e.g., an additional instrument or device is applied on the outside wall and/or the inside wall of the left atrium to provide pressure and reduce the diameter of the second opening). In some embodiments, reducing the gap includes providing a sealing device (e.g., a balloon seal).

In some embodiments, the method includes providing a gas to the patient's chest cavity prior to inserting the respective instrument through the first opening. In some embodiments, the method includes continuing to provide the gas to the patient's chest cavity while the respective instrument is at least partially inserted through the first opening. In some embodiments, the gas includes carbon dioxide. In some embodiments, the gas is carbon dioxide. In some embodiments, the method includes increasing a pressure inside the patient's chest cavity to satisfy a predetermined pressure threshold (e.g., the pressure inside the patient's chest cavity remains above the predetermined pressure threshold).

In some embodiments, the method includes, prior to making the second opening through the cardiac wall of the heart, slowing down the patient's heart rate and/or reducing the patient's blood pressure. In some embodiments, the patient's heart rate is slowed down and/or the patient's blood pressure is reduced by one or more medications, one or more pacing electrodes, anesthesia or cardiopulmonary bypass, a cardiac assist device, etc. In some embodiments, the method includes forgoing slowing down the patient's heart rate and/or reducing the patient's blood pressure.

In some embodiments, the method includes, prior to making the second opening through the cardiac wall of the heart, temporarily stopping the patient's heart. In some embodiments, the patient's heart rate is stopped by one or more medications, one or more pacing electrodes, anesthesia or cardiopulmonary bypass, a cardiac assist device, etc. In some embodiments, the method includes forgoing temporarily stopping the patient's heart prior to making the second opening through the cardiac wall of the heart (e.g., the patient's heart rate and/or the patient's blood pressure is reduced without temporarily stopping the patient's heart).

In some embodiments, the one or more cardiac procedures include one or more surgical procedures. In some embodiments, the one or more cardiac procedures include one or more minimally-invasive procedures. In some embodiments, the one or more cardiac procedures include mitral valve surgery. In some embodiments, the one or more cardiac procedures include mitral valve replacement. In some embodiments, the one or more cardiac procedures include mitral valve repair. In some embodiments, the one or more cardiac procedures include left atrial appendage closure. In some embodiments, the one or more cardiac procedures include ablation (e.g., ablation for atrial fibrillation, such as left atrial fibrillation). In some embodiments, the one or more cardiac procedures include cardiac biopsy (e.g., biopsy of the left ventricle, which is used sometimes for diagnosing cardiomyopathy). In some embodiments, the one or more cardiac procedures include any of the cardiac procedures described herein.

In some embodiments, the method includes performing a respective cardiac procedure of the one or more cardiac procedures.

In some embodiments, the method includes, subsequent to performing the respective cardiac procedure, closing the second opening (e.g., suturing the second opening).

In some embodiments, the method includes removing the first instrument from the first opening.

In some embodiments, the method includes, subsequent to removing the first instrument from the first opening, closing the first opening (e.g., suturing the first opening).

In accordance with some embodiments, a method includes inserting a first instrument through a first opening of a patient; advancing the first instrument toward the roof or dome (e.g., a top) of a left atrium of a heart of the patient; and making a second opening through a cardiac wall adjacent to the roof or dome (e.g., the top) of the left atrium of the heart for one or more cardiac procedures.

In accordance with some embodiments, a method includes inserting a first instrument through a first opening of a patient; advancing the first instrument toward the roof or dome (e.g., a top) of a left atrium of a heart of the patient; and performing one or more cardiac procedures (e.g., without making the second opening). In some embodiments, the one or more cardiac procedures include ablation (e.g., ablation for atrial fibrillation, such as radiofrequency ablation or cryoablation). In some embodiments, the one or more cardiac procedures include clipping the left atrial appendage. In some embodiments, the one or more cardiac procedures include making an incision on the pericardium (and/or accessing the pericardium).

In accordance with some embodiments, a surgical instrument includes means for performing any of the methods described herein.

In accordance with some embodiments, a surgical instrument includes means for inserting at least a portion of a first instrument through a first opening adjacent to a suprasternal notch of a patient (e.g., a port); means for advancing at least a portion of the first instrument toward a heart of the patient (e.g., a catheter); and means for making a second opening through a cardiac wall of the heart for one or more cardiac procedures (e.g., needle or blade).

In accordance with some embodiments, a surgical instrument includes means for, subsequent to inserting at least a portion of a first instrument through a first opening adjacent to a suprasternal notch of a patient and advancing the first instrument toward a heart of the patient, making a second opening through a cardiac wall of the heart for one or more cardiac procedures (e.g., a needle or blade, which is optionally coupled with a catheter with or without dilators).

In accordance with some embodiments, a surgical instrument includes means for inserting the first instrument through a first opening of a patient; means for advancing the first instrument toward a dome of a left atrium of a heart of the patient; and means for making a second opening through a cardiac wall adjacent to the dome of the left atrium of the heart for one or more cardiac procedures.

In accordance with some embodiments, a surgical instrument includes means for, subsequent to inserting at least a portion of a first instrument through a first opening and advancing the first instrument toward a heart of the patient, making a second opening through a cardiac wall of the heart for one or more cardiac procedures.

In accordance with some embodiments, a surgical instrument includes an incision device configured for making an opening through a cardiac wall of a heart of a patient. The incision device is configured for insertion through a first opening adjacent to a suprasternal notch of a patient and extension from the first opening to the heart of the patient.

In some embodiments, the surgical instrument includes means for positioning the incision device adjacent to the roof or dome (e.g., a top) of a left atrium of the heart of the patient (e.g., a catheter and/or one or more sensors configured for determining whether the incision device has reached the heart of the patient).

In some embodiments, the surgical instrument includes a hollow shell configured for advancing the incision device from the first opening adjacent to the suprasternal notice of the patient toward the heart of the patient.

In some embodiments, the hollow shell includes a tube.

In accordance with some embodiments, a surgical instrument includes means for inserting the first instrument through a first opening of a patient; means for advancing the first instrument toward a dome of a left atrium of a heart of the patient; and means for ablating a portion of the heart (e.g., means for a portion of the wall of the left atrium, such as a radiofrequency ablation device that includes one or more radiofrequency ablation probes or a cryogenic ablation device that includes one or more tubes for transferring a lower temperature medium, such as liquid nitrogen).

In accordance with some embodiments, a surgical instrument kit includes means for performing any of the methods described herein (e.g., the first instrument). In some embodiments, the surgical instrument kit includes the first instrument.

In accordance with some embodiments, a surgical instrument kit includes means for inserting at least a portion of a first instrument through a first opening adjacent to a suprasternal notch of a patient; means for advancing the first instrument toward a heart of the patient; and means for making a second opening through a cardiac wall of the heart for one or more cardiac procedures. In some embodiments, the surgical instrument kit also includes a catheter for transcatheter mitral valve replacement. In some embodiments, the surgical instrument kit includes an incision device configured for making the first opening.

In accordance with some embodiments, a surgical instrument kit includes means for inserting the first instrument through a first opening of a patient; means for advancing the first instrument toward a dome of a left atrium of a heart of the patient; and means for making a second opening through a cardiac wall adjacent to the dome of the left atrium of the heart for one or more cardiac procedures. In some embodiments, the surgical instrument kit also includes a catheter for transcatheter mitral valve replacement. In some embodiments, the surgical instrument kit includes an incision device configured for making the first opening.

Referring again to FIG. 2, the incision location (also referred to herein as an opening or a first opening) 202 may be cranial to the sternum 212 of the patient. In some embodiments, the incision location 202 may be in a neck 200 of the patient. For example, the incision location 202 may be adjacent the suprasternal notch 210 of the patient as described herein. The suprasternal notch 210 is a generally triangular gap between the collar bones 206, 208 of the patient where the tissue is free from underlying bone. The incision location 202 may be within, above, or through the triangular gap of the suprasternal notch 210. In some embodiments, an opening 202 in the suprasternal notch 210 of the patient may be made by making an incision adjacent the suprasternal notch 210 of the patient.

The incision 202 may be sized such that it does not extend into the manubrium 204 or the sternum 212. The incision may have a length within a range of about 0.5 cm to about 8 cm, for example within a range of about 1 cm to about 4 cm, within a range of about 2 cm to about 6 cm, within a range of about 5 to about 8 cm, or within a range of about 0.5 cm to about 4 cm. In the anterior-posterior dimension, from the superior border of the sternum to the trachea, the incision may have a depth within a range of about 0.5 cm to about 3 cm, for example within a range of about 2 cm to about 3 cm.

Referring again to FIG. 3, at least a distal portion of an instrument 300 (e.g. an intracardiac access device as described herein) may be inserted through the incision 202 to access the heart 110. In some embodiments, the incision location 202 may be in the suprasternal notch 210 and the distal portion of the instrument 300 may be inserted through the incision 202 in the suprasternal notch 210 of the patient to access the heart 110. The distal portion of the instrument 300 may be inserted through the incision 202 in order to access the heart 110 without cutting or separating bone (e.g. the sternum 212, manubrium 204, or a rib 102) of the patient as described herein. The distal portion of the instrument 300 may be configured to contact the cardiac wall on the dome 504 of the left atrium 502 while the proximal portion extends out of the opening 202.

Figure 6:
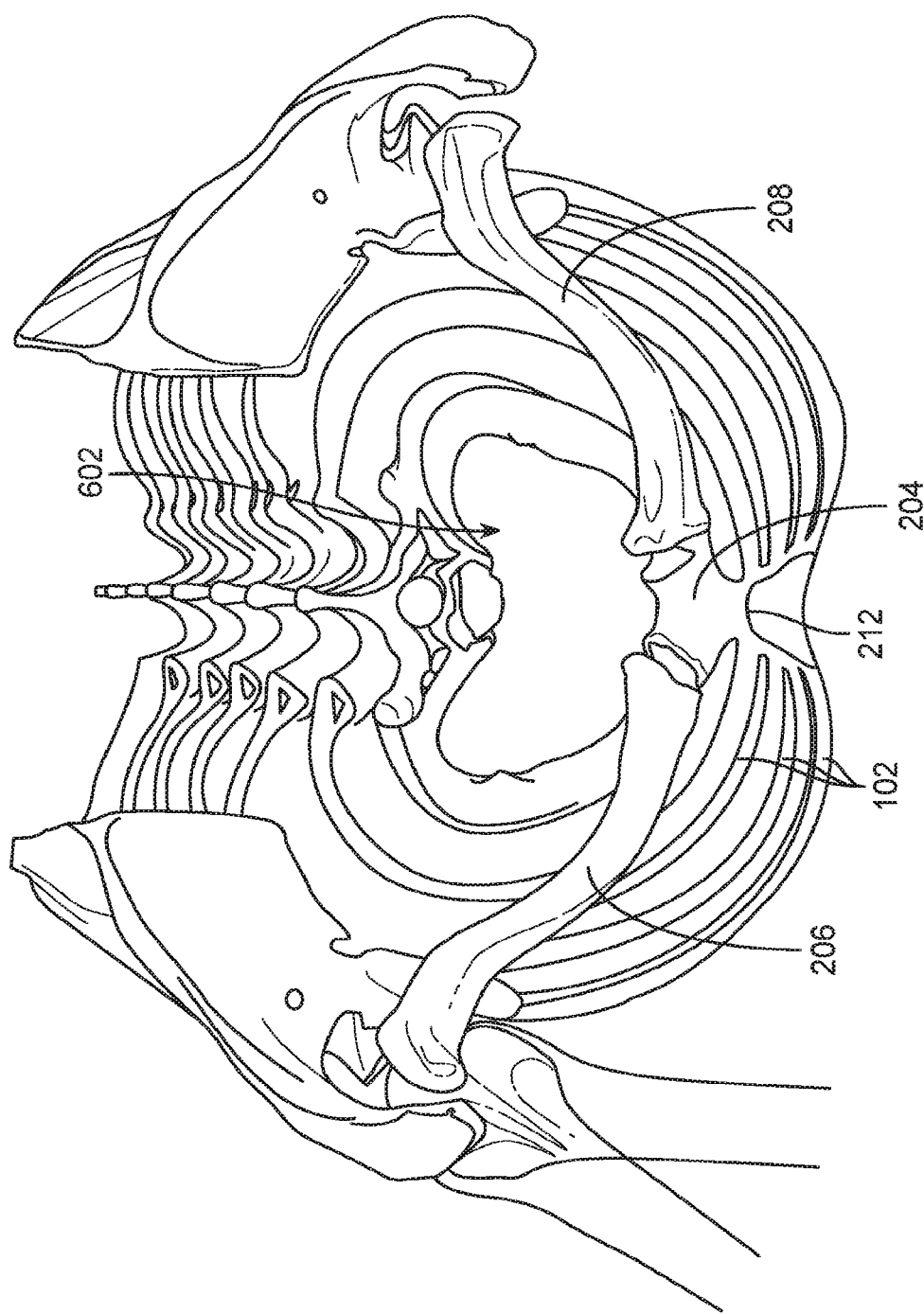
FIG. 6 shows an exemplary delivery route for a surgical instrument, in accordance with some embodiments.

FIG. 6 shows an exemplary delivery route for a surgical instrument (e.g. an intracardiac access device as described herein). As described herein, a distal portion of an instrument may be inserted through an incision in the suprasternal notch. The distal portion of the surgical instrument may be advanced into the body of the patient along the trachea through the superior thoracic aperture 602 (also referred to herein as the superior thoracic inlet) of the patient. The superior thoracic inlet 602 is the opening at the top of the thoracic cavity which essentially comprises a hole surrounded by a bony ring just below (i.e. inferior to) the neck. Insertion of the distal portion of the instrument through the incision in the suprasternal notch, and subsequent advancement of the instrument through the superior thoracic aperture 602 of the patient toward a left atrium of a heart of the patient may allow a user to access the heart of the patient without cutting a bone (e.g. the sternum 212, manubrium 204, or a rib 102) and/or the thoracic diaphragm 104, or spreading the ribs 102, thereby avoiding the complications associated with such injuries as described herein.

Referring again to FIGS. 4B-4F, after the distal portion of the surgical instrument 400 has been inserted into the body of the patient through the opening formed in the suprasternal notch, the distal portion of the surgical instrument 400 may be advanced along the trachea 130, through the thoracic aperture, and toward the left atrium of the patient's heart 110. The path along the trachea 130 may for example be a path anterior to the trachea 130. The distal portion of the surgical instrument 400 may be advanced through a mediastinal space of the body.

As described herein, by introducing the instrument 400 into the patient via the suprasternal notch, the roof of the left atrium may be accessed by the surgical instrument 400 without cutting bone or causing injury to other internal structures of the patient. This may be accomplished in part because the path between the suprasternal notch, through the superior thoracic aperture, and to the roof the heart 110 may be relatively straight. The instrument 400 may be configured to be advanced along a relatively straight path between the incision and the left atrium. A relatively straight path may be advantageous in at least some instances, for example when a mitral valve or mitral annulus of the heart 110 of the patient is to be accessed for a cardiac procedure as described herein.

The path through which the instrument traverses to reach the heart from the incision may for example have a length within a range of about 5 cm to about 25 cm, for example within a range of about 10 cm to about 25 cm, or within a range of about 5 cm to about 20 cm. For example, the path may be about 15 cm long. Correspondingly, the distal portion of the instrument which is inserted into the patient may have a length within a range of about 5 cm to about 25 cm to allow the instrument to reach the roof of the left atrium, for example within a range of about 15 cm to about 25 cm, or within a range of about 5 cm to about 20 cm. For example, the distal portion of the instrument may be about 20 cm long.

In preferred embodiments, the surgical instrument 400 may be inserted from the suprasternal incision to the left atrium along a path that passes outside the trachea 130, aorta 410, right pulmonary artery 420, and other vessels and structures within the mediastinum without entering, penetrating, cutting, puncturing, or otherwise injuring such vessels and structures (other than the left atrium).

In some embodiments, the surgical instrument 400 may be introduced into the patient via the suprasternal notch without accessing or penetrating the pleural cavities surrounding the lungs. By not penetrating the pleural cavities, the surgical instrument may avoid pneumothorax which can attend other approaches.

In some embodiments, the distal portion of the surgical instrument 400 may follow a path that extends through a space between the trachea 130 and the ascending aorta 410 (e.g. as shown in FIG. 4C).

In some embodiments, the distal portion of the surgical instrument 400 may follow a path that extends through a space between the trachea 130 and the aortic arch.

In some embodiments, the distal portion of the surgical instrument 400 may follow a path that extends through a space between the trachea 130 and a right branch of the pulmonary artery 420 (e.g. as shown in FIG. 4D). The distal portion of the surgical instrument 400 may first travel through a space between the trachea 130 and the ascending aorta 410 (e.g. as shown in FIG. 4C) before being further advanced into a space between the trachea 130 and the right branch of the pulmonary artery 420 (e.g. as shown in FIG. 4D). Alternatively, the distal portion of the surgical instrument 400 may be advanced into a space between the trachea 130 and the left branch of the pulmonary artery (not shown).

In some embodiments, the distal portion of the surgical instrument 400 may follow a path that extends through a space between the trachea 130 and a bifurcation of a main pulmonary artery.

In some embodiments, the distal portion of the surgical instrument 400 may be advanced along a path substantially parallel to a plane containing a longitudinal access of the trachea 130.

In some embodiments, the distal portion of the surgical instrument 400 may be advanced substantially parallel to a plane defined by a primary bronchus 430.

In some embodiments, the distal portion of the surgical instrument 400 may move (e.g. without puncturing) the right or left pulmonary artery 420 aside to reach the dome of the left atrium.

In some embodiments, the distal portion of the surgical instrument 400 may be advanced along a path that is superficial to the pretracheal fascia 440. In some embodiments, the distal portion of the surgical instrument 400 may be advanced along a path that is deep to the pretracheal fascia 440. Distal dissection in this plane may lead to the subcarinal space. The distance between the carina and the dome or the roof of the left atrium may depend on the size of the left atrium. For example, there may be an inverse correlation between the left atrial size and this distance.

In some embodiments, the instrument 400 may be rigid. In some embodiments, at least a portion of the instrument 400 may be flexible. Alternatively or in combination, at least a portion of the instrument 400 may be articulated. Alternatively or in combination, at least a portion of the instrument 400 may be steerable.

The instrument 400 may, for example, be relatively short and rigid. In some instances, a rigid device may be advantageous as it may be simpler to use than a device configured to flex, articulate, bend, rotate, or otherwise move within the patient. For example, rigid and/or short devices can be manipulated and positioned more accurately and quickly than elongated flexible instruments and catheters. This may be particularly important in beating heart procedures where movement of the heart makes the accurate and sustained positioning of such devices very challenging. A rigid device may also be easier to use during endoscopic procedures, as the orientation of the distal tip of the device does not change with respect to the endoscopic visual image.

In some embodiments, the instrument 400 may be steerable so as to avoid one or more internal structures of the patient (e.g. as shown in FIG. 4F). In some instances, it may be beneficial to steer the surgical instrument 400 around sensitive internal structures of the patient. The surgical instrument 400 may be configured to avoid, e.g. by steering, an internal structure comprising trachea 130, esophagus 450, aorta 410, superior vena cava 720, aortic arch 780, carotid artery 782, innominate artery, left recurrent laryngeal nerve, pulmonary artery 420 and/or a primary bronchus 430 of the patient.

Alternatively or in combination, the instrument 400 may be steerable to as to position the instrument within the heart 110 at a desired location or angle. The surgical instrument 400 may, for example, have a steerable distal end. The distal end may be configured to be steered before during advancement to the atrium from the skin incision so as to avoid internal structures of the patient or align the distal end with a particular access point on the heart, for example an extrapericardial location on the roof of the left atrium. Alternatively or in combination, the distal end may be configured to be steered after being inserted into an internal chamber of the heart, e.g. to align a procedural instrument or prosthesis at a desired distance and/or angle relative to an internal structure of the heart, for example a mitral valve leaflet, mitral annulus, or papillary muscles.

Figure 8:
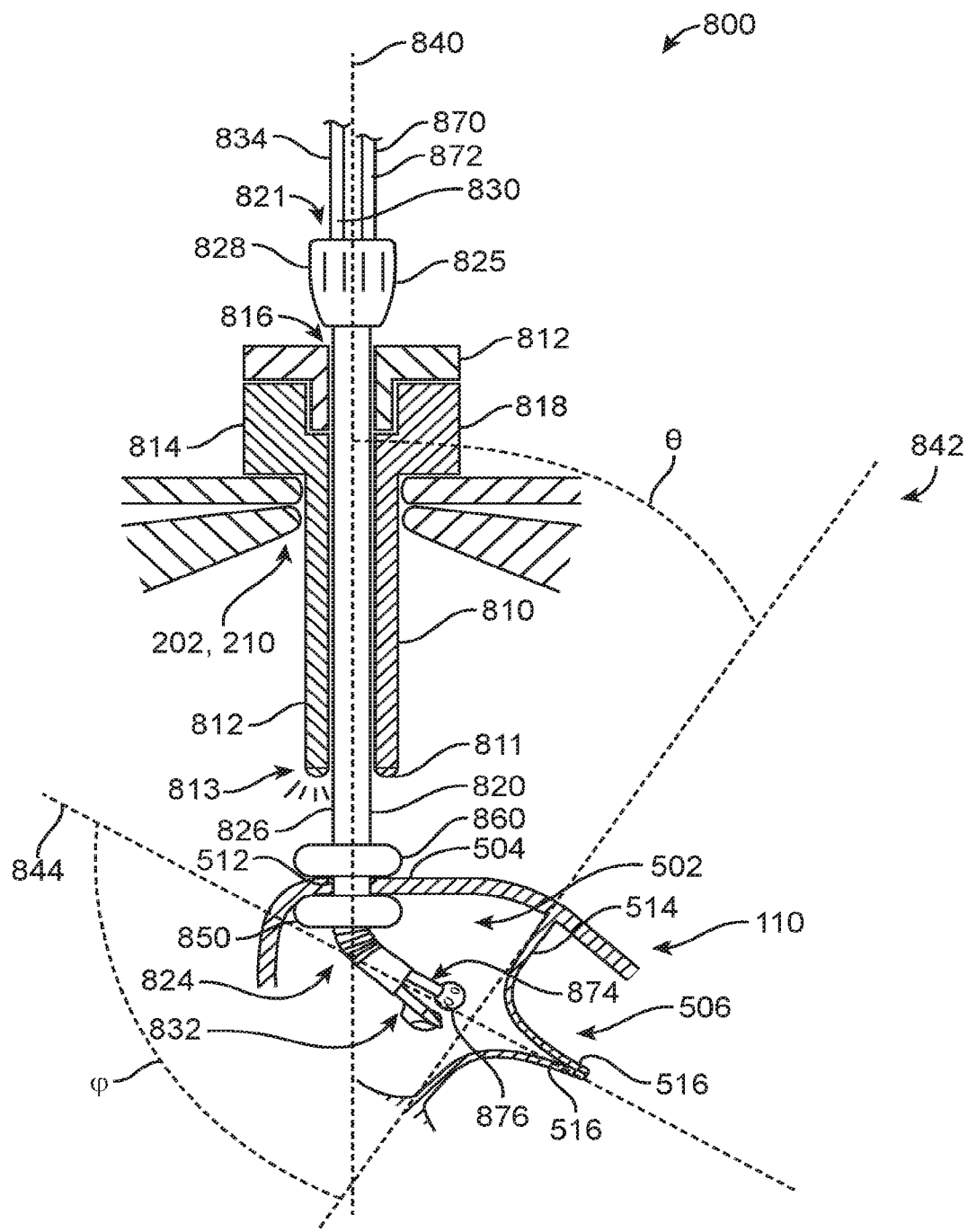
FIG. 8 shows an exemplary surgical system, in accordance with some embodiments.

In some embodiments, the surgical instrument 400 may be configured to fit within a working channel of a suprasternal access device (e.g. as shown in FIG. 8). The suprasternal access device may be placed into the opening in the suprasternal notch and advanced into the mediastinum. In some embodiments, the suprasternal access device may be advanced toward the heart 110 in the manner described herein with respect to the surgical instrument 400, e.g. inferiorly along the trachea 130 and between the aorta 410 and the trachea 130 and/or between the right pulmonary artery 420 and the trachea 130. Alternatively, the suprasternal access device may pass behind the aorta 410 and/or right pulmonary artery 420. The suprasternal access device may be advanced until a roof of the left atrium is visible through an optical channel or lens of the suprasternal access device. The distal portion of the surgical instrument 400 may then be inserted into the opening in the suprasternal notch by being inserted into a working channel of the suprasternal access device placed in the opening. The distal portion of the surgical instrument 400 may be advanced towards the heart through the working channel of the suprasternal access device. The distal portion of the surgical instrument may be advanced from the distal end of the suprasternal access device to contact the cardiac wall of the heart 110, optionally while being visualized through the optical channel or lens of the suprasternal access device. The suprasternal access device may optionally be used to visualize the mediastinal cavity and/or the heart of the patient while advancing the distal portion of the surgical instrument toward the heart as described herein.

In some embodiments, the surgical instrument 400 may be configured to fit within a working channel of a suprasternal access device such as a mediastinoscope. The mediastinoscope may be placed into the opening in the suprasternal notch and advanced into the mediastinum. In some embodiments, the mediastinoscope may be advanced toward the heart 110 in the manner described herein with respect to the surgical instrument 400, e.g. inferiorly along the trachea 130 and between the aorta 410 and the trachea 130 and/or between the right pulmonary artery 420 and the trachea 130. Alternatively, the mediastinoscope may pass behind the aorta 410 and/or right pulmonary artery 420. The mediastinoscope may be advanced until a roof of the left atrium is visible through the optical channel or lens of the mediastinoscope. The distal portion of the surgical instrument 400 may then be inserted into the opening in the suprasternal notch by being inserted into a working channel of a mediastinoscope placed in the opening. The distal portion of the surgical instrument 400 may be advanced towards the heart 110 through the working channel of the mediastinoscope. The distal portion of the surgical instrument 400 may be advanced from the distal end of the mediastinoscope to contact the cardiac wall of the heart 110, optionally while being visualized through the optical channel or lens of the mediastinoscope. The mediastinoscope may optionally be used to visualize the mediastinal cavity and/or the heart 110 of the patient while advancing the distal portion of the surgical instrument 400 toward the heart as described herein.

In some embodiments, the surgical instrument 400 may be configured to be inserted into the opening in the suprasternal notch by being advanced through the opening over a guide wire. The guidewire may first be inserted through the opening and advanced through the mediastinum to the left atrium along a path as described herein with respect to the surgical instrument 400. In some embodiments, the guidewire may be a steerable guidewire. In some embodiments, the guidewire may be advanced until it contacts the roof of the left atrium of the heart 110. In some embodiments, the tip of the guidewire may be advanced through the roof of the left atrium into the interior of the left atrium. The guidewire may include a pressure transducer or other sensor (e.g. similar to sensor 530 described herein) configured to detect when the tip is within the left atrium. The surgical instrument 400 may include a guidewire lumen, eyelet, tube, or the like configured to be slidably coupled to the guidewire. Alternatively, the guidewire may be passed through a working channel of the surgical instrument 400. The distal portion of the surgical instrument 400 may be advanced towards the heart 110 by sliding over the guide wire.

In some embodiments, the surgical instrument 400 may be configured to be inserted into the opening in the suprasternal notch by being advanced through a working channel in an endoscope. The endoscope may be inserted through the opening and advanced to the left atrium in the manner described herein with respect to the surgical instrument 400. The structures and vessels of the mediastinum may be viewed with the endoscope while it is advanced to facilitate navigation and minimizing trauma. The endoscope may be advanced until the left atrium can be seen, and/or until the endoscope reaches the left atrial dome. The distal portion of the surgical instrument 400 may be advanced towards the heart through a channel in the endoscope. Alternatively or in combination, an endoscope may be incorporated into the surgical instrument 400.

In some embodiments, the surgical instrument 400 may be configured to be inserted into the opening in the suprasternal notch by being advanced through the opening over an endoscope. The endoscope may be inserted through the opening and advanced to the left atrium in the manner described herein with respect to the surgical instrument 400. The structures and vessels of the mediastinum may be viewed with the endoscope while it is advanced to facilitate navigation and minimizing trauma. The endoscope may be advanced until the left atrium can be seen, and/or until the endoscope reaches the left atrial dome. The surgical instrument 400 may be configured to slidably couple with the endoscope, e.g. by passing the endoscope through a working channel of the surgical instrument 400. The distal portion of the surgical instrument 400 may be slidingly advanced towards the heart over the endoscope.

Referring again to FIG. 5B, any of the surgical instruments (e.g. suprasternal access devices, intracardiac access devices, and/or procedural devices) described herein, for example surgical instrument 520, may comprise a sensor 530. The sensor 530 may, for example, be coupled to a distal end of the surgical instrument 520 and configured to contact the cardiac wall of the heart 110 when the distal end of the surgical instrument 520 contacts the cardiac wall. The sensor 530 may comprise an electrical sensor, for example an electrode, an infrared sensor, a heat sensor, a reflectivity sensor, and/or a mechanical sensor, for example a pressure sensor or contact sensor. Alternatively or in combination, the surgical instrument 520 may have a visualization or imaging element e.g. CCD chip, a CMOS chip, or other video chip, an ultrasound transducer, or optical channel, lens, fiberoptic light cable, light emitting diode (LED), and/or illumination/light emission element. Alternatively or in combination, the surgical instrument 520 may be used in conjunction with an ultrasound probe, one or more pacing leads, or pressure monitoring catheters as are known to one of ordinary skill in the art.

The sensor 530 may be configured to confirm that the distal end of the surgical instrument 520 has made contact with, and/or remains in contact with, the cardiac wall. For example, the sensor 530 may be configured confirm that the surgical instrument 520 is in contact with the cardiac wall before an incision 512 is made in the cardiac wall to access an inner portion of the heart 110 as described herein. Alternatively or in combination, the sensor 530 may be configured to confirm that the surgical instrument 520 remains in contact with the cardiac while a cardiac procedure is being performed with the surgical instrument 520 or through the surgical instrument (e.g. when the surgical instrument comprises a channel extending therethrough configured to provide access to the heart 110 to a procedural instrument as described herein).

Referring again to FIG. 5C, the surgical instrument 520 may be advanced into contact with a cardiac wall of the heart 110 of a patient. The cardiac wall may for example be a wall of the left atrium 502. In some embodiments, the instrument 520 may be configured to contact the cardiac wall at a location on the dome 504 of the left atrium 502 outside a pericardium of the heart 110 (i.e. an extrapericardial location) as described herein. The surgical instrument 520 may be configured to form an opening 512 (e.g. make an incision, puncture, or the like) at a target location in the roof 504 of the left atrium 502 without penetrating the pericardium of the heart 110 as described herein. In at least some instances, accessing an interior portion of the heart via an extrapericardial opening 512 (also referred to herein as a second opening, an extrapericardial puncture, an extrapericardial incision, or an extrapericardial penetration) on the roof 504 of the left atrium 502 may avoid complications of conventional trans-pericardial surgical approaches such as unintentional injury to the heart wall and/or pericarditis. An extrapericardial puncture 512 may also be easier to form that a puncturing in other locations as the dome 504 of the left atrium 502 may relatively immobile, which may make access to the interior portion of the heart 110 easier and less complicated than entering at other locations (e.g. the left ventricular apex which is constantly moving and/or pulsing). Further, by eliminating the need to penetrate or open the pericardium, the need for specialized techniques and instruments for entering the pericardium safely may be obviated.

In some embodiments, the extrapericardial penetration 512 may be formed while the heart is beating. In some embodiments, the extrapericardial penetration 512 may be formed while the heart is slowed. In some embodiments, the extrapericardial penetration 512 may be formed while the heart is stopped. In some embodiments, the extrapericardial penetration 512 may be formed when the heart is on cardiopulmonary bypass.

If a stopped heart procedure is to be performed, the patient may be placed on cardiopulmonary bypass without further incisions in the chest by placing an endoaortic occlusion catheter into a femoral or iliac artery and advancing it into the ascending aorta, where a balloon may be expanded to occlude the aorta as will be known to one of ordinary skill in the art. A femoral venous cannula may be used to withdraw blood from the patient and deliver it to an external oxygenator and pump, from which blood may be returned to the patient via a femoral arterial cannula as will be known to one of ordinary skill in the art.

The surgical instrument 520 may, for example, be advanced into contact with the roof 504 of the heart 110 of a patient via an incision or opening in the suprasternal notch as described herein. The surgical instrument 520 may be configured to contact an extrapericardial portion of the roof 504 of the heart 110 of a patient.

Alternatively, the surgical instrument 520 may be advanced into contact with an extrapericardial portion of the roof 504 of the heart 110 of a patient via an incision or opening in another location. For example, an extrapericardial portion of the left atrial roof 504 of the patient's heart 110 may be accessed via a sternotomy, partial sternotomy, hemisternotomy, thoracotomy, minithoracotomy, or a video-assisted thoracoscopic (VATS) approach. Alternatively or in combination, an extrapericardial portion of the roof 504 of the patient's heart 110 may be accessed via an incision in the chest of a patient and through an intercostal space of the patient. Alternatively or in combination, an extrapericardial portion of the roof 504 of the patient's heart 110 may be accessed via video-assisted thoracoscopic (VATS) approach or a subxiphoid approach.

FIGS. 7A-7C show the extrapericardial location 700 (i.e. a location 700 without pericardium 702) of the roof 504 (also referred to herein as the dome) of the left atrium 502 of the heart 110. FIGS. 7A-7B show diagrams of the infero-posterior surface of the heart 110, highlighting the dome 504 of the left atrium 502. An extrapericardial portion 700 of the roof 504 of the left atrium 502 may be located in a space between the four ostia of the pulmonary veins 710 the superior vena cava 720, and the inferior vena cava 722. In some cases, the extrapericardial portion 700 may be an elongated rectangular, arch-shaped, or undulating space on the left atrial roof 504 approximately 1 cm to about 6 cm in length and 0.5 cm to about 3 cm in width, extending generally between the left superior pulmonary vein 710a and the right superior pulmonary vein 710b. An extrapericardial portion 700 of the roof 504 of the left atrium 502 may be bounded by the transverse sinus 730, the pulmonary venous recesses 740, the post caval recess 750, the left pulmonic recess 760, and the oblique sinus 770. An extrapericardial portion 700 of the roof 504 of the left atrium 502 may be located in a space between the ostia of the aortic root 780, the right pulmonary artery 420a, and the left pulmonary artery 420b. An extrapericardial portion 700 the roof 504 of the left atrium 502 may be bounded by the transverse sinus 730 and the superior pericardial recess 790. An extrapericardial portion 700 of the roof 504 of the left atrium 502 may be located in a space between the ostia of the four pulmonary veins 710, the intra-pericardial portion of the posterior wall of the left atrium 504, and the pulmonary arteries 420. The extrapericardial portion 700 of the roof 504 of the left atrium 502 may enlarge as the left atrium 504 enlarges. FIG. 7C shows a diagram of the heart 110, highlighting an exemplary target extrapericardial location 712 on the roof 504 of the left atrium 502. The target extrapericardial location 712 may be a target location through which the surgical instrument or other instrument(s) may access an interior portion of the heart 110 (e.g. via a puncture, an incision, or other opening 512 therein). The target location 712 (e.g. target location of an opening or incision or puncture in the cardiac wall) may be a space on the left atrial wall in a space between at least two pulmonary vein ostia 710. The target location 712 may be in the left atrial wall in a space between four pulmonary vein ostia 710. The target location 712 may be accessed by the surgical instrument as described herein without accessing, puncturing, or penetrating major vessels of the heart (e.g. the left carotid artery 782, the left subclavian artery 784, or the brachiocephalic trunk 786). The target location 712 may be accessed by the surgical instrument as described herein without access in the right atrium 704, the right ventricle 706, or the left ventricle 508 as described herein.

Referring again to FIGS. 5D-5E, at least a portion of the instrument 520, 522 (which may be any of the instruments described herein) may be advanced into an interior portion of the heart 110, for example the left atrium 502, through an extrapericardial penetration 512 (e.g. opening) in the roof 504 of the left atrium 502 as described herein. A distal portion of the instrument 520, 522 may be configured to be advanced through the extrapericardial penetration 512 into the left atrium 502 without penetrating the pericardium of the heart 110.

In some embodiments, a purse string suture may be placed in the left atrial wall prior to the creation of the extrapericardial penetration 512. In some embodiments, the left atrium 502 may be entered with a needle and/or or guidewire and dilator before the distal portion of the surgical instrument 520 is advanced through the extrapericardial penetration 512. A long needle may be advanced to puncture the dome 504 of the left atrium 502, with bright, red oxygenated blood exiting the needle indicating proper needle insertion into the left atrium 502, versus dark, blue blood indicative of entry into the right atrium. Once proper needle insertion position has been performed, a guidewire may be inserted through the needle into the left atrium 502, and the needle removed. A vascular hemostatic sheath with an inner dilator may be advanced along the guidewire into the left atrium 502. A pursestring suture may be placed, using a long pair of needle holders or thoracoscopic needle holders to hold a curved needle armed strand of suture. Multiple passes of the curved needle may be used to place the pursestring suture surrounding the emplaced vascular sheath. The free ends of the pursestring suture may be pulled through a length of flexible tubing and clamped under moderate tension to form a Rumel tourniquet that holds the sheath in place during the procedure. Upon completion of the procedure and removal of the vascular sheath, the pursestring suture may be tensioned and tied to close the left atrial entry site.

In some embodiments, the instrument 520 may be configured to perform a cardiac procedure as described herein. Alternatively or in combination, the instrument 520 may be removed after penetrating the cardiac wall and a procedural device (e.g. instrument 522 of FIG. 5E) may be inserted through the penetration 512 to perform the cardiac procedure as described herein. Alternatively or in combination, the instrument (e.g. instrument 524 of FIG. 5G) may be configured to provide access to the interior portion of the heart by a procedural device (e.g. instrument 528 of FIG. 5G) without first removing the instrument from the heart 110. For example, the surgical instrument 524 may comprise an access channel through which the procedural device 528 may be advanced into the heart. Alternatively or in combination, the procedural device 528 may comprise a channel configured to fit the surgical instrument 524 such that the procedural device 538 may be advanced towards the heart 110 over the surgical instrument 524.

Referring again to FIGS. 5F-5G, the surgical instrument 524 may comprise an intracardiac access device similar to any of the intracardiac access devices described herein. The surgical instrument 524 may comprise an elongate member. The elongate member 524 may have a distal portion configured to be inserted into a body of a patient and a proximal portion configured to remain outside the body of the patient when the distal end is inserted into the body of the patient. The distal portion of the elongate member 524 may be configured to contact the cardiac wall on the dome 504 of the left atrium 502 with the proximal portion extending out of the opening 202. The distal portion of the elongate member 524 may be configured to be advanced through an extrapericardial penetration 512 to access an internal chamber of the heart 110 as described herein.

In some embodiments, the elongate member 524 may be rigid. In some embodiments, at least a portion of the elongate member 524 may be flexible. Alternatively or in combination, at least a portion of the elongate member 524 may be articulated. Alternatively or in combination, at least a portion of the elongate member 524 of the instrument may be steerable.

The elongate member 524 may comprise a channel 540 extending therethrough from a distal end of the elongate member 524 to a proximal end of the elongate member 524. The channel 540 may be defined by an inner wall of the elongate member 524 having an inner diameter. In some embodiments, the elongate member 524 may comprise a cannula, a sheath, a tube, or a hollow shell.

The channel 540 of the elongate member 524 may be substantially straight from the proximal portion of the elongate member 524 to the distal portion of the elongate member 524. The channel 540 may provide a substantially straight access path from the opening (e.g. opening 202 of FIG. 2) to the internal chamber of the heart 110 for a procedural instrument (e.g. instrument 528) as described herein. In at least some instances, it may be advantageous to provide a substantially straight path from the opening to structures within the heart 110 such as the mitral valve 506, annulus 514, leaflets 516, and/or papillary muscles (e.g. 1308 of FIGS. 14A-14B). A substantially straight path may, for example, allow direct visualization of the heart 110 and instruments 528 (or any other procedural instrument or device described herein) during a cardiac procedure, and may allow the use of straight, rigid instruments which are more easily and accurately manipulated to perform such procedures as described herein. A substantially straight path may facilitate instrument manipulation and surgical hand-eye coordination, for example by facilitating direct visualization of the tissue. A substantially straight path may provide for direct access to internal structures of the body which may facilitate easier operative techniques.

The elongate member 524 may comprise an outer diameter within a range of about 5 mm to about 30 mm, for example within a range of about 5 mm to about 20 mm.

It will be understood by one of ordinary skill in the art that the outer diameter of the elongate member 524 may vary along at least a portion of its length. Alternatively, the outer diameter of the elongate member 524 may not vary along its length.

It will be understood by one of ordinary skill in the art that the outer diameter of the proximal portion of the elongate member 524, which may be located outside the patient during use, may be different from or similar to the outer diameter of the distal portion of the elongate member 524, which may be inserted into the patient during use.

The elongate member 524 may be configured to be fit within a working channel of a mediastinoscope as described herein. The elongate member 524 may, for example, have an outer diameter sized to fit within a working channel of a mediastinoscope, for example within a range of about 3 mm to about 30 mm, for example within a range of about 3 mm to about 15 mm, or within a range of about 10 mm to about 30 mm.

The elongate member 524 may comprise an inner diameter defining the channel within a range of about 1 mm to about 30 mm, for example within a range of about 1 mm to about 12 mm, or within a range of about 5 mm to about 30 mm.

The elongate member 524 may comprise a length within a range of about 5 cm to about 40 cm from the proximal end to the distal end, for example within a range of about 25 cm to about 40 cm, within a range of about 5 cm to about 20 cm, or within a range of about 5 cm to about 32 cm.

The distal portion of the elongate member 524 which is inserted into the patient may have a length within a range of about 5 cm to about 25 cm, for example within a range of about 15 cm to about 25 cm, or within a range of about 5 cm to about 20 cm, or within a range of about 5 cm to about 13 cm.

In some embodiments, the channel 540 of the elongate member 524 may be configured to allow one or more additional members to be slidably and/or removably disposed therein. The elongate member 524 may, for example, be configured to allow one or more of a penetration device 526, a procedural device 528, a visualization device, a prosthesis delivery device, and/or a suturing device to access the left atrium 504 as described herein.

The penetration device 526 may comprise a needle, a blade, or a trocar configured to penetrate the cardiac wall of the left atrium 502. For example, the surgical instrument may comprise a trocar 526 removably disposed in the channel 540 of the elongate member 524. The trocar 526 may be configured to make an extrapericardial penetration 512 as described herein. The trocar 526 may be configured to make the extrapericardial penetration 512 without penetrating the pericardium 702 of the heart 110. The trocar 526 may be configured to be removed from the channel 540 of the elongate member 524 after making the extrapericardial penetration 512. The trocar 526 may, for example, be removed from the channel 540 after advancing the distal portion of the surgical instrument 524 through the extrapericardial penetration 512 as described herein.

The procedural instrument 528 may be configured to perform a surgical procedure in the internal chamber of the heart 110. The surgical procedure may comprise at least one of mitral valve replacement, mitral valve repair, mitral annuloplasty, chordal repair, chordal replacement, leaflet resection, mitral replacement, leaflet coaptation, papillary repair, or papillary coaptation. The surgical procedure may alternatively comprise at least one of atrial appendage closure, atrial ablation, pulmonary vein ablation, septal defect closure, aortic valve repair, aortic valve replacement, tricuspid valve repair, tricuspid valve replacement, implantable cardiac defibrillator (ICD) implantation, pacemaker implantation, or placement of leads for ICD's or pacemakers, myocardial biopsy, or septectomy.

In some instances, the surgical procedure may be performed on a beating heart 110, without placing the patient on cardiopulmonary bypass. In some instances, the surgical procedure may be performed on a heart 110 which has been slowed but not stopped. In some instances, the surgical procedure may be performed on a stopped heart 110, wherein the patient may be placed on cardiopulmonary bypass.

The procedural instrument 528 may be configured to be advanced into the internal chamber of the heart 110 through the channel 540 of the elongate member 524 as described herein.

The procedural instrument 528 may be configured to extend through the opening 202 in the suprasternal notch 210 when the surgical procedure is performed. In some embodiments, the procedural instrument 528 may be coupled to a robotic manipulator disposed outside a chest of the patient. The robotic manipulator may, for example, comprise a robotic arm positioned above the suprasternal opening 202. Alternatively, the robotic manipulator may be disposed inside a chest of the patient. Procedural instrument end-effectors maybe advanced through the access channel 540 of the elongate member 524 to carry out the desired procedure in the internal chamber of the heart 110.

A distal portion of the procedural instrument 528 may be configured to be advanced into the internal chamber of the heart 110 through the extrapericardial penetration 512 (e.g. through the channel 540 of the elongate member 524). A proximal portion of the procedural instrument 528 may be coupled to a robotic manipulator disposed outside a chest of the patient as described herein.

Any of the suprasternal access devices, surgical instruments, or procedural instruments described herein may be configured to visualize the heart of the patient.

The surgical instrument and/or procedural instrument may be configured to visualize the heart of the patient while advancing the distal portion of the surgical instrument toward the heart. Visualization of the heart while advancing the distal portion of the surgical instrument toward the heart may aid in guiding the surgical instrument along the path between the opening and the heart. In some instances, visualizing the heart while advancing the instrument may help to determine when or if the distal end of the surgical instrument has reached and/or contacted the cardiac wall as described herein. Alternatively or in combination, the surgical instrument and/or procedural instrument may be configured to visualize an internal chamber of the heart after advancing the distal portion of the surgical instrument through the extrapericardial penetration.

Any of the surgical instruments described herein may, for example, comprise a visualization element coupled to the elongate member. The visualization element may comprise an optical channel extending through the elongate member and a lens aligned with the optical channel. In some instances, the channel for accessing the heart may comprise the optical channel. Alternatively or in combination, the surgical instrument may comprise an optical channel distinct from the access channel of the elongate member. The optical channel may be configured to directly view the heart while advancing the distal portion of the surgical instrument toward the heart. Alternatively or in combination, the optical channel may allow the user to directly view the heart of the patient through the opening after advancing the distal portion of the surgical instrument through the extrapericardial penetration. Direct visualization may be useful for several reasons. First, with the specialized adaptations disclosed herein it can permit direct visualization of intracardiac structures and instruments in a blood-filled field without the need to view a separate video screen. Further, direct visualization may facilitate easier hand-eye coordination than video endoscopy and can provide higher resolution and quality at a detailed level than echocardiography or fluoroscopy. Direct visualization may allow the user to enter the heart at a precise location, and/or to avoid inadvertent injury to the heart muscle, coronary arteries, and/or cardiac veins. Additionally, some users (e.g. surgeons) may prefer to see the operative field directly rather than on a viewing monitor as the spatial orientation may be better and direct visualization may offer a three-dimensional view that other visualization methods may not.

A blood displacement element may optionally be coupled to a distal end of the optical channel and configured to displace blood from the lens at the distal end of the optical channel to aid in visualization of internal structures of the heart. The blood displacement element may physically displace blood when positioned at or near a tissue or instrument of interest. For example, when placing a suture in an internal chamber of the heart, the blood displacement element may be positioned at or adjacent the suturing device (e.g. needle) to displace blood from the area at or around the tissue to be sutured and facilitate visualization of said tissue. The blood displacement element may comprise an enlarged optically transparent cylindrical, spherical, bullet-shaped, cone-shaped, or dome-shaped member, or a balloon, or the like. In some embodiments, the blood displacement element may be movable from a contracted delivery configuration of smaller cross-sectional size, to an expanded configuration of larger cross-sectional size. For example, the blood displacement element may comprise a balloon which may be inflated with saline or other optically transparent fluid to expand from the delivery configuration to the expanded configuration. Alternatively or in combination, the blood displacement element may comprise a fluid delivery channel extending through the elongate member adjacent the optical channel to an injection port adjacent the lens at the distal end. Injection of a fluid through the fluid delivery channel and injection port may displace blood adjacent the distal end of the optical channel to provide a field of view clear of blood.

The instrument may optionally comprise an eyepiece coupled to a proximal end of the optical channel and configured to allow direct visualization through the opening of internal structures of the body with the naked eye. Alternatively or in combination, the instrument may comprise a video camera mount optically-coupled to the optical channel near the proximal end of the instrument to allow connection of a video camera for video imaging through the optical channel.

Alternatively or in combination, the visualization element may comprise a CCD or CMOS or other video chip or camera coupled to the distal portion of the elongate member. The CCD or CMOS or other video chip or camera may be used to view the heart while advancing the distal portion of the surgical instrument toward the heart. Alternatively or in combination, the CCD or CMOS or other video chip or camera may be configured to image the internal chamber of the heart after advancing the distal portion of the surgical instrument through the extrapericardial penetration.

In any of the disclosed embodiments, the surgical instrument may be configured to provide illumination within the mediastinum and/or within the heart. The surgical instrument may include one or more optical fibers optically coupled to a light source at the proximal end and terminating at or near the distal end. Alternatively or in combination, the surgical instrument may have a light source near its proximal end optically coupled to the optical channel so that light may be transmitted through the optical channel to illuminate the field of view. In other embodiments, the surgical instrument may include one or more light emitting diodes at or near its distal end to provide illumination. In still other embodiments, a separate illumination device may be provided which can be introduced into the mediastinum and heart alongside the surgical instrument to provide illumination.

Alternatively or in combination, any of the surgical instruments or systems described herein may comprise a visualization device. The visualization device may comprise a mediastinoscope or an endoscope, for example. The visualization device may, for example, comprise an endoscope configured to be inserted into the channel of a mediastinoscope alongside the surgical instrument, or through a channel of the surgical instrument itself. Alternatively or in combination, the visualization device may comprise an endoscope or echocardiography probe configured to be inserted into the body through an opening other than that used by the elongate member, for example through an opening between ribs or in a sub-xiphoid location. Alternatively or in combination, the visualization device may comprise a transesophageal echocardiography probe. Alternatively or in combination, the visualization device may comprise a fluoroscope and one or more elements of the surgical instrument and/or procedural instrument may comprise one or more radiopaque markers.

The visualization device may be configured to view the heart while advancing the instrument through the mediastrinum and may help to determine when or if the distal end of the surgical instrument has reached and/or contacted the cardiac wall as described herein. Alternatively or in combination, the visualization device may be configured to visualize an internal chamber of the heart after advancing the distal portion of the surgical instrument through the extrapericardial penetration.

Any of the surgical instruments described herein may optionally comprise an anchoring element coupled to the proximal portion of the elongate member. The anchoring element may be configured to prevent inadvertent removal of the surgical instrument from the heart through the extrapericardial penetration, or inadvertent advancement toward or within the heart beyond a desired distance. The anchoring element may comprise a ring, flange, laterally-extending handles or wing-like elements, or other suitable structure on the proximal portion of the surgical instrument configured to engage the patient's body, surgical drapes, or other material adjacent the suprasternal opening. Alternatively the anchoring element may comprise an arm coupled to a stationary structure such as the operating table.

Any of the surgical instruments described herein may optionally comprise a retention element coupled to the distal portion of the elongate member. The retention element may be configured to prevent inadvertent removal of the surgical instrument through the extrapericardial penetration.

In some embodiments, the retention element may comprise a flange, a ring, an expandable wire basket, deployable wing-like elements, or a balloon. The retention element may have an undeployed configuration to aid in advancement of the instrument to the heart and through the atrial wall and a deployed configuration configured to resist inadvertent removal of the elongate member from a cardiac wall of the patient.

In some embodiments, the retention element may comprise one or more suction ports configured to secure the elongate member to the cardiac wall of the patient via negative pressure applied therethrough. In such embodiments, the surgical instrument may include one or more suction lumens in fluid communication with the suction ports through which negative pressure may be applied by a vacuum source outside the patient. The surgical instrument may further include a soft, conformable sealing member, e.g. suction cup or rubber flange, surrounding the one or more suction ports to conform to the heart wall, reduce trauma, and maintain an air-tight seal.

Any of the surgical instruments described herein may optionally comprise an external sealing element coupled to the distal end of the elongate member. The external sealing element may be configured to create a circumferential seal between the cardiac wall adjacent the extrapericardial penetration and the distal portion of the surgical instrument. Alternatively or in combination, the external sealing element may be configured to hemostatically seal the extrapericardial penetration circumferentially around the surgical instrument to inhibit leakage of blood while the heart is beating.

In some embodiments, the sealing element may be configured to work in combination with a pursetring suture in the cardiac wall circumferentially around the extrapericardial penetration around the distal portion of the surgical instrument. The pursetring suture may be applied to the cardiac wall prior to or after insertion of the surgical instrument into the extrapericardial penetration. The pursestring suture may be tightened around the surgical instrument after the instrument has been inserted into the extrapericardial penetration in order to circumferentially seal the cardiac wall and the distal portion of the surgical instrument.

In some embodiments, the sealing element may comprise a compression flange or a balloon configured to form a hemostatic seal around the distal portion of the elongate member when the elongate member is advanced through the extrapericardial penetration into the internal chamber of the heart. The sealing element may have a low-profile undeployed configuration to aid in advancement of the instrument to the heart and an expanded deployed configuration configured to form a hemostatic seal around the distal portion of the elongate member when the elongate member is advanced through the extrapericardial penetration into the internal chamber of the heart. In embodiments utilizing a balloon, the surgical instrument may include an inflation lumen in fluid communication with the balloon through which a fluid may be introduced to inflate the balloon. Mechanically deployable retention and/or sealing structures may include an actuation mechanism such as one or more pull wires extending through one or more lumens in the surgical instrument.

In some embodiments, the surgical instrument may include an internal sealing element to inhibit blood loss through any channels in the surgical instrument. The internal sealing element may comprise a hemostatic valve disposed in the one or more channels of the elongate member configured to inhibit blood loss therethrough. The hemostatic valve may preferably be configured to inhibit blood loss while the heart is beating. The hemostatic valve may, for example, comprise a duck bill valve or a three leaflet valve.

In some instances, a sealing element may not be necessary to inhibit leakage of blood as the pressure in the left atrium may not be sufficient to cause substantial leakage through the extrapericardial penetration.

In some embodiments, the retention element may act as a sealing element to hemostatically seal the extrapericardial penetration circumferentially around the surgical instrument while also preventing inadvertent removal of the surgical instrument through the extrapericardial penetration. In some embodiments, actuation of the retention element from the undeployed configuration to the deployed configuration may form the hemostatic seal.

In some embodiments, a biological glue or sealant may be used to seal the extrapericardial penetration around the surgical instrument. The biological glue may for example comprise a cyanoacrylate glue (e.g. HistoAcryl®, Omnex™), a fibrin glue (e.g. Evicel®, Tisseel, Hemaseel APR™, Beriplast®, Vivostat®, etc.), an bovine albumin-glutaraldehyde glue (e.g. BioGlue®), a collagen-based sealant (e.g. Colgel, Helitene®, Avitene™), a gelatin-based sealant (e.g. FloSeal), a thrombin-based sealant (e.g Thrombin, Thrombogen, Thrombostat), a collagen-thrombin-based sealant (e.g. CoStasis®) a polysaccharide-based sealant (e.g. Surgicel®, Oxycel®), a polyethylene glycol seal (e.g. CoSeal, DuraSeal) or the like as will be known to one of ordinary skill in the art.

FIG. 8 shows an exemplary surgical system 800. The system may comprise a suprasternal access device 810, a surgical access device 820 (also referred to herein as an intracardiac access device or surgical instrument) positionable through the suprasternal access device 810, and a procedural instrument 830 (also referred to herein as an interventional device) positionable through the intracardiac access device. The intracardiac access device 820 may comprise any of the surgical access devices described herein, for example an elongate member having a channel extending therethrough as described herein. The procedural instrument 830 may comprise any of the procedural instruments described herein. In some embodiments, the suprasternal access device 810 may comprise a mediastinoscope as described herein. In other embodiments, the suprasternal access device 810 may not be a mediastinoscope. For example, the suprasternal access device 810 may be configured to extend within the body much closer to the heart than a traditional mediastinoscope, and may include various other features such as optics or video, illumination elements, an insufflation channel, and/or steerable or deformable sections.

In some embodiments, the suprasternal access device 810 may be substantially rigid and/or straight, which may be advantageous in at least some instances as described herein with respect to the surgical instrument. In some embodiments, at least a portion of the suprasternal access device 810 may be flexible. Alternatively or in combination, at least a portion of the suprasternal access device 810 may be articulated. Alternatively or in combination, at least a portion of the suprasternal access device 810 may be steerable.

The suprasternal access device 810 may comprise a distal portion 812 and a proximal portion 814. The distal portion 812 may be configured to be inserted into the patient's body through an incision 202 in the suprasternal notch 210 as described herein. The proximal portion 814 may be configured to remain outside the body of the patient when the distal portion 812 is inserted into the body of the patient. A working channel 816 may extend between a distal end and a proximal end of the suprasternal access device 810.

The proximal, external portion 814 of suprasternal access device 810 may comprise an anchoring element 818 configured to prevent inadvertent removal of the suprasternal access device 810 or inadvertent advancement toward the heart 110 beyond a desired distance. The anchoring element 818 may comprise a ring, flange, laterally-extending handles, wing-like elements, adhesive patches, circular sandbags, or other suitable structure on the proximal portion 814 of the suprasternal access device 810 configured to engage the patient's body, surgical drapes, operating table, or other material adjacent the suprasternal opening 202. Alternatively the anchoring element 818 may comprise a coupling mechanism for coupling to a mechanical arm that may be anchored to a stationary structure such as the operating table.

The anchoring element 818 may for example comprise the proximal portion 814 of the suprasternal access device 810 itself. In some embodiments, the proximal portion 814 of the suprasternal access device 810 may be sized to prevent insertion of the proximal portion 814 of the suprasternal access device 810 into the opening 202. The proximal portion 814 of the suprasternal access device 810 may, for example, have an outer diameter greater than the diameter/length of the suprasternal opening or incision 202 as shown in FIG. 8. The proximal portion 814 of the suprasternal access device 810 may, for example, have an outer diameter within a range of about 5 cm to about 8 cm.

Alternatively or in combination, the proximal portion 814 the suprasternal access device 810 may comprise a laterally-extending handle angled relative to the access path (e.g. at a right angle) which may act as an anchor and prevent insertion of the suprasternal access device 810 past the angled handle.

Alternatively or in combination, the anchoring element 818 may comprise an adhesive patch adhered the patient's skin at the opening 202. The inner diameter of the opening in the adhesive patch may comprise ridges, teeth, or the like configured to lock onto mating ridges, teeth, or the like, respectively, on the posterior surface of the suprasternal access device 810.

The distal portion 812 of the suprasternal access device 810 may be configured to extend from an opening 202 in or adjacent a suprasternal notch 210 of the patient, through a superior thoracic aperture of the patient, and into a mediastinum of the patient as described herein.

In some embodiments, the distal portion 812 of the suprasternal access device 810 may be configured to be positioned above the cardiac wall on the roof 504 of the left atrium 502. For example, the distal portion 812 of the suprasternal access device 810 may be configured to be positioned within a range of about 0.1 cm to 2 cm above the extrapericardial penetration site 512 in the left atrial dome 504, for example within a range of about 1 cm to about 2 cm above the extrapericardial penetration site 512 in the cardiac wall. Alternatively, the distal portion of the suprasternal access device 810 may be configured to be positioned in contact with the cardiac wall.

The distal portion 812 of the suprasternal access device 810 may have a length within a range of about 5 cm to about 25 cm to allow the suprasternal access device 810 to reach, or nearly reach, the roof 504 of the left atrium 502, for example within a range of about 15 cm to about 25 cm, or within a range of about 5 cm to about 20 cm, or within a range of about 15 cm to about 20 cm. For example, the distal portion 812 of the suprasternal access device 810 may be about 20 cm long.

In some embodiments, the suprasternal access device 810 may comprise a retention element 822 configured to prevent inadvertent removal of the intracardiac access device 820 from the heart 110 or inadvertent advancement toward or within the heart 110 beyond a desired distance. The retention element 822 may comprise ring, flange, laterally-extending handles, wing-like elements, adhesive patches, circular sandbags, or other suitable structure on the proximal portion 814 of the suprasternal access device 810 configured to engage the intracardiac access device 820 adjacent the suprasternal opening 202. The retention element 822 may, for example, comprise a clamping device coupled to the proximal portion 814 of the suprasternal access device 810 configured to couple the suprasternal access device 810 and the intracardiac access device 822 to one another and restrict or prevent relative movement therebetween.

The suprasternal access device 810 may comprise one or more working channels 816 therethrough. In some embodiments, the suprasternal access device 810 may comprise one working channel 816 configured to allow an intracardiac access device 820 to access the heart 110 therethrough. The working channel 816 may be configured to hold additional devices, in combination with the intracardiac access device 820, such as a visualization device, a penetration device, and/or an illumination device as described herein. In some embodiments, the suprasternal access device 810 may comprise a second working channel, or more, configured to hold the additional devices, for example with one device per working channel.

The suprasternal access device 810 may have a cross-sectional shape configured to facilitate access to the heart 110 through an incision 202 in the suprasternal notch 210 and maximize the space available for manipulation of instruments and direct visualization. The cross-sectional shape may for example be circular, ellipsoidal, ovoid, or any other shape as desired by one of ordinary skill in the art. In some instances, a distal portion 812 of the suprasternal access device 810 may comprise a curved wall or blade forming an incomplete cylinder or channel, e.g. the cross-sectional shape may be a curve or arc surrounding only part of the working channel, leaving a lateral side of the working channel 816 open to the working site.

The suprasternal access device 810 may comprise a visualization element 811 as described herein. The visualization element 811 may, for example comprise one or more of a CCD chip, a CMOS chip, a video chip, an ultrasound transducer, an optical channel, or a lens. The visualization element 811 may, alternatively or in combination, comprise an illumination source 813 such as a fiber optic light cable, a light emitting diode (LED), or an illumination element as described herein The suprasternal access device 810 may comprise a blood displacement element coupled to the distal end thereof and configured to displace blood from the visualization element 811, for example an endoscope or a lens at the distal end of an optical channel running through the suprasternal access device 810, to aid in visualization of internal structures of the heart 110 as described herein.

In some embodiments, the suprasternal access device 810 may comprise an ultrasound transducer configured to image the heart 110 during the entire procedure. The ultrasound transducer may comprise a 3D echocardiography device.

The suprasternal access device 810 may facilitate access to the heart 110 by the intracardiac access device 820 and the procedural device 830 by acting as a tissue retractor and providing an unobstructed path to the heart 110 (e.g. via the working channel 816). The suprasternal access device 810 may retract the tissues along the path between the suprasternal notch 210 and the left atrium 502 described herein, thereby enabling easy visualization and manipulation with the other devices disposed therein.

The suprasternal access device 810 may comprise a pacing wire or pacing element (e.g. electrode, lead) to pace the heart during surgical procedures, as described herein. The pacing wire or element may be temporarily placed in contact with cardiac tissue during surgical procedures.

The suprasternal access device 810 may comprise a gas (e.g. carbon dioxide) insufflation port. In some instances, it may be beneficial to insufflate the chest cavity and/or exclude oxygen from the chest cavity and heart while advancing the suprasternal access device 810, advancing the intracardiac access device 820, and/or performing the surgical procedure with the procedural device 830. In some embodiments, the suprasternal access device 810 may further comprise a sealing element, for example a balloon, positioned adjacent the insertion site (e.g. incision 202) configured to seal the opening and allow insufflation of the chest cavity with carbon dioxide from the insufflation port.

The distal, internal portion 812 of the suprasternal access device 810 may have an inner diameter within a range of about 1 cm to about 5 cm, for example within a range of about 3 to about 4 cm. The distal portion 812 of the suprasternal access device 810 may be sized allow insertion of the intracardiac access device 820 and provide room for the distal tip 824 of the intracardiac access device 820 to angulate upon entry into the left atrium 502 as described herein.

In some embodiments, the suprasternal access device 810 may be substantially rigid and/or straight, which may be advantageous in at least some instances as described herein with respect to the surgical instrument. In some embodiments, at least a portion of the suprasternal access device 810 may be flexible. Alternatively or in combination, at least a portion of the suprasternal access 810 device may be articulated. Alternatively or in combination, at least a portion of the suprasternal access device 810 may be steerable.

The distal portion 826 of the intracardiac access device 820 may be configured to extend from the distal portion 812 of the suprasternal access device 810 and through an extrapericardial penetration 512 through a cardiac wall at a first location on a dome 504 of the left atrium 502 of the patient to access an internal chamber of the heart 110, the first location being outside a pericardium of the heart 110. The intracardiac access device 820 may be configured to extend through the extrapericardial penetration 512 in the cardiac wall without penetrating the pericardium of the heart 110.

The distal portion 826 of the intracardiac access device 820 may be configured to facilitate access to the mitral valve 506. In at least some instances, the mitral valve annulus 514 maybe at an oblique angle θ relative to the device's path of entry (e.g. along an axis 840 from the suprasternal notch 210 to the atrial access point 512) through the roof 504 of the left atrium 502. In some embodiments, a longitudinal axis 844 of the distal tip of the intracardiac access device 820 may be positionable at an angle φ relative to a plane 842 containing the mitral annulus 514 when the intracardiac access device 820 is positioned in the internal chamber of the left atrium 502 as described herein. In some embodiments, the distal tip of the intracardiac access device may be positionable generally orthogonal to the plane 842 containing the mitral annulus 514 when the intracardiac access device 820 is positioned in the internal chamber of the left atrium 502 as described herein.

In some embodiments, the distal portion 826 of the intracardiac access device 820 may comprise a pre-formed curved distal tip 824. Distal tip 824 may be connected to the proximal portion by a flexible joint to allow distal tip 824 to be oriented at various angles relative to the proximal portion and/or formed into a straight configuration aligned with axis 840 for introduction into the heart. Distal tip 824 may be resiliently biased into a curved or angled configuration so as to return to the desired angle after introduction. In some embodiments, the distal portion 826 of the intracardiac access device 820 may comprise a steerable distal tip 824 as described herein. In some embodiments, the distal tip 824 of the intracardiac device 820 may be configured to angle (e.g. via a pre-formed curve or a steerable tip) to an oblique angle θ relative to the angle of entry (e.g. relative to the axis 840) into the internal chamber of the heart 110 through the extrapericardial penetration 512. The distal tip 824 may be steerable to angle relative to a longitudinal axis 840 of the intracardiac device 820. The distal tip 824 may for example be steerable to angle relative to the longitudinal axis 840 of the intracardiac device 820 within a range of about 0 to about 60 degrees, for example within a range of about 30 to about 60 degrees to facilitate access to the mitral valve 506. The distal tip 824, from the articulated joint or preformed curve to the distal end, will preferably have a length of about 1 to 5 cm.

The intracardiac access device 820 may comprise a steering knob 825 coupled to the proximal portion 828 of the intracardiac access device 820. The steering knob 825 may be configured to control the steerable tip 824 of the intracardiac access device 820, e.g. by tensioning steering wires coupled to the distal tip 824.

The distal portion 826 of the intracardiac access device 820 may have a length extending from the opening 202 in or adjacent a suprasternal notch 210 of the patient, through a superior thoracic aperture of the patient, and through the extrapericardial penetration 512 into the internal chamber of the heart 110. In exemplary embodiments, this length may be about 10 to 25 cm, depending on the size of the patient and anatomical characteristics.

The distal end 826 of the intracardiac access device 820 may comprise a retention element 850 as described herein. The retention element 850 may have an undeployed configuration and a deployed configuration. The retention element 850 may be configured to resist inadvertent removal of the intracardiac device 820 from a cardiac wall of the patient. For example, the intracardiac access device 820 may comprise a balloon retention element 850 coupled to the distal end 826 of the intracardiac access device 820 and configured to be disposed within the interior chamber of the heart 110. Inflation of the balloon 850 may prevent inadvertent removal of the intracardiac access device 820 from the heart 110 as described herein.

The intracardiac access device 820 may comprise an internal sealing element 860 configured to inhibit blood loss through the channel of the intracardiac access device 820 as described herein.

The intracardiac access device 820 may comprise a sealing element 860 coupled to the distal end 826 of the intracardiac device 820 as described herein. The sealing element 860 may be configured to be actuated from an undeployed configuration to a deployed configuration to form a hemostatic seal around the distal portion 826 of the intracardiac device 820 when the intracardiac device 820 is advanced through the extrapericardial penetration 512 into the internal chamber of the heart 110 as described herein. The sealing element 860 may for example comprise a balloon disposed on the cardiac wall outside the extrapericardial penetration 512 as shown in FIG. 8.

The intracardiac device 820 may comprise an elongate member having a distal portion 826 configured to be inserted into a body of a patient through the working channel 816 of the suprasternal access device 810 and a proximal portion 828 configured to remain outside the body of the patient when the distal portion 826 is inserted into the body of the patient as described herein. The elongate member 820 may comprise an inner wall defining a channel 821 therein, the channel 821 extending between a distal end and a proximal end of the elongate member 820 and being configured to receive a procedural device 830 for performing a surgical procedure therein.

The intracardiac access device 820 may comprise a pacing wire or pacing element (e.g. electrode, lead) to pace the heart during surgical procedures, as described herein. The pacing wire or element may be temporarily placed in contact with cardiac tissue during surgical procedures.

The procedural device 830 may comprise any of the procedural devices described herein.

In some embodiments, the procedural device 830 may comprise an annuloplasty band or annuloplasty ring as described herein, and/or an instrument configured to deliver an annuloplasty band or ring to the native mitral annulus 514 in the left atrium 502. In some embodiments, the procedural device 830 may be configured to attach an annuloplasty device (e.g. ring or band) to a mitral annulus 514 of the heart 110 as described herein.

In some embodiments, the procedural device 830 may comprise a prosthetic valve and/or a delivery system for a prosthetic valve.

In some embodiments, the procedural device 830 may be configured to attach an artificial chord to a mitral leaflet 516 of the heart 110 as described herein.

In some embodiments, the procedural device 830 may be configured to apply a suture or other fixation/anchoring device to heart tissue on or near a mitral valve 506 of the heart 110, or to tissue elsewhere in the heart 110 or great vessels, as described herein.

In some embodiments, the proximal end 834 of the procedural device 830 may be configured to extend out of the proximal end 828 of the intracardiac access device 820 and/or the proximal end 814 of the suprasternal access device 810 where it can be manipulated by the surgeon, as shown in FIG. 8.

The procedural device 830 may comprise a pacing wire or pacing element (e.g. electrode, lead) to pace the heart during surgical procedures, as described herein. The pacing wire or element may be temporarily placed in contact with cardiac tissue during surgical procedures.

The system 800 may optionally comprise a visualization element or device 870 as described herein.

In some embodiments, the visualization element or device 870 may be configured to permit direct visualization of the internal chamber of the heart 110 through blood as described herein. The visualization element 870 may have an optical channel with an eyepiece at its proximal end 872 to allow the user to view directly through the optical channel into the heart 110. Alternatively or in combination, a video camera coupling may be provided at the proximal end 872 to allow videography through the optical channel.

In some embodiments, the visualization element 870 may comprise a blood displacement element 876 at its distal end 874 as described herein.

The visualization element 870 may comprise any combination of visualization elements or devices described herein. In some embodiments, the visualization element 870 may comprise an endoscope disposed within the channel 821 of the intracardiac access device 820 as shown in FIG. 8. Alternatively or in combination, the visualization element 870 may comprise an optical channel and a lens. Alternatively or in combination, the visualization element 870 may comprise a CCD chip or other video chip as described herein.

In some embodiments visualization element 870 (e.g. endoscope) may be configured to be simultaneously positioned in the channel 821 of the intracardiac access device 820 with the procedural device 830.

In some embodiments, the visualization element 870 may be configured to be positioned within the channel 821 of the intracardiac access device 820 independently of the procedural device 830.

In some embodiments, the proximal end 872 of the visualization element 870 may be configured to extend out of the proximal end 828 of the intracardiac access device 820 and/or the proximal end 814 of the suprasternal access device 810 as shown in FIG. 8.

In some embodiments, all or a portion of the system 800 components may be contained in a sealed, sterile package.

In some embodiments, a surgical instrument kit may comprise one or more devices described herein disposed within a sealed sterile package. The kit may comprise a suprasternal access device 810 and an intracardiac access device 820 in a sealed sterile package. The kit may comprise an intracardiac access device 820 and a procedural device 830 in a sealed sterile package. The kit may comprise an intracardiac device 820, a procedural device 830, and a visualization element or device 870 in a sealed sterile package. The kit may comprise any of the devices or elements described herein, or any of combination of the devices or elements described herein, in a sealed sterile kit.

Figure 9A:
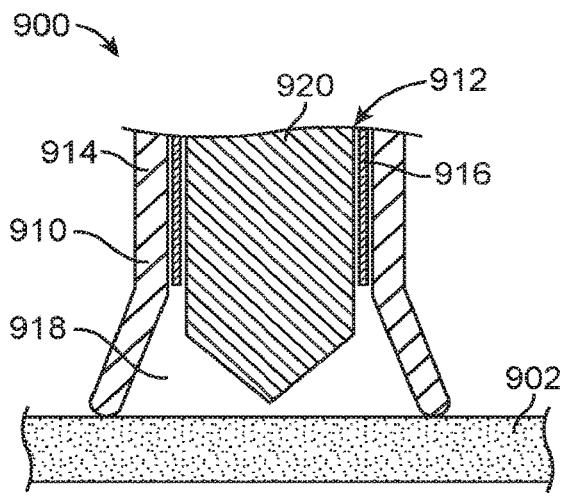
FIGS. 9A-9D show the distal end of an exemplary surgical instrument, in accordance with some embodiments.

FIGS. 9A-9D show the distal end of an exemplary surgical instrument 900, in accordance with some embodiments. The surgical instrument may comprise an elongate member 910 having a channel 912 extending therethrough as described herein. The elongate member 910 may be configured to be advanced from a suprasternal opening through the mediastinum to contact a cardiac wall 902 of the left atrium 502 as described herein, for example to an extrapericardial location 512 on the dome 504 of the left atrium 502 as described herein. The elongate member 910 may comprise a cutting tool 920, for example a trocar, disposed within the channel 912 and configured to make an extrapericardial penetration 512 through the cardiac wall 902 of the atrial dome 504 without penetrating the pericardium or entering the pericardial space surrounding the heart as described herein. The elongate member 910 may optionally comprise one or more of an outer cannula 914, a suction port 918, or an inner cannula 916. In some embodiments, the elongate member 910 may comprise external cannula 914 and an internal cannula 916 slidably disposed therein. The inner wall of the internal cannula 916 may define the channel 912 extending through the elongate member 910. A penetrating instrument 920, such as a trocar, may be removably positionable in the channel 912. The distal end of the external cannula 914 may be advanced into contact with the atrial wall 902 as described herein. The external cannula 914 may optionally be held in place on the atrium surface 902 when negative pressure (e.g. suction) is applied to the cardiac wall 902 via an annular suction port 918 disposed between the inner cannula 916 and the outer cannula 914 as shown in FIG. 9A. The distal end of the outer cannula 914 may optionally be flared to provide a broader area of contact with the heart wall 902, thereby distributing forces and minimizing trauma. In some embodiments, a compliant sealing member such as a suction cup may be coupled to the distal end to minimize trauma and facilitate sealing with the heart wall 902.

Figure 9B:
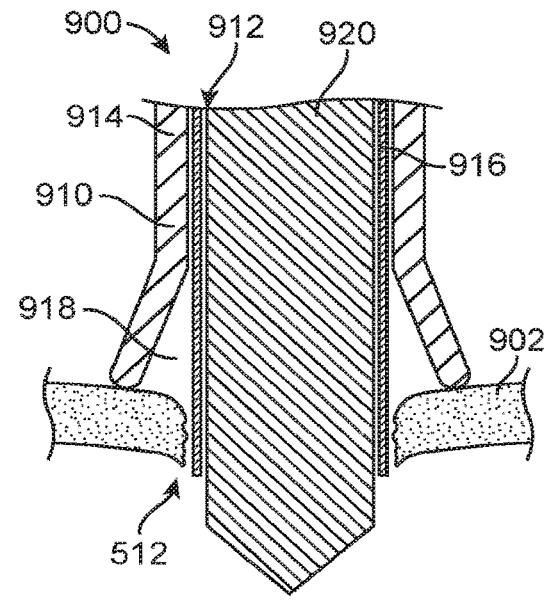
Figure 9C:
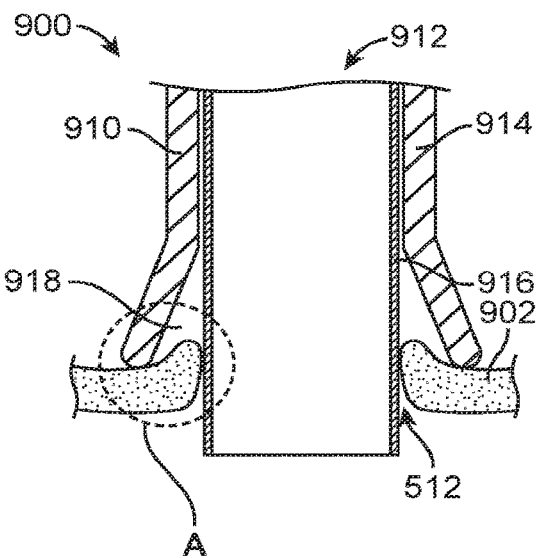
Figure 9D:
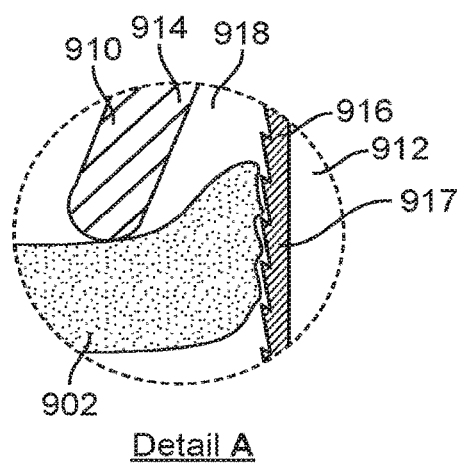

FIG. 9B shows puncture of the trocar 920 through the atrial wall 902 to form an extrapericardial penetration 512 as described herein. The trocar 920 may be advanced relative to the outer cannula 914 so as to penetrate through the heart wall 902 into an interior chamber of the heart. A distal portion of the internal cannula 916 may be configured to be advanced from the distal end of the external cannula 914 and through the extrapericardial penetration 512 into the interior heart chamber. The trocar 920 may then be removed from the channel 912 in the internal cannula 916. The distal end of the external cannula 914 may be configured to remain in contact with the cardiac wall 902 outside the extrapericardial penetration 512. In some embodiments, the atrial wall 920 edges of the extrapericardial penetration 512 may be wedged between distal ends of the external and internal cannulas 814, 816 to create a seal, as shown in FIGS. 9C-9D. In some embodiments, an external sealing member (not shown), such as a flange or annular balloon, may be provided on a distal portion of the internal cannula 916 to provide a seal and/or enhance retention with the inner wall of the heart. The suction port 918 may act as a retention element configured to seal a distal end of the external cannula 914 against the cardiac wall 902 when negative pressure is applied to the cardiac wall 902 via the suction port 918. The internal cannula 916 may optionally comprise a barbed texture 917 as shown in FIG. 9D to provide added grip and further resist inadvertent removal of the elongate member 910 from a cardiac wall 902 of the patient. The channel 912 of the internal cannula 916 may provide a pathway for additional instruments to access the internal chamber of the heart as described herein.

Figure 10A:
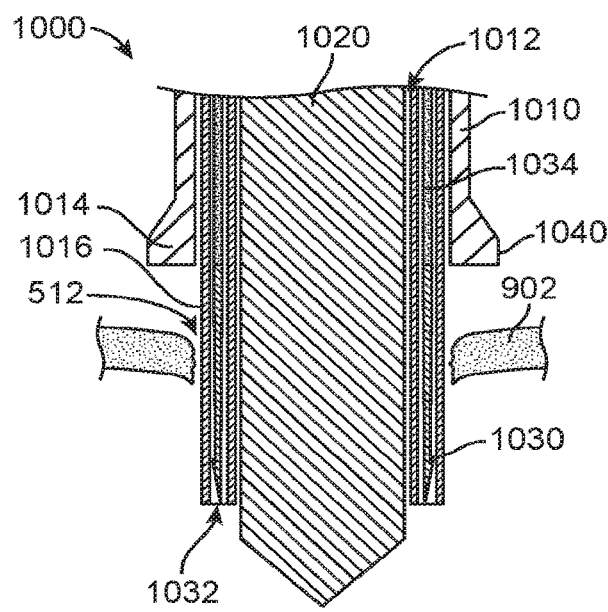
FIGS. 10A-10D show the distal end of another exemplary surgical instrument, in accordance with some embodiments.

FIGS. 10A-10D show the distal end of another exemplary surgical instrument 1000, in accordance with some embodiments. The surgical instrument 1000 may comprise an elongate member 1010 having a channel 1012 extending therethrough as described herein. The elongate member 1010 may be configured to be advanced from a suprasternal opening through the mediastinum to contact a cardiac wall 902 of the left atrium 502 as described herein, for example to an extrapericardial location 512 on the dome 504 of the left atrium 502 as described herein. The elongate member 1010 may comprise a cutting tool 1020, for example a trocar, removably disposed within the channel 1012 and configured to make an extrapericardial penetration 512 through the cardiac wall 902 of the atrial dome 504 without penetrating the pericardial space around the heart as described herein. In some embodiments, the elongate member 1010 may comprise external cannula 1014 and an internal cannula 1016 slidably disposed therein. The inner wall of the internal cannula 1016 may define the channel 1014 extending through the elongate member 101. FIG. 10A shows puncture of the trocar 1020 through the atrial wall 902 to form an extrapericardial penetration 512 as described herein. The trocar 1020 may be advanced so that its cutting tip is exposed distally of the internal cannula 1016 and then inserted through heart wall 902. A distal portion of the internal cannula 1016 may be configured to be advanced distally away from the distal end of the external cannula 1014 and through the extrapericardial penetration 512. The distal end of the external cannula 1014 may be configured to remain outside the extrapericardial penetration 512. The distal end of the external cannula 1014 may be in contact with, or may not be in contact with, the cardiac wall 902 outside the extrapericardial penetration 512 when the trocar 1020 and internal cannula 1016 are inserted into the extrapericardial penetration 512. Optionally the distal end of the external cannula 1014 may include a soft atraumatic engagement member to minimize trauma to the heart wall 902. Such engagement member may comprise an absorbent material to absorb any blood leaking from the extrapericardial penetration 512 and enhance sealing. Further, the engagement member may serve as a capture device for the optional shape-memory needles 1030 coupled to the internal cannula 1016, as described herein.

Figure 10B:
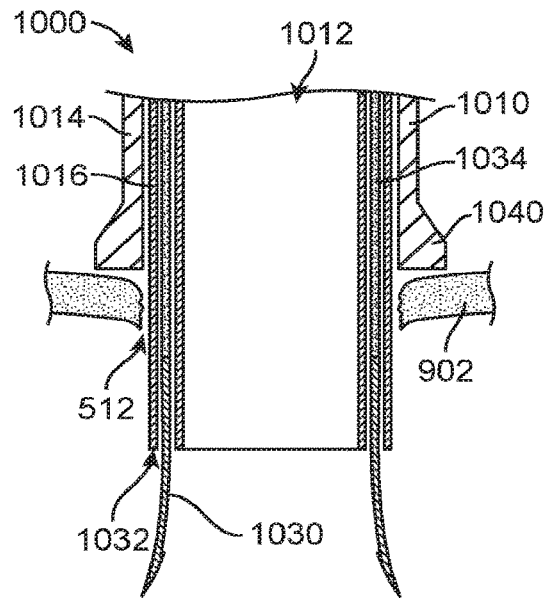
Figure 10C:
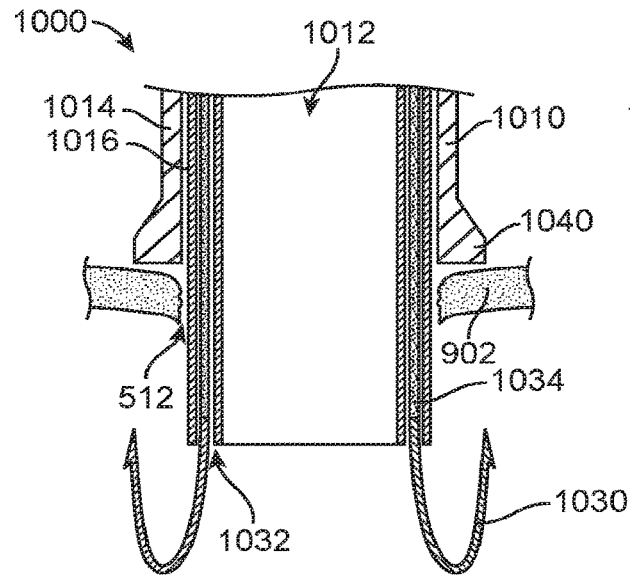

The surgical instrument may comprise a retention element 1030, for example a plurality of shape-memory needles disposed within one or more passages 1032 in the internal cannula 1016. Each of the shape-memory needles 1030 may be coupled to a length of suture 1034 extending proximally through the passages 1032 and out of the proximal end of the instrument 1000. The plurality of shape-memory needles 1030 may be movable from a delivery position (as shown in FIGS. 10A-10B), in which the shape-memory needles 1030 are disposed within one or more passages 1032 in the internal cannula 1016, to a deployed position distally of the internal cannula 1016 (as shown in FIG. 10C). The plurality of shape-memory needles 1030 may, for example, be extended out distally away from the distal end of the internal cannula 1016 in a straight, delivery position as shown in FIG. 10B. Once fully extended from the internal cannula 1016, the shape-memory needles 1030 may assume the curved deployed configuration shown in FIG. 10C. In exemplary embodiments, the shape-memory needles 1030 may comprise a super-elastic material such as Nitinol and may be configured to reside in the curved deployed configuration in an unconstrained, unbiased condition. When retained within the internal cannula 1016 in the delivery position, the shape-memory needles 1030 may be constrained in a straightened delivery configuration, but upon advancement from the internal cannula 1016 they may resiliently transform to the curved deployed configuration. Preferably, in such deployed configuration the needles 1030 may be curved approximately 160° to 180° such that the distal tips point in a proximal direction toward the interior wall of the heart while the proximal shafts of the needles 1030 are held in the passage(s) of the internal cannula 1016.

Figure 10D:
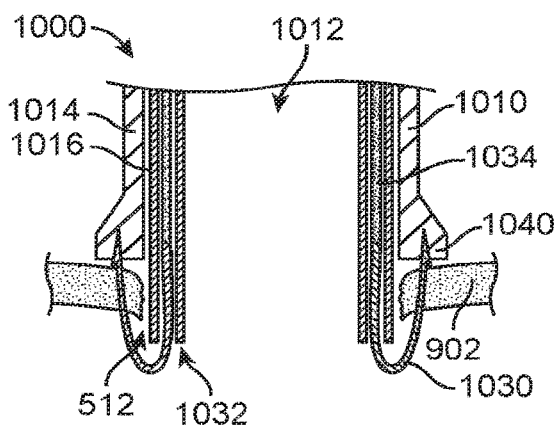

Retraction of the internal cannula 1016 relative to the external cannula 1014 while the plurality of shape memory needles 1030 are in the deployed position may retract the distal tips of the plurality of shape-memory needles 1030 through the cardiac wall 902 to be captured by a capture device 1040 coupled to the distal end of the external cannula 1014 as shown in FIG. 10D. In an exemplary embodiment, the distal tips of shape-memory needles 1030 may include a barb or arrowhead configured to pass into the compliant material of the capture device 1040 and resist removal therefrom in the reverse direction. The capture device 1040 may comprise a mesh or foam to facilitate capturing the needles tips 1030. The channel 1012 of the internal cannula 1016 may provide a pathway for additional instruments to access the internal chamber of the heart as described herein. Advantageously, while the surgical instrument 1000 is in use during a cardiac procedure, the shape-memory needles 1030 may serve to stabilize the external cannula 1014 against the atrial wall 902 and prevent inadvertent removal therefrom. Further, by applying tension to the suture 1034 coupled to each needle 1030, a seal can be created between the heart wall 902 and the internal cannula 1016 or the external cannula 1014 to inhibit blood loss.

In addition, the shape-memory needles 1030 may facilitate closure of the extrapericardial penetration 512 when the instrument 1000 is removed therefrom (e.g. as shown in FIGS. 17A-17E). The external cannula 1014 may be retracted relative to the internal cannula 1016 to withdraw the shape-memory needles 1030 from the heart. Preferably, the shape-memory needles 1030 have sufficient flexibility to straighten as they are pulled through the heart wall 902. Alternatively, a straightening element could be advanced over the needles 1030 from the external cannula 1014 to straighten them prior to withdrawal. In still another embodiment, the needles 1030 may have temperature-induced shape memory so as to assume a straightened configuration when heated or cooled to a specified temperature. The needles 1030 may be retracted with the external cannula 1014 out of the suprasternal opening, leaving a length of suture 1034 extending from each needle 1030 through the heart wall 902, and back out of the suprasternal opening. When the extrapericardial penetration 512 is to be closed, after withdrawing the internal cannula 1016, the sutures 1034 from each pair of needles 1030 may be tied together to draw the opposing tissue edges together.

Figure 11A:
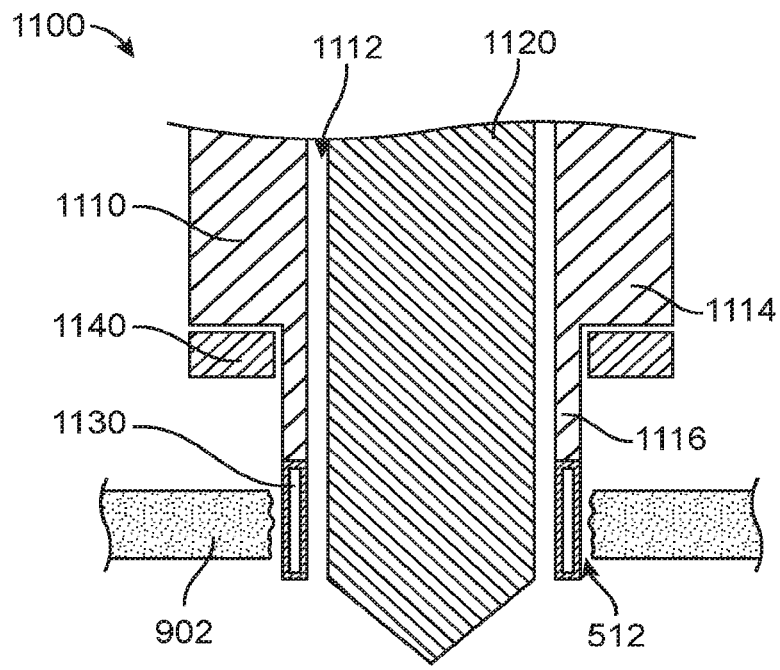
FIGS. 11A-11B show the distal end of yet another exemplary surgical instrument, in accordance with some embodiments.
Figure 11B:
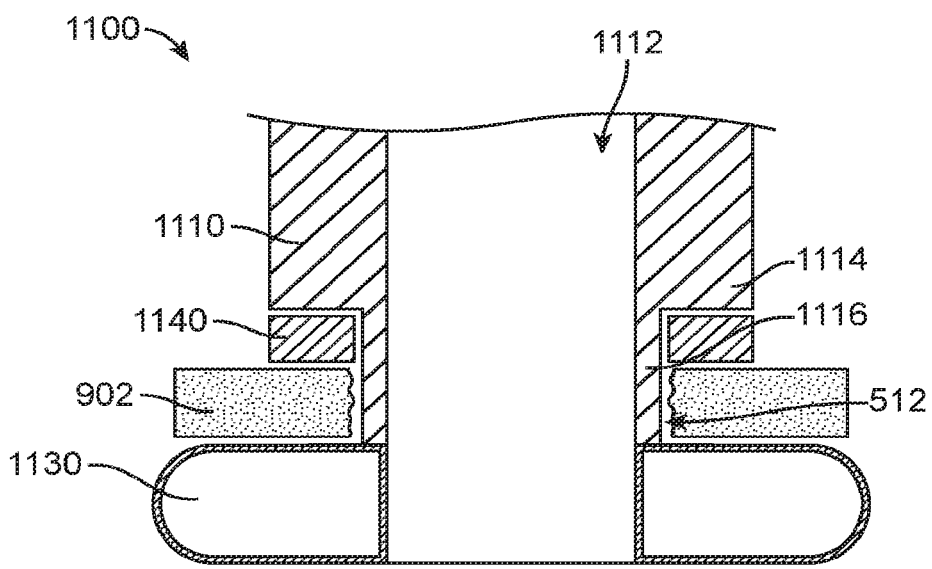

FIGS. 11A-11B show the distal end of yet another exemplary surgical instrument 1100, in accordance with some embodiments. The surgical instrument 1100 may comprise an elongate member 1110 having a channel 1112 extending therethrough as described herein. The elongate member 1110 may be configured to be advanced to contact a cardiac wall 902 of the left atrium 502 as described herein, for example to an extrapericardial location 512 on the dome 504 of the left atrium 502 as described herein. The elongate member 1110 may comprise a cutting tool 1120, for example a trocar, removably disposed within the channel 1112 and configured to make an extrapericardial penetration 512 through the cardiac wall 902 of the atrial dome 504 without penetrating the pericardial space of the heart as described herein. The elongate member 1110 may comprise a cannula having a distal end configured to be advanced into the extrapericardial penetration 512. FIG. 11A shows puncture of the trocar 1120 through the atrial wall 902 to form an extrapericardial penetration 512 as described herein. A distal portion of the elongate member 1110 may be configured to be advanced distally through the extrapericardial penetration 512. At least a portion of the distal end of the elongate member 1110 may be configured to remain outside the extrapericardial penetration 512. For example, the distal end of the elongate member 1110 may comprise a tip 1116 having a first diameter and a shoulder 1114 having a second diameter greater than the first such that the tip 1116 may be inserted through the extrapericardial penetration 512 up to the shoulder 1114 which may have a diameter too large to pass through the incision 512. Optionally the distal end may further include a tapered portion between the tip 1116 and the shoulder 1114 to provide a more gradual transition in diameter therebetween. The distal end of the elongate member 1110 may comprise a retention element 1130, for example a balloon coupled to a distal portion of the elongate member 1110, as described herein. In such embodiments the elongate member 1110 may include an inflation lumen communicating with the balloon 1130 to allow the delivery of an inflation fluid thereto. Alternatively, the elongate member 1110 may comprise external cannula and an internal cannula slidably disposed therein (e.g. as shown in FIG. 9C), wherein the balloon 1130 may be coupled to a distal portion of the inner cannula which may be configured to be advanced through the extrapericardial penetration 512. The balloon 1130 may have an undeployed position (as shown in FIG. 11A) and a deployed position (as shown in FIG. 11B). When deployed, the balloon 1130 may be inflated and configured to engage an internal portion of the cardiac wall 902 to stabilize the elongate member 1110 against the atrial wall 902, seal against blood leakage, and resist inadvertent removal of the elongate member 1110 from a cardiac wall 902 of the patient. In some embodiments, a conforming pad 1140 may be coupled to the distal end of the elongate member 1110. The conforming pad 1140 may be configured to stabilize the instrument 1100 and minimize trauma to the cardiac wall 902 when the balloon 1130 is inflated into the deployed configuration. Additionally, the conforming pad 1140 may comprise an absorbent material configured to absorb blood leakage from the penetration 512 and enhance sealing. The channel 1112 of the elongate member 1110 may provide a pathway for additional instruments to access the internal chamber of the heart as described herein.

Figure 12A:
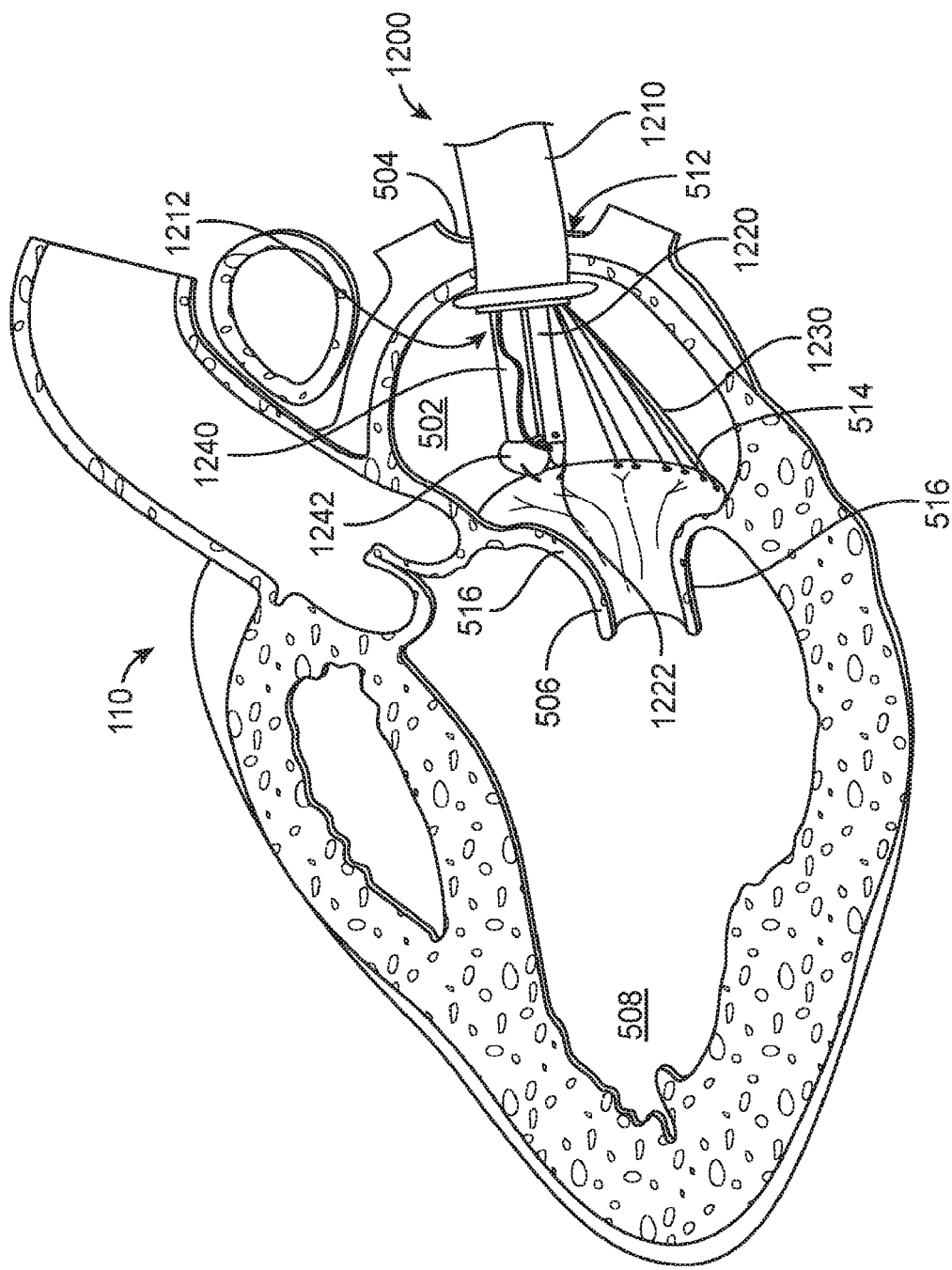
FIGS. 12A-12C show an exemplary surgical system for mitral valve annuloplasty, in accordance with some embodiments.
Figures 12B, 12C:
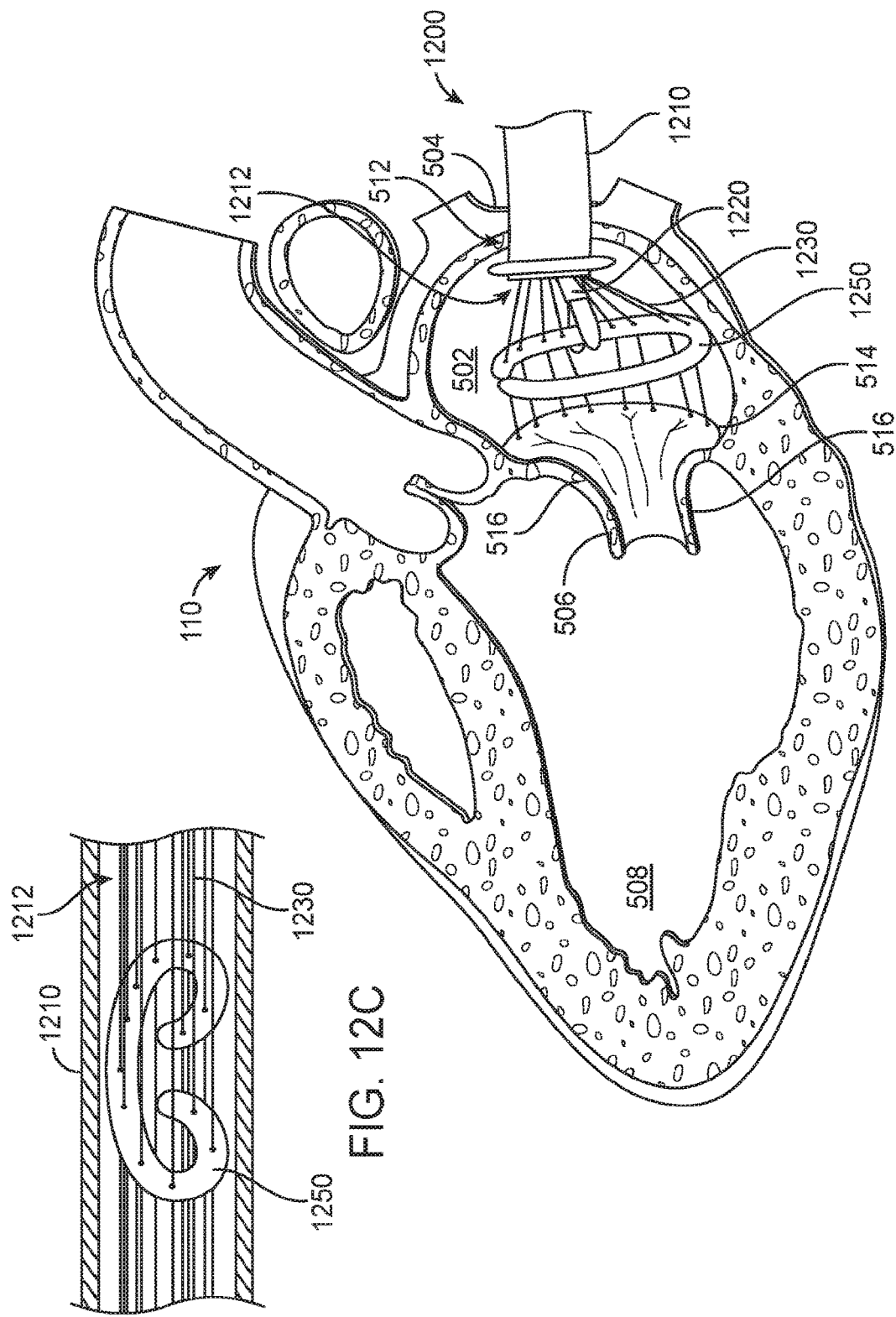

FIGS. 12A-12C show an exemplary surgical system 1200 for mitral valve annuloplasty.

The system 1200 may comprise any of the surgical access devices described herein, for example an elongate member 1210 having a channel 1212 extending therethrough as described herein. The mitral valve annuloplasty procedure may be performed while the heart 110 is beating. The procedural instrument 1220 may be advanced into the internal chamber of the heart 110 through the channel 1212 of the elongate member 1210 and configured to perform a mitral valve annuloplasty procedure. The procedural instrument 1220 may, for example, be configured to apply one or more sutures 1230 to an annulus 514 of a mitral valve 506 of the heart 110 as shown in FIG. 12A. The one or more sutures 1230 may have a curved needle 1222 attached to at least one free end and a length configured to extend outside the body through the channel 1212. The procedural instrument 1220 may be configured to grip the curved needle 1222 and drive it through the fibrous tissue of the mitral annulus 514, after which it may be withdrawn through the channel 1212. An annuloplasty band or ring 1540 may be coupled to the one or more sutures 1222. The annuloplasty ring 1250 may be configured to be advanced through the channel 1212 by sliding it down the sutures 1222 in a collapsed configuration (as shown in FIG. 12C) to the mitral valve 506, as shown in FIG. 12B. The band or ring 1250 may then be secured to the mitral valve 506 by tying knots in the one or more sutures 1230. Preferably the knots may be tied outside the patient's body and may be slid through the channel 1212 using an endoscopic knot pusher. Alternatively, crimping devices or other knot substitutes may be used to secure the sutures 1230. All or a portion of the annuloplasty band or ring 1250 may be resiliently deformable such that it may be shaped into a collapsed configuration to allow it to traverse the channel 1212 and then resiliently return to its undeformed shape upon advancement into the interior portion of the heart 110. Alternatively, all or part of the band or ring 1250 may be plastically shapable so that the surgeon may form it into a collapsed shape for delivery and reform it into a desired shape once in the heart 110 at the mitral position 506. The annuloplasty ring 1250 may be advanced through the channel 1212 by the same procedural device 1220 that applied the sutures 1230 to the annulus 514. Alternatively, a specialized procedural device may be provided to hold the annuloplasty ring 1250, advance it through the channel 1212, and hold it in position while sutures 1230 are secured.

A distal portion and/or distal end of the elongate member 1210 may be steerable or articulated as described herein in order to aid in passing the suture 1222 through the tissue, for example by modifying the procedural instrument's 1220 angle of approach. Alternatively or in combination, the distal end of the procedural element 1220 may be steerable or articulatable so as to bend or otherwise angle the distal end of the procedural element 1220 to a desired position to place the suture 1230.

An optional visualization device 1240, for example an endoscope comprising a blood displacement element 1242 on a distal end thereof, may be inserted into the channel 1212 of the elongate member 1210 along with the procedural instrument 1220 in order to visualize the internal chamber of the heart 110 and aid the user performing the annuloplasty procedure.

Figure 13A:
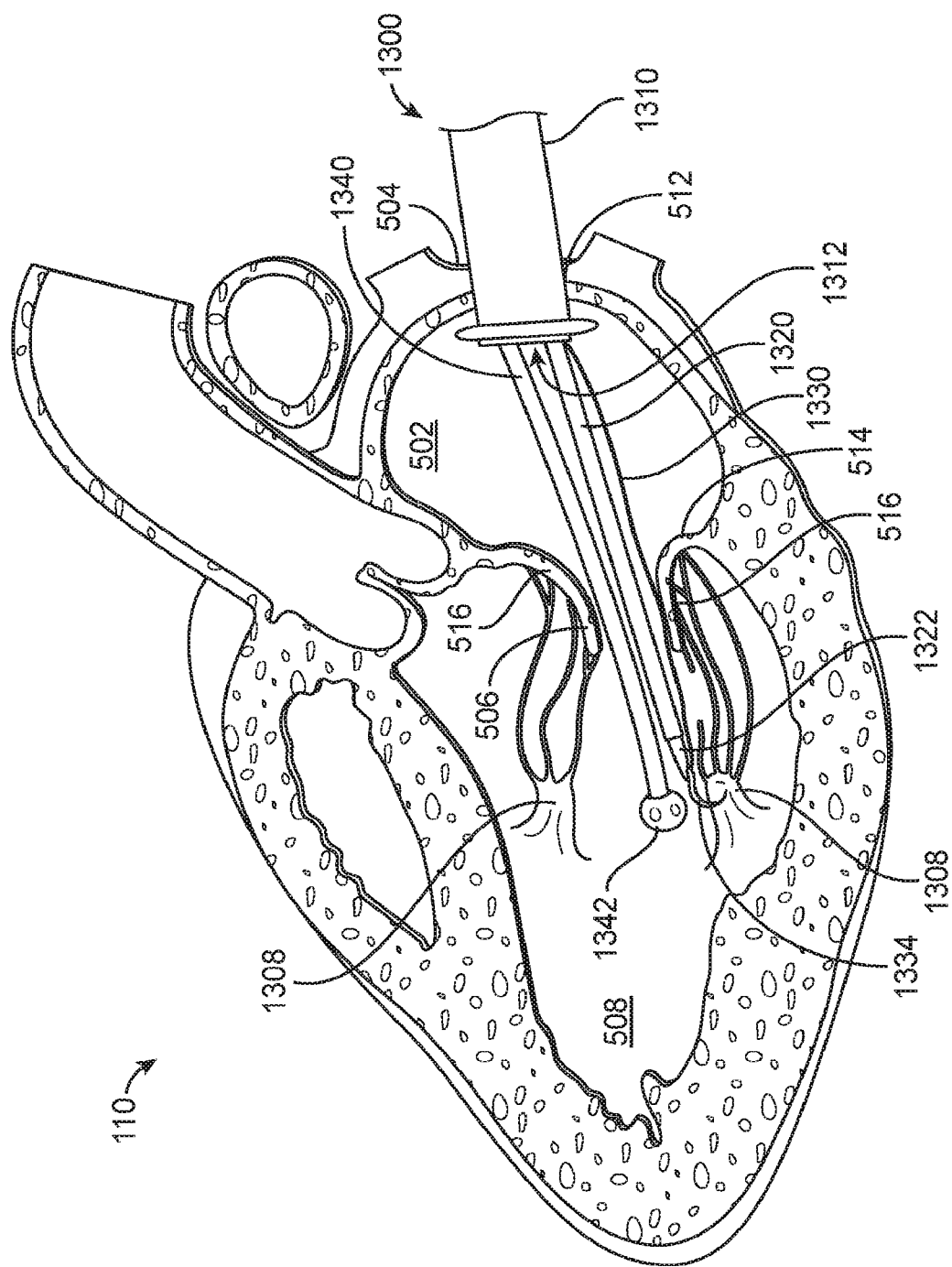
FIGS. 13A-13B show an exemplary surgical system for chordal repair, in accordance with some embodiments.
Figure 13B:
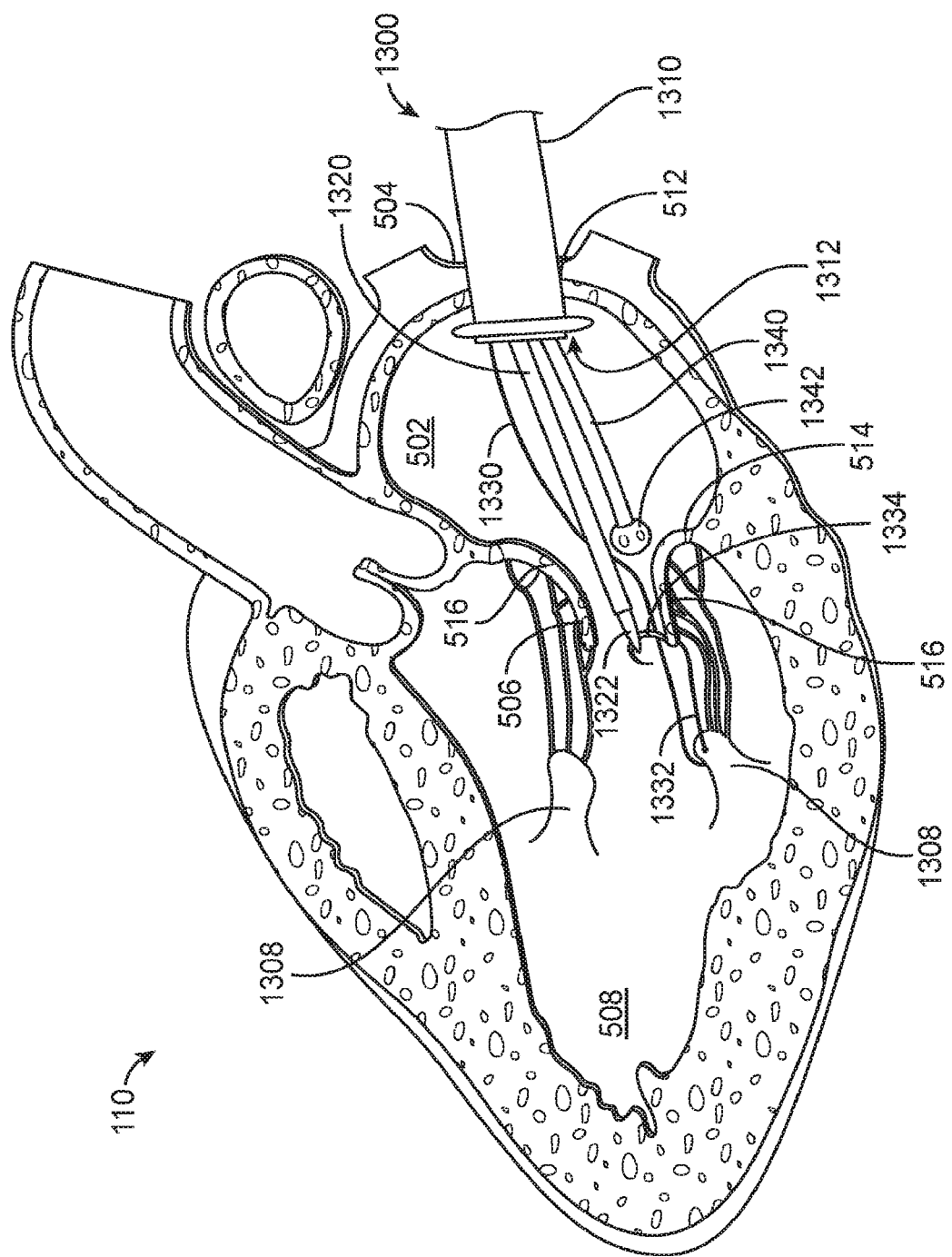

FIGS. 13A-13B show an exemplary surgical system 1300 for chordal repair or replacement procedure. The system 1300 may comprise any of the surgical access devices described herein, for example an elongate member 1310 having a channel 1312 extending therethrough as described herein. The mitral valve chordal repair or replacement procedure may be performed while the heart 110 is beating. The procedural instrument 1320 may be advanced into the internal chamber of the heart 110 through the channel 1312 of the elongate member 1310 and configured to perform a chordal repair or replacement procedure. The procedural instrument 1320 may, for example, comprise a distal end effector 1322 configured to couple one or more artificial chordae elements 1330 to at least one of a mitral valve leaflet 516 of the patient and a papillary muscle 1308 of the patient to form one or more artificial chordae tendineae 1332 therebetween. In exemplary embodiments, the artificial chordae elements 1330 may comprise a flexible strand, wire, or chord with a curved needle 1334 on a free end thereof. The instrument 1320 may be configured to grip the needle 1334 with the distal end effector 1322 and pass it through the papillary muscle 1308 (as shown in FIG. 13A). The same or a different procedural instrument 1320 may be used to pass the needle 1334 through the mitral valve leaflet 516 (as shown in FIG. 13B) at least once to leave the artificial chordae element 1330 extending therebetween. The artificial chordae element 1330 may be knotted or otherwise secured to both the leaflet 516 and the papillary muscle 1308 to act as an artificial chordae tendineae 1332 and improve mitral valve function (e.g. reduce mitral regurgitation). Before securing, the surgeon may adjust the position and/or tension of each artificial chordae element 1330 while observing mitral valve function until optimal valve function is achieved. Transesophageal and/or transthoracic echocardiography may optionally be used in making this assessment. This may be repeated to place multiple artificial chordae elements 1330 as needed. The artificial chordae element 1330 may comprise polytetrafluoroethylene (PTFE), or any other suitable material as will be known to one of ordinary skill in the art.

A distal portion and/or distal end of the elongate member 1310 may be steerable or articulated as described herein in order to aid in passing the artificial chordae element 1330 through the tissue, for example by modifying the procedural instrument's 1320 angle of approach. Alternatively or in combination, the distal end of the procedural element 1320 may be steerable or articulatable so as to bend or otherwise angle the distal end of the procedural element 1320 to a desired position to place the artificial chordae element 1330. An optional visualization device 1340, for example an endoscope comprising a blood displacement element 1342 on a distal end thereof, may be inserted into the channel 1312 of the elongate member 1310 along with the procedural instrument 1320 in order to visualize the internal chamber of the heart 110 and aid the user performing the chordal repair or replacement procedure.

Figure 14A:
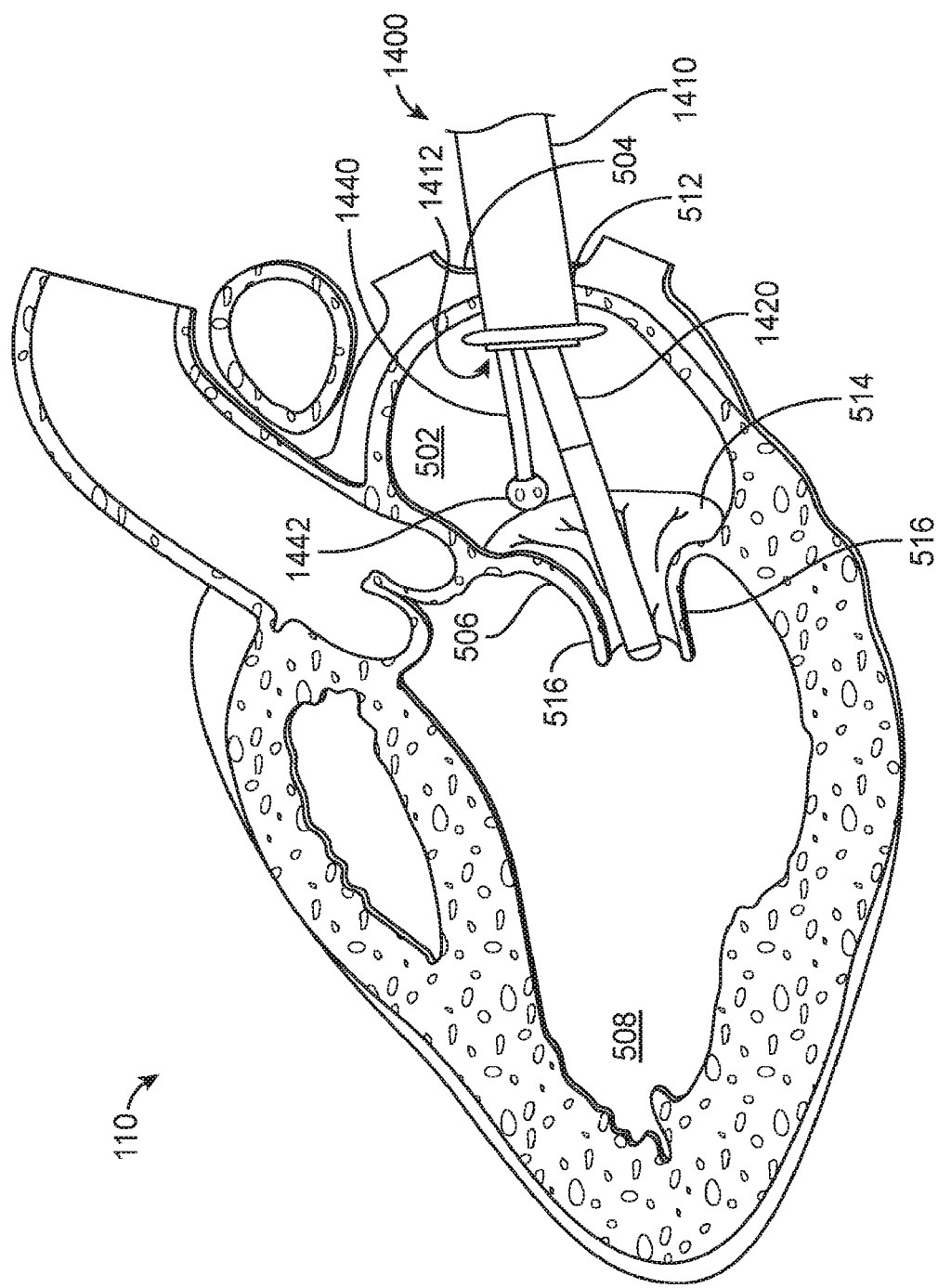
FIGS. 14A-14C show an exemplary surgical system for mitral valve replacement.
Figure 14B:
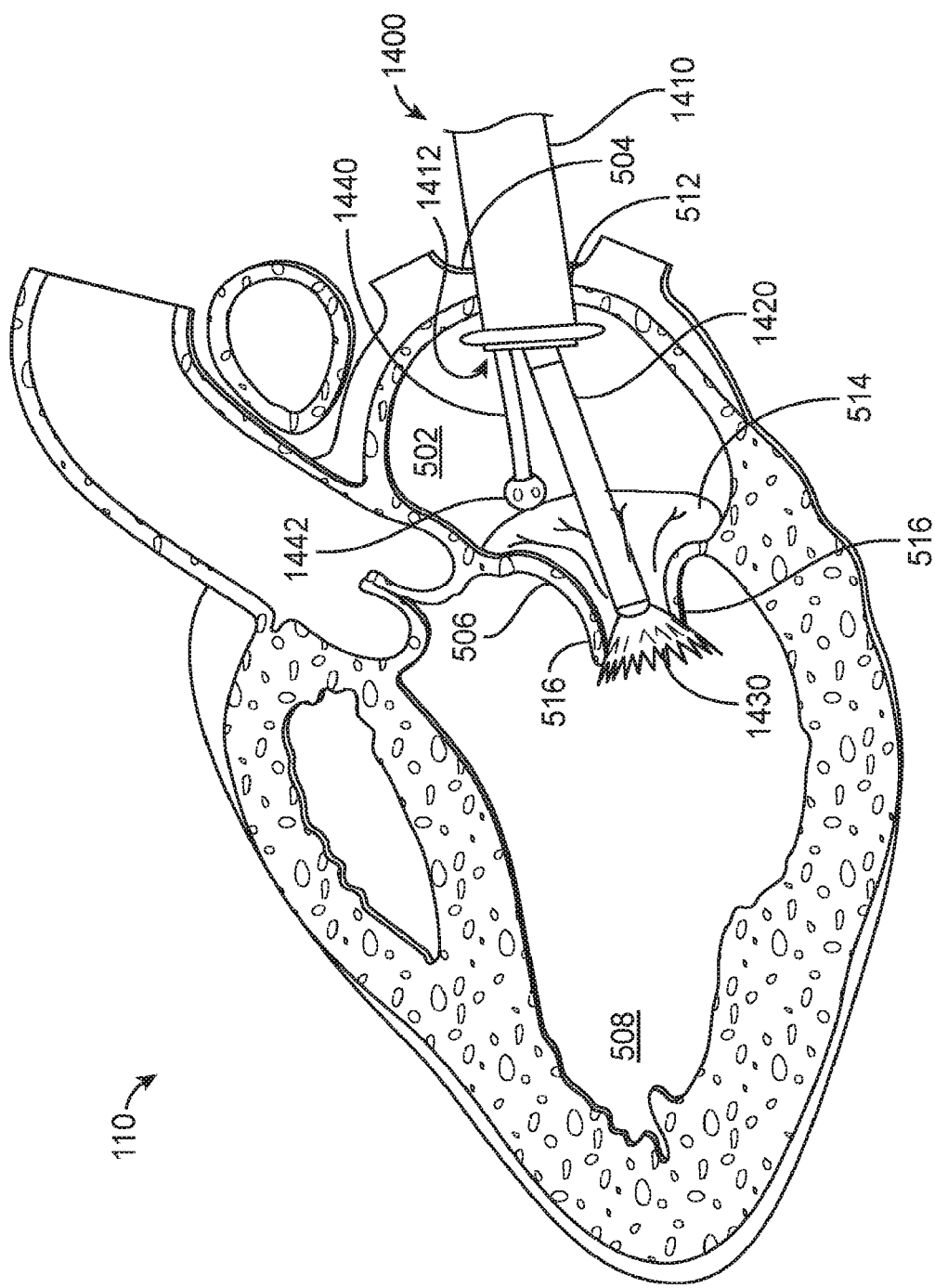
Figure 14C:
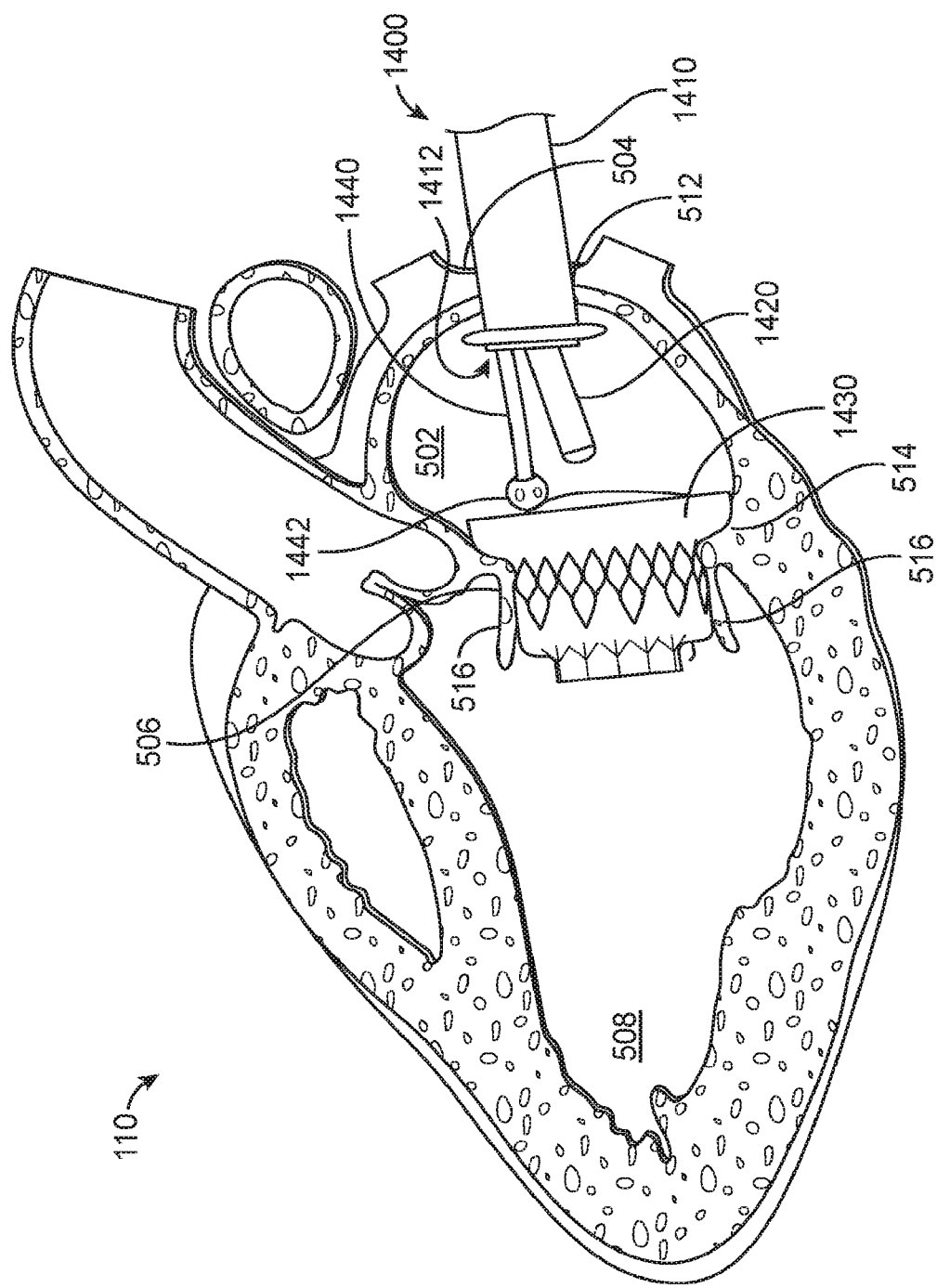

FIGS. 14A-14C show an exemplary surgical system 1400 for mitral valve replacement (for clarity the native chordae tendineae are not shown). The system 1400 may comprise any of the surgical access devices described herein, for example an elongate member 1410 having a channel 1412 extending therethrough as described herein. The mitral valve replacement procedure may be performed while the heart 110 is beating. The procedural instrument 1420 may be advanced into the internal chamber of the heart 110 through the channel 1412 of the elongate member 1410 and configured to perform a mitral valve replacement procedure. The procedural instrument 1420 may comprise a sheath configured to hold a prosthetic mitral valve 1430 in a distal end thereof. The prosthetic mitral valve 1430 may, for example, be a stented mitral valve, e.g. any available stented prosthetic valve which can be collapsed to a delivery diameter less than about 20 mm, more preferably less than about 15 mm, and suitable for placement using a left atrial approach. The prosthetic mitral valve 1430 may be contained in the sheath in a collapsed configuration while the procedural instrument 1420 is advanced into the internal chamber of the heart 110 as shown in FIG. 14A. The procedural instrument 1420 may for example be advanced from the extrapericardial penetration to a location adjacent the mitral valve annulus 514, for example about 4 cm to about 8 cm into the left atrium 502 depending on the size of the left atrium 502 of the patient. The distal end of the procedural instrument 1420 may be steerable as described herein so as to achieve a desired orientation relative to the native valve 506 prior to implantation of the prosthetic valve 1430. Once the distal end of the procedural instrument 1420 has been advanced into the desired position and/or orientation, the sheath may be retracted and the prosthetic mitral valve 1430 may be released (as shown in FIG. 14B) and expanded into an undeformed shape (as shown in FIG. 14C) inside the native mitral valve 506. The prosthetic mitral valve 1430 may be resiliently deformable into the collapsed configuration in which it can traverse the channel 1412 and resiliently return to its undeformed shape upon advancement into the interior portion of the heart 110. In some embodiments, one or both of the native mitral valve leaflets 516 may be removed prior to implantation of the prosthetic mitral valve 1430. In some embodiments, the native mitral valve leaflets 516 may remain in place prior to and after implantation of the prosthetic mitral valve 1430. Proper positioning and orientation of the prosthetic mitral valve 1430 may be visualized before, during, and/or after implantation using any of the visualization elements or devices described herein, for example using an endoscope 1440 disposed within the channel 1412 of the elongate member 1410 alone or in combination with transesophageal echocardiography and/or fluoroscopy.

A distal portion and/or distal end of the elongate member 1410 may be steerable or articulated as described herein in order to aid in passing the prosthetic mitral valve 1430 into the heart 110, for example by modifying the procedural instrument's 1420 angle of approach. Alternatively or in combination, the distal end of the procedural element 1420 may be steerable or articulatable so as to bend or otherwise angle the distal end of the procedural element 1420 to a desired position to place the prosthetic mitral valve 1430. An optional visualization device 1440, for example an endoscope comprising a blood dispersing element 1442 on a distal end thereof, may be inserted into the channel 1412 of the elongate member 1410 with the procedural instrument 1420 in order to visualize the internal chamber of the heart 110 and aid the user performing the mitral valve replacement.

Any of the surgical instruments or systems described herein may optionally comprise a closure or suturing device. After accessing the internal chamber of the heart and/or preforming one or more cardiac procedure therein, the distal portion of the surgical instrument may be removed from the heart and the extrapericardial penetration may then be closed.

In some embodiments, the extrapericardial penetration may be closed by cinching a pursestring suture placed circumferentially around the extrapericardial penetration as described herein.

In some embodiments, the extrapericardial penetration may be closed with the aid of one or more closure device (also referred to herein as a suturing device) as described herein.

Figure 15A:
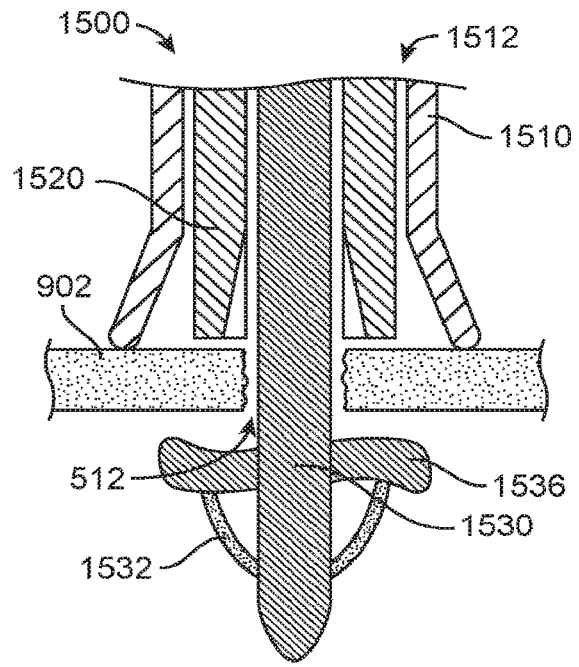
FIGS. 15A-15D show an exemplary closure device, in accordance with some embodiments.
Figure 15B:
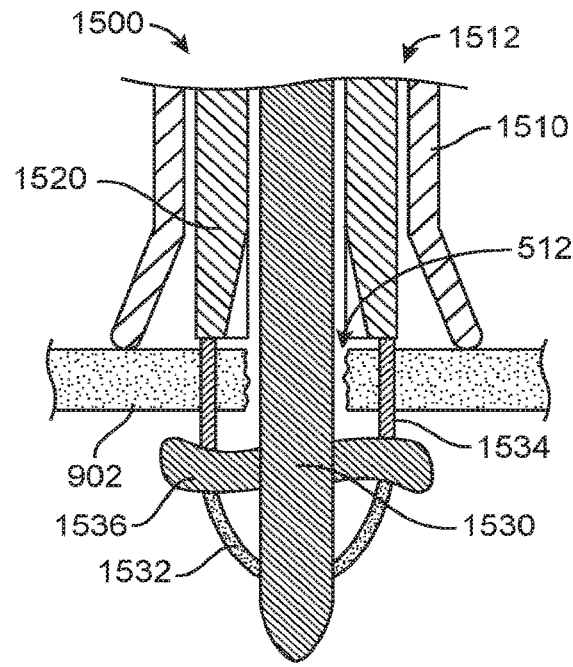
Figure 15C:
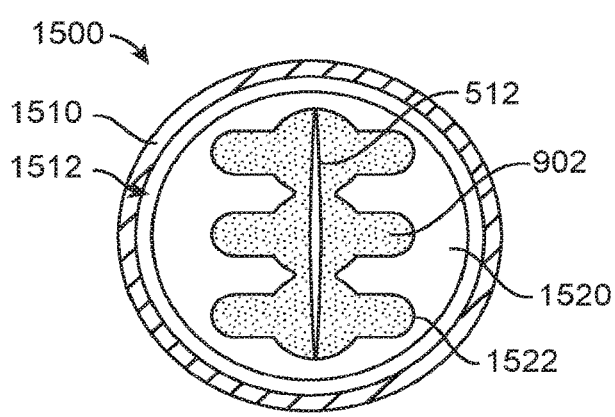

FIGS. 15A-15D show an exemplary closure device 1520, in accordance with some embodiments. The surgical instrument 1500 may comprise an elongate member 1510 having a channel 1512 extending therethrough as described herein. A closure device 1520 may be configured to be advanced through the channel 1512 and into the internal chamber of the heart as shown in FIG. 15A. The closure device 1520 may be configured to place one or more sutures 1532 in the cardiac wall 902 around the extrapericardial penetration 512. The one or more sutures 1532 may be placed simultaneously or one at a time. The closure device 1520 may comprise a closure cannula 1520 and a suturing device 1530. The closure cannula 1520 may be inserted into the elongate member 1510 so as to align with the puncture 512. The closure cannula 1520 may, for example, comprise one or more parallel guide paths 1522 (e.g. three guide paths as shown) extending longitudinally therein through which the suture device 1530 may be inserted to guide the suture device 1530 to spaced apart locations along the penetration 512, as shown in FIG. 15C.

Figure 15D:
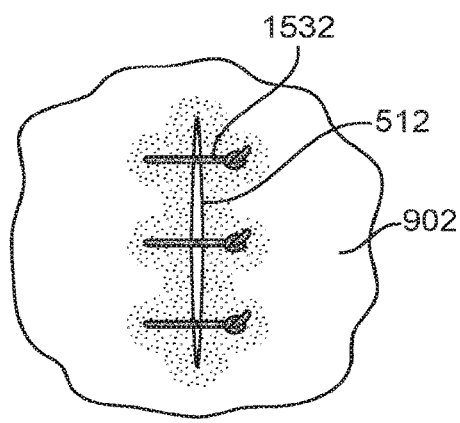

Referring again to FIG. 15A, the suture device 1530 may have a pair of deployable arms 1536 pivotably coupled to a distal portion thereof. Each arm 1536 may hold a needle capture element which may be interconnected by a length of suture 1532. The suture device 1530 may be inserted through the closure cannula 1520 with the arms 1536 in a contracted delivery position. Once within the heart, the arms 1536 may be deployed to an extended position as shown in FIG. 15A. A pair of needles 1534, each coupled to a length of suture 1532 extending out of the patient's body, may be advanced from the closure cannula 1520 distally through the heart wall 902. The needles 1534 may be aligned with the capture elements in the arms 1536 such that the needle tips 1534 may be captured and retained in the capture elements as shown in FIG. 15B. A length of suture 1532 attached to one of the needles 1534 may then be pulled from the closure cannula 1520, which may pull both of the capture elements and associated needles 1534 through the heart wall 902 and out of the body, leaving a length of suture 1532 looped through the heart wall 902 across the penetration 512. The closure cannula 1520 may then be removed. The penetration 512 may be closed by knotting the one or more sutures 1532 as shown in FIG. 15D.

FIGS. 16A-16E show another exemplary closure device 1600, in accordance with some embodiments. The surgical instrument 1600 may comprise an elongate member 1610 having a channel 1612 extending therethrough as described herein. The surgical instrument 1610 may, for example, be substantially similar to the device of FIGS. 10A-10D. In an exemplary embodiment, following deployment of the shape-memory needles 1630 and the use of the surgical instrument to perform a cardiac procedure as described herein, the plurality of shape-memory needles 1630 may be transformed into a straightened configuration to facilitate passage through the heart wall 902. In some embodiments the shape-memory needles 1630 may have temperature-induced shape memory characteristics and may be activated with heating or cooling to take on the straight, delivery position. Alternatively, a sheath may be advanced from the external cannula 1614 over each needle 1630 to straighten it. In other embodiments, the needles 1630 may be permanently straight and oriented to point in a proximal direction when deployed from the internal cannula 1616, which may include needle holding devices at its distal end similar to those described in connection with FIGS. 17A-17C. The surgical instrument 1600 may, for example, comprise three sets of shape-memory needle pairs 1630. Each pair of shape-memory needles 1630 may be connected by a single suture 1634, or each shape-memory needle 1630 may be coupled to its own separate length of suture 1634. Retraction of the external cannula 1614 away from the internal cannula 1616 and the extrapericardial penetration 512 may pull the plurality of needles 1630 and a plurality of sutures 1634 coupled thereto through the cardiac wall 902 as shown in FIG. 16B. Retraction of the internal cannula 1616 from the extrapericardial penetration 512 may leave one or more loops or lengths of sutures 1634 (e.g. three loops) in the atrial wall 902 as shown in FIG. 16C. The penetration 512 may be closed by tightening (e.g. with slip knots) or knotting 1636 the one or more sutures 1634 as shown in FIG. 16D. The shape-memory needles 1630 may be configured to insert the sutures 1634 into the atrial wall 902 tissue at locations spaced along the extrapericardial penetration 512 as demarcated by the dashed line in FIG. 16E.

Figure 17A:
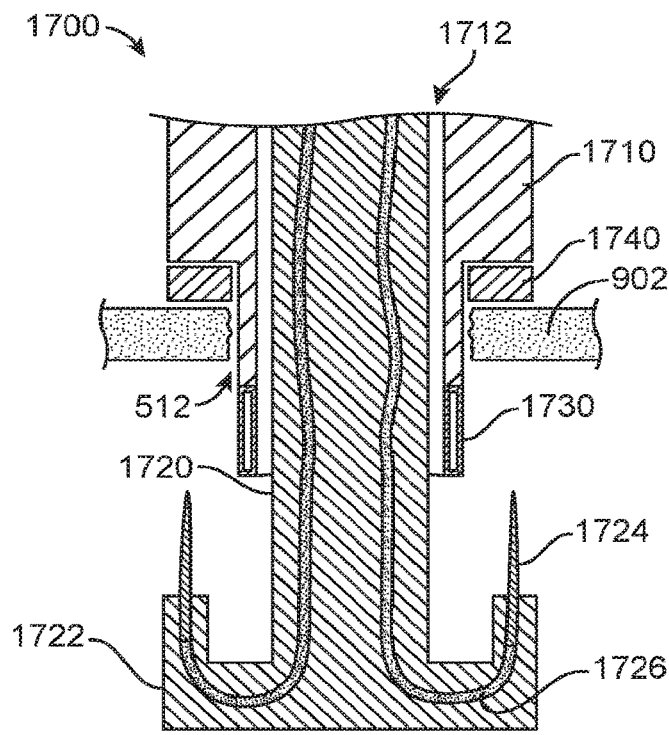
FIGS. 17A-17F show yet another exemplary closure device, in accordance with some embodiments.
Figure 17B:
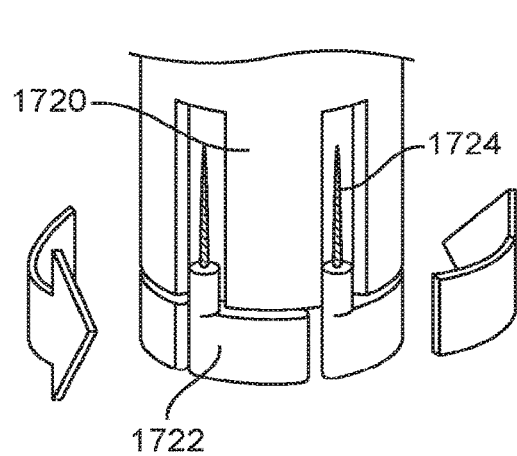
Figure 17C:
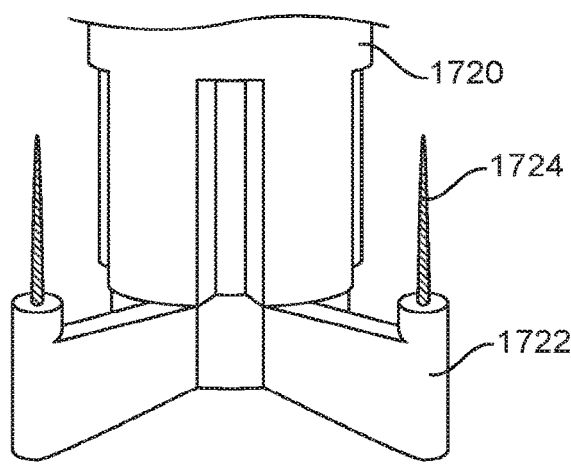
Figures 17D, 17E:
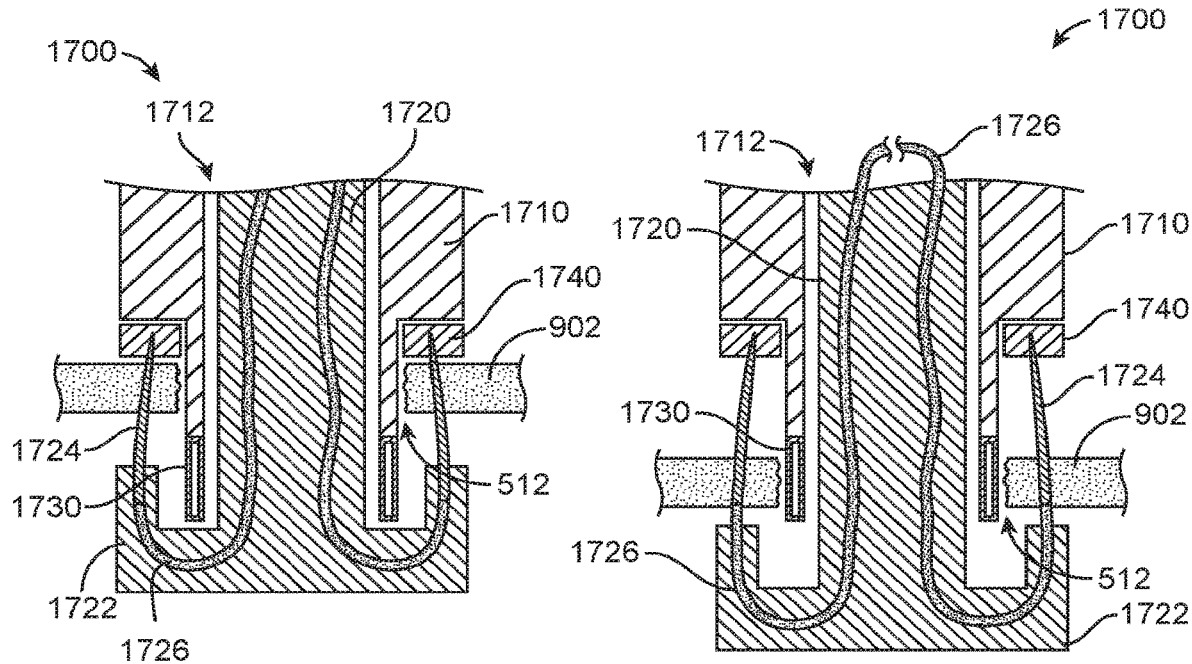
Figure 17F:
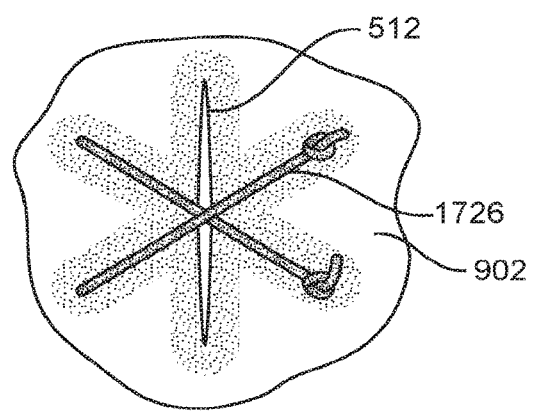

FIGS. 17A-17F show yet another exemplary closure device 1720, in accordance with some embodiments. The surgical instrument 1700 may comprise an elongate member 1710 having a channel 1712 extending therethrough as described herein. The surgical instrument 1710 may, for example, be substantially similar to the device of FIGS. 11A-11B, or any of the other surgical instruments described herein. Following the completion of the surgical procedure, the balloon 1730 may be deflated and a closure device 1720 may be inserted into the channel 1712 of the elongate member 1710 as shown in FIG. 17A. The closure device 1720 may comprise a plurality of extendable arms 1722, e.g. 2 to 6, having a low-profile undeployed position and a radially-extended deployed position. Each arm 1722 may be configured to hold a needle 1724 at the needle's dull end, with its sharp penetrating end pointing in a proximal direction. The plurality of needles 1724 may, for example, comprise two pairs of needles 1724, each pair of needles 1724 having a common suture 1726 extending therebetween. The plurality of needles 1725 may be configured to be contained within recesses in the suturing device 1720 when in the undeployed position shown in FIG. 17B. The closure device 1720 may be inserted into the heart in the undeployed position before being actuated to the deployed position shown in FIGS. 17A and 17C. Actuation of the arms 1722 into the deployed position may expose the needles 1724. Retraction of the closure device 1720 relative to the elongate member 1720 (e.g. inner cannula or distal tip of the elongate member as described herein) may push the plurality of needles 1724 through the cardiac wall 902 into a capture device 1740 coupled to the distal end of the external cannula 1710 as shown in FIG. 17D. The capture device 1740 may comprise a foam pad, fabric, screen, netting, or other porous material configured to receive the tips of the needles 1724 therein and resist removal therefrom. The needle tips 1724 may include barbs or arrowheads to facilitate secure capture. Retraction of the closure device 1720 may pull the plurality of needles 1724 and the sutures 1726 coupled thereto through the cardiac wall 902 as shown in FIG. 17E, leaving a plurality of suture 1726 loops extending through the tissue flaps on either side of the penetration 512. After removing the elongate member 1710 from the extrapericardial penetration 512, the penetration 512 may be closed by tightening (e.g. with slip knots) or knotting the one or more sutures 1726 in a suitable manner, such as an X-pattern across the penetration 512 as shown in FIG. 17F.

In any of the embodiments described herein, after accessing the heart, the distal portion of the surgical instrument may be removed from the opening adjacent the suprasternal notch of the patient. The opening may be closed after removing the distal portion of the surgical instrument from the opening.

It will also be understood that, although the terms first, second, etc. are, in some instances, used herein to describe various elements, these elements should not be limited by these terms. These terms are only used to distinguish one element from another. For example, a first instrument could be termed a second instrument, and, similarly, a second instrument could be termed a first instrument, without departing from the scope of the various described implementations. The first instrument and the second instrument are both instruments, but they are not the same instrument unless explicitly stated as such.

The terminology used in the description of the various described implementations herein is for the purpose of describing particular implementations only and is not intended to be limiting. As used in the description of the various described implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof The foregoing description, for purpose of explanation, has been described with reference to specific implementations. However, the illustrative discussions above are not intended to be exhaustive or to limit the scope of the claims to the precise forms disclosed. Many modifications and variations are possible in view of the above teachings. The implementations were chosen in order to best explain the principles underlying the claims and their practical applications, to thereby enable others skilled in the art to best use the implementations with various modifications as are suited to the particular uses contemplated.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. A method, comprising:
   inserting a distal portion of a surgical instrument into a body of a patient through an opening in a suprasternal notch of the patient;

advancing the distal portion of the surgical instrument anteriorly along the trachea of the patient toward a left atrium of a heart of the patient;

making an extrapericardial penetration through a cardiac wall at a first location on a dome of the left atrium of the patient, wherein the first location is a devoid of pericardium of the heart;

advancing the distal portion of the surgical instrument through the extrapericardial penetration in the dome of the left atrium to access an internal chamber of the heart, while a proximal portion of the surgical instrument remains outside the body of the patient;

inserting a procedural instrument through a channel in the surgical instrument into the internal chamber of the heart; and performing a surgical procedure in the internal chamber of the heart with the procedural instrument.

2. The method of claim 1, further comprising making an incision adjacent the suprasternal notch of the patient to form the opening in the suprasternal notch of the patient.

3. The method of claim 2, wherein the incision is made without cutting any portion of a sternum or any ribs of the patient.

4. The method of claim 1, wherein advancing the distal portion of the surgical instrument toward the heart comprises advancing the distal portion of the surgical instrument through a mediastinal space of the body.

5. The method of claim 1, wherein advancing the distal portion of the surgical instrument toward the heart comprises advancing the distal portion of the surgical instrument along a path anterior to the trachea.

6. The method of claim 5, wherein the path extends through a space between the trachea and an ascending aorta, or a space between the trachea and an arch of the aorta or the space between the innominate artery and the trachea.

7. The method of claim 5, wherein the path extends through a space between the trachea and a right branch of a pulmonary artery, a space between the trachea and a left branch of a pulmonary artery, or a space between the trachea and a bifurcation of a main pulmonary artery.

8. The method of claim 5, wherein the path is substantially parallel to a plane containing a longitudinal axis of the trachea.

9. The method of claim 5, wherein the path is substantially parallel to a plane defined by a primary bronchus.

10. The method of claim 1, wherein advancing the distal portion toward the heart comprises steering the distal portion of the surgical instrument to avoid internal structures of the patient.

11. The method of claim 10, wherein the internal structures of the patient comprise a pulmonary artery or a primary bronchus of the patient.

12. The method of claim 1, wherein inserting the distal portion of the surgical instrument through the opening comprises inserting the distal portion of the surgical instrument into a working channel of a mediastinoscope placed in the opening, and wherein advancing the distal portion comprises advancing the distal portion of the surgical instrument through the working channel.

13. The method of claim 1, wherein the surgical instrument comprises a cannula having a channel and a trocar disposed in the channel, wherein making the extrapericardial penetration comprises making an extrapericardial penetration with the trocar, and further comprising removing the trocar from the channel after advancing the distal portion of the surgical instrument through the extrapericardial penetration.

14. The method of claim 1, the incision through the cardiac wall at the first location is made without penetrating the pericardium of the heart.

15. The method of claim 1, further comprising contacting the left atrium of the heart with the distal portion of the surgical instrument prior to making the pericardial penetration.

16. The method of claim 1, further comprising sealing the cardiac wall of the extrapericardial penetration and the distal portion of the surgical instrument.

17. The method of claim 16, wherein sealing comprises tightening a pursestring suture in the cardiac wall around the extrapericardial penetration around the distal portion of the surgical instrument.

18. The method of claim 16, wherein sealing comprises expanding a sealing element coupled to a distal end of the surgical instrument.

19. The method of claim 18, wherein the sealing element comprises a compression flange or a balloon.

20. The method of claim 1, further comprising preventing inadvertent removal of the surgical instrument through the extrapericardial penetration.

* * * * *